(12) United States Patent
Amari et al.

(10) Patent No.: US 8,563,577 B2
(45) Date of Patent: Oct. 22, 2013

(54) ALKALOID AMINOESTER DERIVATIVES AND MEDICINAL COMPOSITION THEREOF

(75) Inventors: Gabriele Amari, Parma (IT); Mauro Riccaboni, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 243 days.

(21) Appl. No.: 13/165,948

(22) Filed: Jun. 22, 2011

(65) Prior Publication Data

US 2011/0311459 A1    Dec. 22, 2011

(30) Foreign Application Priority Data

Jun. 22, 2010  (EP) ..................... 10166894

(51) Int. Cl.
*A01N 43/90* (2006.01)
*A61K 31/44* (2006.01)
*C07D 453/02* (2006.01)

(52) U.S. Cl.
USPC ......................... 514/305; 546/137

(58) Field of Classification Search
USPC ......................... 546/137; 514/305
See application file for complete search history.

(56) References Cited

U.S. PATENT DOCUMENTS

| 2010/0035922 A1 | 2/2010 | Amari et al. |
| 2010/0173880 A1 | 7/2010 | Caligiuri et al. |

FOREIGN PATENT DOCUMENTS

| WO | 03/053996 | 7/2003 |
| WO | 2008/075005 | 6/2008 |

OTHER PUBLICATIONS

U.S. Appl. No. 13/232,415, filed Sep. 14, 2011, Amari, et al.
U.S. Appl. No. 13/729,388, filed Dec. 28, 2012, Amari, et al.
U.S. Appl. No. 13/165,936, filed Jun. 22, 2011, Amari, et al.
U.S. Appl. No. 13/165,930, Jun. 22, 2011, Amari, et al.
European Search Report in Application No. 10166894.5, issued Dec. 22, 2010.
U.S. Appl. No. 13/303,413, Nov. 23, 2011, Amari, et al.
U.S. Appl. No. 13/827,101, Mar. 14, 2013, Caligiuri, et al.

*Primary Examiner* — Niloofar Rahmani

(74) *Attorney, Agent, or Firm* — Oblon, Spivak, McClelland, Maier & Neustadt, L.L.P.

(57) ABSTRACT

The present invention relates to alkaloid aminoester compounds which act as muscarinic receptor antagonists, processes for the preparation of such a compound, compositions which contain such a compound, and therapeutic uses of such a compound.

12 Claims, No Drawings

ALKALOID AMINOESTER DERIVATIVES AND MEDICINAL COMPOSITION THEREOF

CROSS REFERENCES TO RELATED APPLICATIONS

This application claims priority to EP Patent Application No. 10166894.5, filed on Jun. 22, 2010, which is incorporated herein by reference in its entirety.

BACKGROUND OF THE INVENTION

1. Field of the Invention

The present invention relates to alkaloid aminoester derivatives which act as muscarinic receptor antagonists. The present invention also relates to processes for the preparation of such a compound, compositions which comprise such a compound, and therapeutic uses of such a compound.

2. Discussion of the Background

Quaternary ammonium salts acting as muscarinic (M) receptor antagonist drugs are currently used in therapy to induce bronchodilation for the treatment of respiratory diseases. Examples of well known M receptor antagonists are for instance represented by ipratropium bromide and tiotropium bromide.

Several chemical classes acting as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are for instance disclosed in WO 02/051841, WO 03/053966, and WO 2008/012290, all of which are incorporated herein by reference in their entireties.

Said M and M3 receptor antagonists are currently administered through inhalation route in order to deliver the drug directly at the site of action, thus limiting the systemic exposure and any undesirable side effect due to systemic absorption. However, even though the systemic exposure may be reduced through the inhalatory route, the compounds of the prior art may still, at least potentially, exhibit undesired side effects due to systemic absorption.

Therefore, it is highly desirable to provide M3 receptor antagonists able to act locally, while having high potency and long duration of action. Said drugs, once adsorbed, are degraded to inactive compounds which are deprived of any systemic side effects typical of muscarinic antagonists.

The co-pending application WO 2010/072338, which is incorporated herein by reference in its entirety, describes azonia-bicyclo[2.2.2]octane compounds acting as muscarinic receptor antagonists, further possessing the above therapeutically desirable characteristics.

There remains a need, however, for muscarinic receptor antagonists with even further improved properties.

SUMMARY OF THE INVENTION

Accordingly, it is one object of the present invention to provide novel alkaloid aminoester compounds which act as muscarinic receptor antagonists.

It is another object of the present invention to provide novel processes for the preparation of such a compound.

It is another object of the present invention to provide novel compositions which contain such a compound.

It is another object of the present invention to provide novel methods of treating and/or preventing certain diseases and conditions by administering an effective amount of such a compound.

These and other objects, which will become apparent during the following detailed description, have been achieved by the inventors' discovery that the presence of a heteroaryl group on the azonia-bicyclo[2.2.2]octane or pyrrolidinium ring, as per the details below, improves even further the duration of action of these latter compounds.

Thus, the present invention provides alkaloid aminoester derivatives of general formula (I), which act as muscarinic receptor antagonists.

In another embodiment, the present invention provides processes for the preparation of such compounds.

In another embodiment, the present invention provides pharmaceutical compositions which contain such a compound.

In another embodiment, the present invention provides methods for the treatment of respiratory disorders by administering such a compound.

In another embodiment, the present invention provides combinations of such a compound with other pharmaceutical active ingredients among which are, for instance, those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The compounds of the present invention thus behave as soft-drugs, since they are able to produce a more persistent bronchodilating effect in the lungs but are more consistently and rapidly transformed into inactive metabolites after passing into human plasma. This behavior gives great advantages in terms of safety.

DETAILED DESCRIPTION OF THE PREFERRED EMBODIMENTS

In particular, the invention is directed to alkaloid aminoester derivatives of general formula (I):

(I)

wherein:

$R_1$ is selected from the group consisting of $(C_1-C_6)$alkyl, aryl, $(C_3-C_8)$cycloalkyl, aryl$(C_1-C_6)$alkyl, and heteroaryl, optionally substituted by one or more substituents selected from the group consisting of halogen atoms, —OH, oxo, —SH, —NH$_2$, —NO$_2$, —CN, —CONHR$_5$, —CON(R$_5$)$_2$, —NHCOR$_5$, —COR$_5$, —CO$_2$R$_5$, $(C_1-C_6)$alkylsulfanyl, $(C_1-C_{10})$alkylsulfinyl, $(C_1-C_6)$alkylsulfonyl, $(C_1-C_6)$alkyl, $(C_1-C_6)$haloalkyl, $(C_1-C_6)$alkoxy, and $(C_1-C_6)$haloalkoxy;

$R_2$ is H or $(C_1-C_6)$alkyl optionally substituted by one or more substituents selected from the group consisting of halogen atoms, —OH, oxo, —SH, —NH$_2$, —NO$_2$, —CN, —CONHR$_5$, —CON(R$_5$)$_2$, —NHCOR$_5$, —COR$_5$, —CO$_2$R$_5$, $(C_1-C_6)$alkylsulfanyl, $(C_1-C_6)$alkylsulfinyl, $(C_1-C_6)$alkylsulfonyl, $(C_1-C_6)$alkyl, $(C_1-C_6)$haloalkyl, $(C_1-C_6)$alkoxy, and $(C_1-C_6)$haloalkoxy;

$R_3$ is H or is selected from the group consisting of $(C_1-C_6)$alkyl, aryl, $(C_3-C_8)$cycloalkyl, and heteroaryl, optionally substituted by one or more substituents selected from the group consisting of halogen atoms, —OH, oxo, —SH, —NH$_2$, —NO$_2$, —CN, —CONHR$_5$, —CON(R$_5$)$_2$, —CO$_2$R$_5$, $(C_1-$ $C_6$)alkylsulfinyl, ($C_1$-$C_6$)alkylsulfonyl, $C_6$)alkyl, ($C_1$-$C_6$)haloalkyl, ($C_1$-$C_6$)alkoxy, and ($C_1$-$C_6$)haloalkoxy;

$R_6$ represents a group of formula (I) or (ii) or (iii) or (iv)

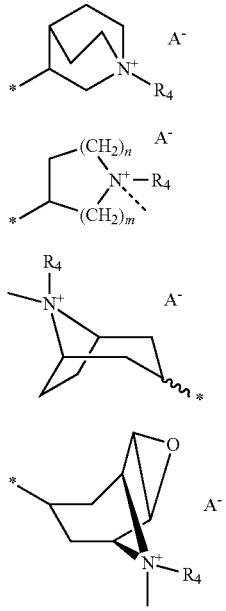

wherein
m=1, 2 or 3;
n=1, 2 or 3;
A is a physiologically acceptable anion;
$R_4$ is a group of formula (Y):

wherein
p is 0 or an integer of 1 to 4;
q is 0 or an integer of 1 to 4;
P is a heteroaryl, optionally substituted by one or more substituents selected from the group consisting of halogen atoms, —OH, oxo, —SH, —$NO_2$, —CN, —CON($R_5$)$_2$, —$NH_2$, —NHCOR$_5$, —$CO_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, and ($C_1$-$C_6$)alkoxy;

W is selected from the group consisting of aryl, ($C_3$-$C_8$) cycloalkyl, and heteroaryl, optionally substituted by one or more substituents selected from the group consisting of halogen atoms, —OH, oxo, —SH, —$NH_2$, —$NO_2$, —CN, —CONHR$_5$, —CON($R_5$)$_2$, —NHCOR$_5$, —COR$_5$, —$CO_2R_5$, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$) alkoxy, and ($C_1$-$C_6$)haloalkoxy;

$R_5$ is H or is selected from the group consisting of ($C_1$-$C_6$) alkyl, ($C_1$-$C_6$)haloalkyl, ($C_2$-$C_6$)alkenyl, ($C_3$-$C_8$)cycloalkyl, heteroaryl, and aryl optionally substituted by one or more substituents selected from the group consisting of halogen atoms, —OH, oxo, —SH, —$NH_2$,—$NO_2$,—CN,—CONH$_2$, —COOH, ($C_1$-$C_{10}$)alkoxycarbonyl, ($C_1$-$C_6$)alkylsulfanyl, ($C_1$-$C_6$)alkylsulfinyl, ($C_1$-$C_6$)alkylsulfonyl, ($C_1$-$C_6$)alkyl, ($C_1$-$C_6$)haloalkyl, ($C_1$-$C_6$)alkoxy, and ($C_1$-$C_6$)haloalkoxy;
and pharmaceutically acceptable salts thereof.

In the present description, unless otherwise specified, the term "halogen" includes fluorine, chlorine, bromine and iodine atoms.

The expression "($C_1$-$C_6$)alkyl", refers to straight or branched chain alkyl groups wherein the number of carbon atoms is from 1 to 6. Examples of said groups are methyl, ethyl, n-propyl, isopropyl, n-butyl, isobutyl, sec-butyl, tert-butyl, pentyl, hexyl, and the like.

The expression "($C_2$-$C_6$)alkenyl" refers to straight or branched carbon chains with one or more double bonds. Examples of said groups may thus comprise ethenyl, propenyl, butenyl, pentenyl, hexenyl, and the like.

The expression "($C_1$-$C_6$)alkoxy" refers to the above alkyl-oxy (e.g. alkoxy) groups. Examples of said groups may thus comprise methoxyl, ethoxyl, n-propoxyl, isopropoxyl, n-butoxyl, isobutoxyl, sec-butoxyl, tert-butoxyl, pentoxyl, hexoxyl, and the like.

Likewise, the expression "($C_1$-$C_6$)alkoxycarbonyl" refers to the above ($C_1$-$C_6$)alkoxy groups further bearing a carbonyl group among which is, for instance, acetoxy (e.g. acetyloxy-carbonyl), tert-butoxycarbonyl, and the like.

The expressions "($C_1$-$C_6$)haloalkyl" and "($C_1$-$C_6$)haloalkoxy", refer to the above ($C_1$-$C_6$)alkyl and ($C_1$-$C_6$)alkoxy groups wherein one or more hydrogen atoms are replaced by one or more halogen atoms, which can be the same or different.

Examples of the said ($C_1$-$C_6$)haloalkyl and ($C_1$-$C_6$)haloalkoxy groups may thus include halogenated, poly-halogenated and fully halogenated alkyl and alkoxy groups wherein all of the hydrogen atoms are replaced by halogen atoms, e.g. trifluoromethyl or trifluoromethoxyl groups.

Likewise, the derived expressions "($C_1$-$C_6$)alkylsulfanyl", "($C_1$-$C_6$)alkylsulfinyl" or "($C_1$-$C_6$)alkylsulfonyl" refer, respectively, to alkyl-S—, alkyl-SO— or alkyl-$SO_2$— groups.

The expression "($C_3$-$C_8$)cycloalkyl", refers to cyclic non-aromatic hydrocarbon groups with from 3 to 8 carbon atoms. Examples include cyclopropyl, cyclobutyl, cyclopentyl, cyclohexyl, cycloheptyl and the like.

The expression "aryl" refers to mono or bi- or tricyclic ring systems which have 6 to 20 ring atoms, preferably from 6 to 15 and wherein at least one ring is aromatic.

The expressions "aryl($C_1$-$C_6$)alkyl" and "heteroaryl($C_1$-$C_6$)alkyl refer to ($C_1$-$C_6$)alkyl groups further substituted by aryl or heteroaryl rings.

The expression "heteroaryl" refers to mono, bi- or tricyclic ring systems which have 5 to 20 ring atoms, preferably from 5 to 15, in which at least one ring is aromatic and in which at least one ring atom is a heteroatom or heteroaromatic group (e.g. N, NH, S or O).

Examples of suitable aryl or heteroaryl monocyclic systems include for instance phenyl, triazole (triazolyl), thiophene (thiophenyl), benzene (phenyl), pyrrole (pyrrolyl), pyrazole (pyrazolyl), imidazole (imidazolyl), isoxazole (isoxazolyl), oxazole (oxazolyl), oxadiazole (oxadiazolyl), isothiazole (isothiazolyl), thiazole (thiazolyl), pyridine (pyridinyl), imidazolidine (imidazolidinyl), and furan (furanyl) radicals and the like.

Examples of suitable aryl or heteroaryl bicyclic systems include naphthalene (naphthyl), biphenyl (biphenylyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzofuranyl, benzothiophenyl, benzoimidazolyl, dihydrobenzo dioxepin, and benzo oxazin radicals and the like.

Examples of suitable aryl or heteroaryl tricyclic systems include fluorene (fluorenyl) radicals as well as benzocondensed derivatives of the aforementioned heteroaryl bicyclic systems.

As far as $R_5$ is concerned, it is clear that, in any possible occurrence, it may represent H or one of the groups mentioned above.

Hence, by way of example, when $R_1$ is an aryl group further substituted by a —CON($R_5$)$_2$ group, the latter also includes —CONH$_2$, —CONHR$_5$ and —CON($R_5$)($R_5$), wherein $R_5$ is as set forth above.

Advantageously, the physiologically acceptable anions A$^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate, preferably chloride, bromide, and trifluoroacetate.

Besides the presence of A$^-$ anion, whenever further basic amino groups are present in the compounds of formula (I), additional physiological acceptable anions, among those formerly indicated, may be present. Likewise, in the presence of acidic groups such as COOH groups, corresponding physiological cation salts may be present as well, for instance including alkali or earth-alkali metal ions.

A first preferred group of compounds of general formula (I) is that wherein $R_1$ is aryl, aryl($C_1$-$C_6$)alkyl, or heteroaryl, optionally substituted by one or more substituents selected from the group consisting of halogen atoms, ($C_1$-$C_6$)alkyl, —CONHR$_5$ and —CO$_2$R$_5$; $R_2$ is H or ($C_1$-$C_6$)alkyl; and $R_3$, $R_5$, $R_6$ and A$^-$ have the above reported meanings.

Another preferred group of compounds of general formula (I) within this class, is that wherein $R_1$ is phenyl, benzyl, or thiophenyl, optionally substituted by one or more substituents as defined above; $R_2$ is H or ($C_1$-$C_6$)alkyl; and $R_3$, $R_5$, $R_6$ and A$^-$ have the above reported meanings.

An even more preferred group of compounds of general formula (I) is that wherein $R_3$ is selected from the group consisting of aryl and heteroaryl, optionally substituted by one or more substituents selected from the group consisting of halogen atoms and ($C_1$-$C_6$)alkoxy; and $R_1$, $R_2$, $R_6$ and A$^-$ have the above reported meanings.

Another preferred group of compounds of general formula (I) within this class, is that wherein $R_3$ is selected from the group consisting of phenyl, thiophenyl, benzothiophenyl, and pyridyl, optionally substituted as above indicated; and $R_1$, $R_2$, $R_6$ and A have the above reported meanings.

Another even more preferred group of compounds of general formula (I), is that wherein $R_6$ is a group of formula (I) or (ii); and $R_1$, $R_2$, $R_3$ and A$^-$ have the above reported meanings.

A more preferred group of compounds of general formula (I) within this class, is that wherein $R_6$ is a group of formula (I), wherein $R_4$ is a group of formula (Y) wherein p is 1 and q is 0, P is an heteroaryl group and W is selected from the group consisting of aryl, ($C_3$-$C_8$)cycloalkyl, and heteroaryl, optionally substituted by one or more groups selected from halogen atoms, —CN, ($C_1$-$C_6$)alkyl, and ($C_1$-$C_6$)alkoxy; and $R_1$, $R_2$, $R_3$ and A$^-$ have the above reported meanings.

Still more preferred within this class, are the compounds of general formula (I), wherein $R_6$ is a group of formula (I), wherein $R_4$ is a group of formula (Y) wherein p is 1 and q is 0, P is selected from oxadiazolyl, oxazolyl, triazolyl, benzoimidazolyl, thiazolyl, and isoxazolyl and W is selected from phenyl, pyrazolyl, cyclohexyl, dihydrobenzofuranyl, benzothiophenyl, piridinyl, thiazolyl, oxadiazolyl, and thiophenyl, optionally substituted by one or more groups selected from halogen atoms, —CN, methyl and methoxy; and $R_1$, $R_2$, $R_3$ and A$^-$ have the above reported meanings.

Another preferred group of compounds of general formula (I) is that wherein $R_6$ is a group of formula (ii), wherein n and m are 1, $R_4$ is a group of formula (Y) wherein p is 1 and q is 0, P is an heteroaryl and W is selected from the group consisting of aryl and heteroaryl; and $R_1$, $R_2$, $R_3$ and A$^-$ have the above reported meanings.

According to specific embodiments, the present invention provides the following compounds:

| Compound | Chemical name |
|---|---|
| C63 | (R)-1-((5-phenyl-1,2,4-oxadiazol-3-yl)methyl)-3-((R)-2-phenyl-2-(phenylamino)acetoxy)-1-azoniabicyclo[2.2.2]octane chloride |
| C64 | (R)-3-((R)-2-phenyl-2-(phenylamino)acetoxy)-1-((2-phenyloxazol-4-yl)methyl)-1-azoniabicyclo[2.2.2]octane chloride |
| C65 | (R)-3-((R)-2-phenyl-2-(phenylamino)acetoxy)-1-((2-phenylthiazol-4-yl)methyl)-1-azoniabicyclo[2.2.2]octane chloride |
| C66 | (R)-3-((R)-2-phenyl-2-(phenylamino)acetoxy)-1-((5-phenylisoxazol-3-yl)methyl)-1-azoniabicyclo[2.2.2]octane chloride |
| C67 | (R)-1-((3-phenyl-1,2,4-oxadiazol-5-yl)methyl)-3-((R)-2-phenyl-2-(phenylamino)acetoxy)-1-azoniabicyclo[2.2.2]octane chloride |
| C68 | (R)-1-((5-phenyl-1,3,4-oxadiazol-2-yl)methyl)-3-((R)-2-phenyl-2-(phenylamino)acetoxy)-1-azoniabicyclo[2.2.2]octane chloride |
| C69 | (R)-1-((2-(2-cyanophenyl)oxazol-4-yl)methyl)-3-((R)-2-phenyl-2-(phenylamino)acetoxy)-1-azoniabicyclo[2.2.2]octane chloride |
| C70 | (R)-3-((R)-2-phenyl-2-(phenylamino)acetoxy)-1-((2-(thiophen-2-yl)oxazol-4-yl)methyl)-1-azoniabicyclo[2.2.2]octane chloride |
| C71 | (R)-3-(2-(4-fluorophenyl)-2-(3-fluorophenylamino)acetoxy)-1-((5-phenyl-1,2,4-oxadiazol-3-yl)methyl)-1-azoniabicyclo[2.2.2]octane chloride |
| C72 | (R)-3-(2-((4-fluorophenyl)(methyl)amino)-2-phenylacetoxy)-1-((5-phenyl-1,2,4-oxadiazol-3-yl)methyl)-1-azoniabicyclo[2.2.2]octane chloride |
| C73 | (R)-3-(2-(4-chlorophenylamino)-2-phenylacetoxy)-1-((5-phenyl-1,2,4-oxadiazol-3-yl)methyl)-1-azoniabicyclo[2.2.2]octane chloride |
| C74 | (R)-3-(2-(4-fluorophenyl)-2-(phenylamino)acetoxy)-1-((2-phenyloxazol-4-yl)methyl)-1-azoniabicyclo[2.2.2]octane chloride |
| C75 | (R)-3-(2-(4-(methoxycarbonyl)phenylamino)-2-phenylacetoxy)-1-((5-phenyl-1,2,4-oxadiazol-3-yl)methyl)-1-azoniabicyclo[2.2.2]octane chloride |
| C76 | (R)-3-(2-(3-fluorophenyl)-2-(phenylamino)acetoxy)-1-((2-phenyloxazol-4-yl)methyl)-1-azoniabicyclo[2.2.2]octane chloride |
| C77 | (R)-3-(2-(2,5-difluorophenylamino)-2-phenylacetoxy)-1-((5-phenyl-1,2,4-oxadiazol-3-yl)methyl)-1-azoniabicyclo[2.2.2]octane chloride |
| C78 | (R)-3-(2-(3-(methylcarbamoyl)phenylamino)-2-phenylacetoxy)-1-((5-phenyl-1,2,4-oxadiazol-3-yl)methyl)-1-azoniabicyclo-[2.2.2]octane chloride |

-continued

| Compound | Chemical name |
|---|---|
| C79 | (3R)-1-((5-phenyl-1,2,4-oxadiazol-3-yl)methyl)-3-(2-phenyl-2-(o-tolylamino)acetoxy)-1-azoniabicyclo[2.2.2]octane chloride |
| C80 | (3R)-1-((5-phenyl-1,2,4-oxadiazol-3-yl)methyl)-3-(2-(phenylamino)-2-(thiophen-2-yl)acetoxy)-1-azoniabicyclo[2.2.2]octane 2,2,2-trifluoroacetate |
| C81 | (R)-3-(2-(benzylamino)-2-phenylacetoxy)-1-((5-phenyl-1,2,4-oxadiazol-3-yl)methyl)-1-azoniabicyclo[2.2.2]octane 2,2,2-trifluoroacetate |
| C82 | (3R)-3-(2-(2-(methoxycarbonyl)thiophen-3-ylamino)-2-(6-methoxypyridin-3-yl)acetoxy)-1-((5-phenyl-1,2,4-oxadiazol-3-yl)methyl)-1-azoniabicyclo[2.2.2]octane 2,2,2-trifluoroacetate |
| C83 | (3R)-1-methyl-1-((5-phenyl-1,2,4-oxadiazol-3-yl)methyl)-3-(2-phenyl-2-(phenylamino)acetoxy)pyrrolidinium 2,2,2-trifluoroacetate |
| C84 | (R)-1-((5-(4-fluorophenyl)-1,2,4-oxadiazol-3-yl)methyl)-3-((R)-2-phenyl-2-(phenylamino)acetoxy)-1-azoniabicyclo[2.2.2]octane 2,2,2-trifluoroacetate |
| C85 | (R)-3-((R)-2-phenyl-2-(phenylamino)acetoxy)-1-((5-p-tolyl-1,2,4-oxadiazol-3-yl)methyl)-1-azoniabicyclo[2.2.2]octane 2,2,2-trifluoroacetate |
| C86 | (R)-1-((5-(4-chlorophenyl)-1,2,4-oxadiazol-3-yl)methyl)-3-((R)-2-phenyl-2-(phenylamino)acetoxy)-1-azoniabicyclo[2.2.2]octane 2,2,2-trifluoroacetate |
| C87 | (R)-1-((5-(3-methoxyphenyl)-1,2,4-oxadiazol-3-yl)methyl)-3-((R)-2-phenyl-2-(phenylamino)acetoxy)-1-azoniabicyclo[2.2.2]octane chloride |
| C88 | (R)-1-((5-(2-methoxyphenyl)-1,2,4-oxadiazol-3-yl)methyl)-3-((R)-2-phenyl-2-(phenylamino)acetoxy)-1-azoniabicyclo[2.2.2]octane chloride |
| C89 | (R)-1-((5-methyl-2-phenyl-2H-1,2,3-triazol-4-yl)methyl)-3-((R)-2-phenyl-2-(phenylamino)acetoxy)-1-azoniabicyclo[2.2.2]octane bromide |
| C90 | (R)-1-((5-(3-fluorophenyl)-1,2,4-oxadiazol-3-yl)methyl)-3-((R)-2-phenyl-2-(phenylamino)acetoxy)-1-azoniabicyclo[2.2.2]octane chloride |
| C91 | (R)-1-((5-(2-fluorophenyl)-1,2,4-oxadiazol-3-yl)methyl)-3-((R)-2-phenyl-2-(phenylamino)acetoxy)-1-azoniabicyclo[2.2.2]octane chloride |
| C92 | (R)-1-((5-(1,3-dimethyl-1H-pyrazol-5-yl)-1,2,4-oxadiazol-3-yl)methyl)-3-((R)-2-phenyl-2-(phenylamino)acetoxy)-1-azoniabicyclo[2.2.2]octane chloride |
| C93 | (R)-1-((5-cyclohexyl-1,2,4-oxadiazol-3-yl)methyl)-3-((R)-2-phenyl-2-(phenylamino)acetoxy)-1-azoniabicyclo[2.2.2]octane chloride |
| C94 | (R)-3-((R)-2-phenyl-2-(phenylamino)acetoxy)-1-((5-(thiazol-2-yl)-1,2,4-oxadiazol-3-yl)methyl)-1-azoniabicyclo[2.2.2]octane chloride |
| C95 | (R)-1-((5-(4-methoxyphenyl)-1,2,4-oxadiazol-3-yl)methyl)-3-((R)-2-phenyl-2-(phenylamino)acetoxy)-1-azoniabicyclo[2.2.2]octane chloride |
| C96 | (R)-1-((5-(2,3-dihydrobenzofuran-5-yl)-1,2,4-oxadiazol-3-yl)methyl)-3-((R)-2-phenyl-2-(phenylamino)acetoxy)-1-azoniabicyclo[2.2.2]octane chloride |
| C97 | (R)-1-((5-(benzo[b]thiophen-2-yl)-1,2,4-oxadiazol-3-yl)methyl)-3-((R)-2-phenyl-2-(phenylamino)acetoxy)-1-azoniabicyclo[2.2.2]octane chloride |
| C98 | (R)-3-(2-(methyl(phenyl)amino)-2-phenylacetoxy)-1-((5-phenyl-1,2,4-oxadiazol-3-yl)methyl)-1-azoniabicyclo[2.2.2]octane chloride |
| C99 | (R)-3-((R)-2-(4-fluorophenylamino)-2-phenylacetoxy)-1-((5-phenyl-1,2,4-oxadiazol-3-yl)methyl)-1-azoniabicyclo[2.2.2]octane chloride |
| C100 | (R)-3-(2-(3-fluorophenylamino)-2-phenylacetoxy)-1-((5-phenyl-1,2,4-oxadiazol-3-yl)methyl)-1-azoniabicyclo[2.2.2]octane chloride |
| C101 | (R)-1-((5-cyclohexyl-1,2,4-oxadiazol-3-yl)methyl)-3-(2-(3-fluorophenylamino)-2-phenylacetoxy)-1-azoniabicyclo[2.2.2]octane chloride |
| C102 | (R)-3-((R)-2-phenyl-2-(phenylamino)acetoxy)-1-((5-(pyridin-4-yl)-1,2,4-oxadiazol-3-yl)methyl)-1-azoniabicyclo[2.2.2]octane chloride |
| C103 | (R)-1-((5-benzyl-1,2,4-oxadiazol-3-yl)methyl)-3-((R)-2-phenyl-2-(phenylamino)acetoxy)-1-azoniabicyclo[2.2.2]octane chloride |
| C104 | (R)-1-((1H-benzo[d]imidazol-2-yl)methyl)-3-((R)-2-phenyl-2-(phenylamino)acetoxy)-1-azoniabicyclo[2.2.2]octane 2,2,2-trifluoroacetate |
| C105 | (3R)-3-(2-(3-fluorophenylamino)-2-phenylacetoxy)-1-((5-(thiazol-2-yl)-1,2,4-oxadiazol-3-yl)methyl)-1-azoniabicyclo[2.2.2]octane chloride |
| C106 | (R)-1-((5-(1,3-dimethyl-1H-pyrazol-5-yl)-1,2,4-oxadiazol-3-yl)methyl)-3-(2-(3-fluorophenylamino)-2-phenylacetoxy)-1-azoniabicyclo[2.2.2]octane chloride |
| C107 | (R)-3-(2-(benzo[b]thiophen-3-yl)-2-(phenylamino)acetoxy)-1-((5-phenyl-1,2,4-oxadiazol-3-yl)methyl)-1-azoniabicyclo[2.2.2]octane chloride |
| C108 | (3R)-1-((5-(3-fluorophenyl)-1,2,4-oxadiazol-3-yl)methyl)-3-(2-(3-fluorophenylamino)-2-phenylacetoxy)-1-azoniabicyclo[2.2.2]octane 2,2,2-trifluoroacetate |

The compounds of formula (I) show at least one chiral center, which is represented by the carbon atom with asterisk as set forth below:

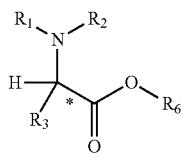
(I)

Further, depending on the meanings of $R_1$, $R_2$, $R_3$ and $R_6$, it will be clear that additional asymmetric centers may be present in the compounds of formula (I). Therefore, the invention also includes any of the optical stereoisomers, diastereomers and mixtures thereof, in any proportion.

In one of the preferred embodiment, the chiral center on the quinuclidine ring of the moiety $R_6$ represented by formula (i)

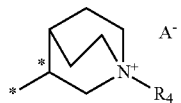
(i)

shows a R configuration.

In the present invention, since the absolute configuration of the diastereomers is not defined, they are indicated in the examples as diastereomer 1, 2, or mixtures of them.

The present invention also provides pharmaceutical compositions of compounds of formula (I) alone or in combination or in admixture with one or more pharmaceutically acceptable carriers and/or excipients.

The present invention also provides pharmaceutical compositions suitable for administration by inhalation such as, for instance, inhalable powders, propellant-containing metering aerosols or propellant-free inhalable formulations.

The present invention also provides compounds of formula (I) for use as a medicament.

The present invention also provides compounds of formula (I) for use in the treatment of broncho-obstructive or inflammatory diseases, preferably asthma or chronic bronchitis or chronic obstructive pulmonary disease (COPD).

In a further aspect, the present invention provides the use of the compounds of formula (I) for the manufacture of a medicament for the prevention and/or treatment of broncho-obstructive or inflammatory diseases, preferably asthma or chronic bronchitis or chronic obstructive pulmonary disease (COPD).

The present invention also provides a method for the prevention and/or treatment of broncho-obstructive or inflammatory diseases, preferably asthma or chronic bronchitis or chronic obstructive pulmonary disease (COPD), which comprises administering to a subject in need thereof a therapeutically effective amount of a compound of general formula (I).

The present invention also provides pharmaceutical compositions suitable for administration by inhalation, such as inhalable powders, propellant-containing metering aerosols or propellant-free inhalable formulations.

The present invention also provides devices which may be a single- or multi-dose dry powder inhaler, a metered dose inhaler and a soft mist nebulizer comprising the compounds of formula (I).

The present invention also provides kits comprising the above pharmaceutical compositions in a suitable vial or container and a device which may be a single- or multi-dose dry powder inhaler, a metered dose inhaler and a soft mist nebulizer, adapted to hold the above vial or container.

The compounds of formula (I) may be prepared according to known methods.

The present invention is also directed to various well known processes, suitable for the preparation of a compound of formula (IV):

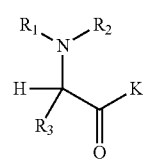
(IV)

which are reported in the following:

Route A. The process comprises the alkylation of an amine compound of formula (III):

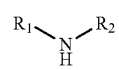
(III)

with a compound of formula (II)"

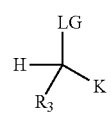
(II)

in which LG is a suitable leaving group and K is a carboxyl group, either as such or in an optionally protected form.

Route B. The process comprises the coupling of an amine of formula (III) and a ketone of formula (VII):

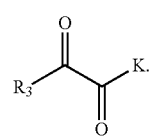
(VII)

Route C. The process comprises a reaction of an equimolar mixture of a boronic acid (VIII):

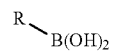
(VIII)

with glyoxylic acid (IX) and amine (III).

Route D. The process comprises a reaction between a compound of formula (X):

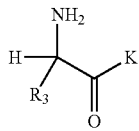
(X)

with a reagent of formula (XI):

(XI)

in which z is a carbonyl group or a leaving group such as an halide or sulfonate ester.

The present invention is also directed to two well known processes, suitable for the preparation of a compound of formula (VI):

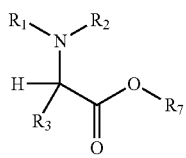
(VI)

which are described below.

Route F. The process comprises the coupling of alcohol (V):

(V)

with a compound of formula (IV):

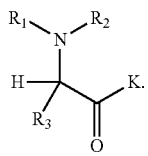
(IV)

Route G. The process comprises the coupling of a compound of formula (XII):

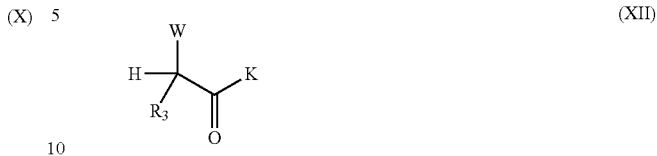
(XII)

with an alcohol (V) to yield a compound of formula (XIII):

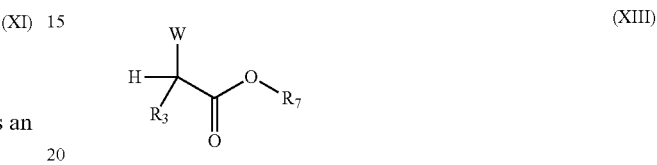
(XIII)

which is further alkylated with a compound of formula (III).

The present invention is also directed to a process for the preparation of a compound of formula (I) which comprises:

(a) the alkylation of a compound of general formula (VI):

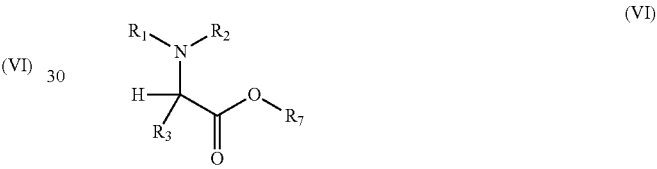
(VI)

wherein $R_7$ represents a group of formula (i') or (ii') or (iii') or (iv'):

(i')

(ii')

(iii')

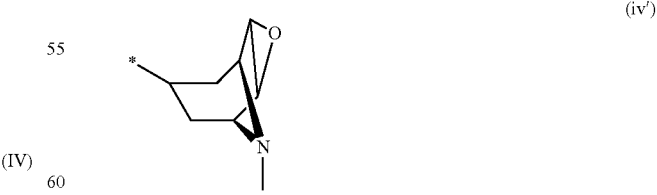
(iv')

with an alkylating agent of formula (XIV):

A-$R_4$ (XIV)

in which A is a suitable leaving group selected from the group consisting of halide and sulfonate ester, so as to obtain a compound of formula (I); and, optionally (b) the conversion of the compound of formula (I) into another compound of formula (I) and/or into a pharmaceutically acceptable salt thereof.

The operative conditions that may be used in the process of the present invention are described in more details below and are further reported in the following Scheme 1.

The starting materials for the preparation of the compounds of formula (I), that is the compounds of formula (II), as well as any reactant of the process, are known or easily prepared according to known procedures.

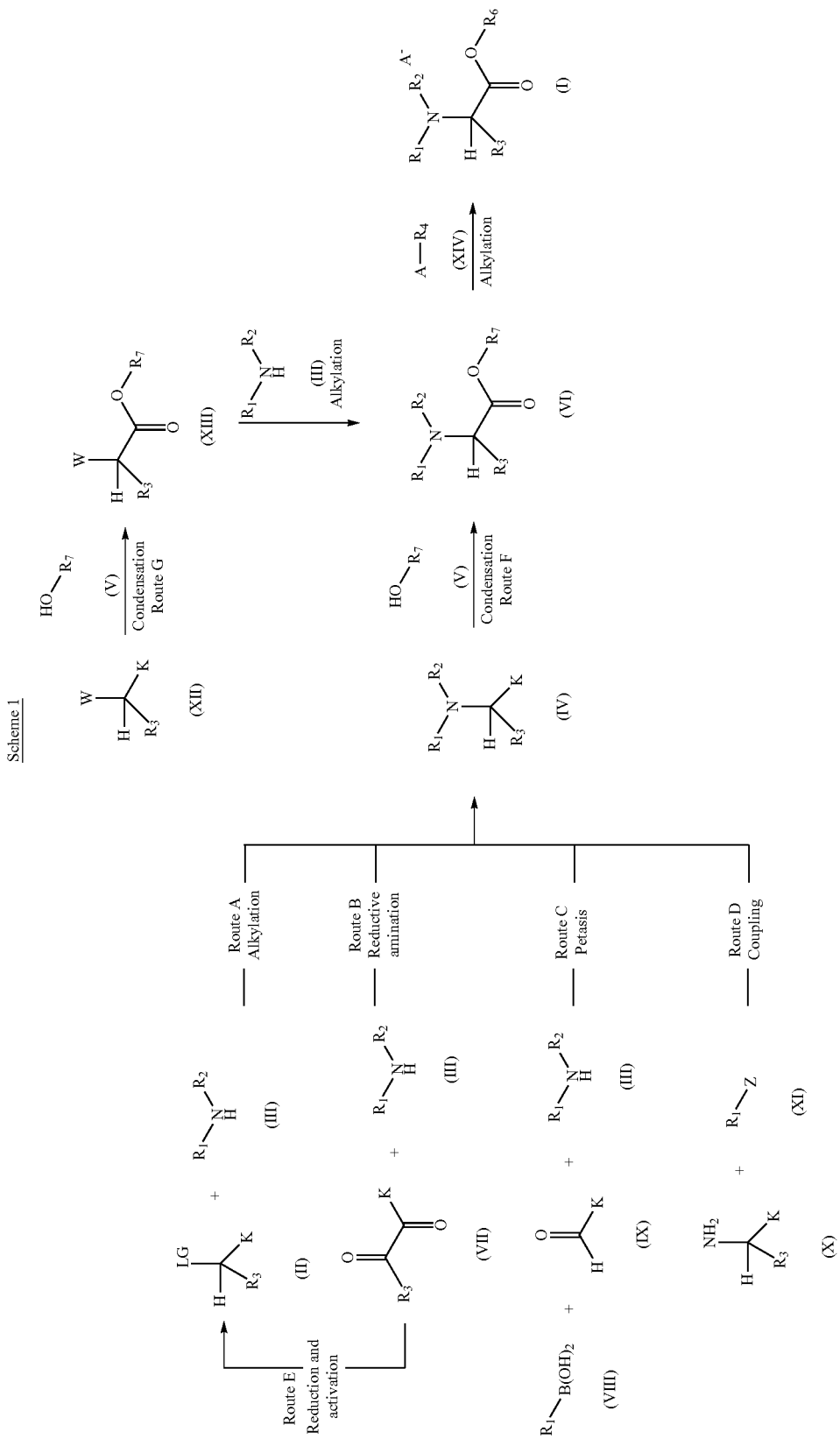

Procedure for the Preparation of Compounds of Formula (I).

According to a particular embodiment of the present invention, the compounds of general formula (I) may be for instance prepared, for example, following synthetic pathways described in scheme 1. Compounds of general formula (IV) may be prepared according to four different routes: A, B, C, and D.

According to Route A of the process, the compounds of general formula (IV) may be prepared through the alkylation of an amine of general formula (III), wherein $R_1$ and $R_2$ are as described above, with a compound of general formula (II), in which LG is a suitable leaving group (e.g. an halide such as bromine) and K is a carboxyl group in an optionally protected form.

Typically, LG is a halide atom, more preferably, a bromine atom. K may be a carboxyl group either as such or in an optionally protected form, typically including carboxyalkyl ester groups (e.g. K=COO($C_1$-$C_6$)alkyl), preferably carboxymethyl (e.g. COOMe).

The alkylation reaction may be promoted by the presence of a base, for instance an amine, selected from the group consisting of triethylamine, pyridine, and 4-dimethylaminopyridine, either neat or in a suitable solvent (e.g. acetonitrile). This reaction is usually performed in a temperature range from about 0° C. to about 130° C. over a period of about 1 hour to about 74 hours. The reaction may be conducted under conventional heating (using an oil bath) or under microwave heating. The reaction may be carried out in an open vessel or in a sealed tube.

According to Route B, the coupling of amine of general formula (III) and a ketone of general formula (VII) may be carried out using a reductive amination reaction, following one of the different procedures reported in literature (e.g.: Suwa T., *Synthesis*, 2000, 6, 789 or Fache, F. *Tetrahedron*, 1996, 52/29, 9777 or Quiang, K., *Adv. Synth. Catal.*, 2007, 349, 1657, all of which are incorporated herein by reference in their entireties).

Alternatively, compounds of general formula (VII) can be converted into compounds of general formula (II) (Route E) using known conditions. In a typical procedure, a ketone of formula (VII) is treated with a reducing agent such as sodium borohydride and the like, in a suitable solvent (e.g. ethanol and methanol) to smoothly provide the corresponding alcohol intermediate. The subsequent conversion of the alcohol moiety in a leaving group (LG) affords compounds of general formula (II). This activation can be effected according to one of the standard procedures broadly reported in the literature (a survey of the suitable reactions is given by Carey, F. A. and Sundeberg, R. J. *Advanced Organic Chemistry*, Third Edition (1990), Plenum Press, New York and London, pg 121, which is incorporated herein by reference in its entirety). For instance, the alcohol intermediate could be treated with methanesulphonyl chloride (LG=Ms) in presence of a base such as triethylamine, pyridine, 4-dimethylaminopyridine, and the like, either neat or in aprotic solvent (e.g. dichloromethane). This reaction is usually performed in a temperature range from about 0° C. to about 130° C. over a period of about 1 hour to about 74 hours.

According to Route C, a compound of general formula (IV) might be prepared by means of a Petasis-Mannich reaction following one of the different procedures reported in literature (e.g.: Petasis N. A., Akritopoulou I., *Tetrahedron Lett.*, 1993, 34, 583; Follmann, M., *Synlett*, 2005, 6, 1009; Kausik K. N., *Tetrahedron Letters*, 2005, 46, 2025, all of which are incorporated herein by reference in their entireties). In a typical procedure, an equimolar mixture of boronic acid (VIII), glyoxylic acid (IX), and amine (III) were dissolved in a suitable solvent (e.g. dichloromethane, acetonitrile) and stirred. This reaction is usually performed in a temperature range from about 0° C. to about 110° C. over a period of about 1 hour to about 74 hours. The reaction may be conducted under conventional heating (using an oil bath) or under microwave heating. The reaction may be carried out in an open vessel or in a sealed tube.

According to Route D, a compound of formula (X) may be reacted with an alkylating agent of general formula (XI), in which z is a suitable leaving group such as a carbonyl group or an halide (i.e. bromine, iodine, chlorine) or sulfonate ester (i.e. tosylate, triflates, mesylate), according to known procedures (e.g. Huang, *Tetrahedron*, 1997, 53/37, 12391, which is incorporated herein by reference in its entirety).

When z=O, the compound of formula (X) is reacted with an aldehyde or ketone of general formula (XI) to achieve the corresponding imine that is reduced to compound (IV) by treatment with a suitable reducing agent, following one of the procedures reported in literature (a survey of the suitable reactions is given by Carey, F. A. and Sundeberg, R. J. *Advanced Organic Chemistry*, Third Edition (1990), Plenum Press, New York and London, chapter 5, 219 or Ando, A., *Tetrahedron*, 1989, 45/16, 4969, both of which are incorporated herein by reference in their entireties).

In case $R_1$ is an aryl or heteroaryl and z is a halogen (typically a iodine or bromine), the coupling between compounds of general formula (X) and (XI) may be promoted by a suitable catalyst. In a typical procedure, the catalyst is a copper catalyst (e.g. copper iodide), and the reaction is performed in the presence of a suitable base selected from the group consisting of potassium and cesium carbonate or amines such as triethylamine, in solvents selected from the group consisting of dimethyl sulfoxide (DMSO) and DMF, at a temperature ranging from ambient to about 110° C., over a period ranging from about one to about 48 hours. The reaction may be carried out under conventional heating (using an oil bath) or under microwave irradiation. The reaction may be conducted either in an open vessel or in a sealed tube (Ma, D., *Tetrahedron Asymmetry*, 1996, 7/11, 3075 or Kurokawa, M., *Heterocycles*, 2007, 71/4, 847, both of which are incorporated herein by reference in their entireties).

In case $R_1$ is an aryl or heteroaryl and z is a halogen (typically fluorine or chlorine), compounds of general formula (X) and (XI) may react under the typical conditions of the aromatic nucleophilic substitution to afford compound (IV).

Compounds of general formula (VI) may then be prepared according to two different routes.

According to Route F, compounds of formula (VI) may be prepared by coupling the alcohol of formula (V) with a compound of formula (IV). The operative conditions are chosen on the basis of the reactivity of the alcohol (V), the commercial availability of reagents such as (IV) and of the compatibility of other groups being present in both reactants (for a general reference on the above reaction and operative conditions thereof see, for instance, Carey, F. A. and Sundeberg, R. J. *Advanced Organic Chemistry*, Third Edition (1990), Plenum Press, New York and London, pg 145, which is incorporated herein by reference in its entirety).

In particular, in the case K is a protecting carboxyl group, the protecting group has to be first removed before the coupling reaction takes place. When K is a carboxyester moiety (e.g. K=COOMe), removal of the protecting group is carried out under hydrolysis conditions, typically in the presence of any suitable aqueous base selected from the group consisting of sodium, lithium and potassium hydroxide. The reaction is performed in any suitable solvent, for instance in the presence of tetrahydrofuran or dioxane, at room temperature (RT) and over a period of about 1 hour to about 36 hours. When starting from a compound of formula (IV) wherein K is carboxyl, standard amidation and peptide coupling conditions may be applied to obtain the compounds of formula (VI). The said conditions include, for instance, activating intermediate (IV) by means of one or more equivalents of a commercially available condensing agent such as a carbodiimide (e.g. N,N'-dicyclohexylcarbodiimide (DCC) and the like) in the presence of N-hydroxybenzotriazole (HOBt). An organic base such as triethylamine may be also present in the reaction mixture. The activated intermediate may be either isolated, or pre-formed or generated in situ, and then properly reacted with the alcohol of formula (V). Suitable solvents for the coupling reaction include, but are not limited to, halocarbon solvents (e.g. dichloromethane), tetrahydrofuran, dioxane, and acetonitrile. The reaction proceeds at temperature ranging from about 0° C. to about 170° C., for a time period in the range of about 1 hour to about 72 hours. The reaction may be carried out under conventional heating (using an oil bath) or under microwave irradiation. The reaction may be conducted either in an open vessel or in a sealed tube.

When K is and acyl halide group, for instance acyl chloride (e.g. K=COCl), compound (IV) is directly reacted with the alcohol (V), using known methods. The reaction may be promoted by a base such as triethylamine, pyridine, and 4-dimethylaminopyridine, and carried out in a suitable solvent (e.g. dichloromethane). This reaction is performed in a temperature range from about 0° C. to about 130° C. over a period of about 1 hour to about 74 hours. The reaction may be conducted under conventional heating (using an oil bath) or under microwave heating. The reaction may be carried out in an open vessel or in a sealed tube.

In some embodiments of the invention, the needed acyl halide (IV) may be readily prepared from the corresponding carboxylic acid (IV) wherein K=COOH. This activation may be affected according to one of the several standard procedures reported in the literature. They comprise, for instance, treatment of acid (IV) wherein K=COOH with one or more equivalents of oxalyl chloride in the presence of a catalytic amount of dimethylformamide (DMF) in a halocarbon solvent, such as dichloromethane, at temperature ranging from about 0° C. to about 35° C.

From all of the above, it is clear that alternative conventional synthetic pathways may be applied as well for the preparation of the compounds of formula (VI) from reactants (IV) and (V).

In particular, carboxylic derivatives of formula (IV) may be conveniently converted, in situ, into the corresponding acyl halides to be then reacted with alcohol (V). For example, alcohols (V) are reacted with acids (IV) wherein K=COOH in the presence of triphenylphosphine and a halocarbon solvent such as carbon tetrachloride or dichloromethane, at about RT, in a maximum period of time of 16 hours (Lee, J. B. *J. Am. Chem. Soc.*, 1966, 88, 3440, which is incorporated herein by reference in its entirety).

Alternatively, a compound of formula (IV) wherein K=COOH may be first activated with other commercially available activating agents such as, for instance, bromotripyrrolidinophosphonium hexafluorophosphate (PyBrOP) or carbonylimidazole, in a suitable aprotic solvent (e.g. dichloromethane, tetrahydrofuran), at about RT, to be then reacted with compound (V).

In addition, compounds of formula (VI) may also be efficiently prepared by the condensation between carboxylic acids (IV) alcohol (V) under typical Mitsunobu conditions (Kumara Swamy, K. C., *Chem. Rev.*, 2009, 109, 2551-2651, which is incorporated herein by reference in its entirety). For example, acid (IV) and alcohol (V) are reacted in the presence of a suitable phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from about 0° C. to about 100° C., for a time in the range of about 30 minutes to about 72 hours.

Alternatively, compounds of formula (VI) may be prepared according to route G. Compounds of general formula (XII) may be coupled to compounds of general formula (V) to yield compounds (XIII), according to known procedures. For instance, the conditions used to perform the coupling may be selected among those described to produce the coupling between compounds (IV) and (V) in Scheme 1.

In case W is a halide, the resulting intermediate (XIII) may then be used as the alkylating agent of amines of general formula (III) to furnish the desired intermediate (VI). This reaction may be performed under the typical conditions extensively reported in literature, such as those described to obtain compound (IV) by coupling (II) and (III) (Scheme 1).

In case W in compound (XII) is hydroxyl, it must be converted into a opportune leaving group selected from the group consisting of halide (i.e. bromine, iodine, chlorine) and sulfonate ester (i.e. tosylate, triflates, mesylate), according to known procedures (a general overview is given by Carey, F. A. and Sundeberg, R. J. *Advanced Organic Chemistry*, Third Edition (1990), Plenum Press, New York and London, chapter 3, 121, which is incorporated herein by reference in its entirety), before performing the coupling with amine (III). In case W is a suitably protecting hydroxyl group, it must be deprotected and activated as above before performing the coupling with amines (III).

Once obtained, the compounds of general formula (VI) can be obtained either as single diastereomer or as a mixture of diastereomers. For instance, in the case alcohol (V) has R configuration, corresponding compounds of formula (VI) can be obtained in both S—R configuration or R—R configuration, as well as a mixture of diastereomers (R—R and S—R configuration).

The mixture of diastereomers may be converted to compounds of formula (I) or can be most conveniently resolved to give the two single diastereomers which, in turn, may be converted to compounds of formula (I). This separation can be accomplished by using known procedures. These procedures include, but are not limited to, chromatography purification, preparative HPLC purification and crystallization. For example, the two diastereomers may be separated by flash chromatography on silica gel eluting with suitable solvents or with a mixture of solvents such as DCM and Methanol and the like. In another process of the present invention, separation of diastereomers may be carried out by using a column filled with a chiral stationary phase, for example Chiralpack AY or Chiralcel OD or Chiralcel OZ, and eluting, for example, with acetonitrile and/or with mixtures of acetonitrile and an alcohol. Alternatively, the separation of diastereomers may be most conveniently achieved by crystallization from an opportune solvent (e.g. ethyl ether), as a free base or after the formation of a suitable salt (e.g. (+)-tartaric acid)).

The compounds of formula (VI) are then alkylated with an agent of formula (XIV) to give compounds of formula (I).

This kind of reaction is largely described in literature under several different conditions, for instance, the reaction may be performed neat or in a suitable solvent selected from the group consisting of acetonitrile, DMF, DMSO, and tetrahydrofuran. The reaction typically proceeds at temperature range from 0° C. up to 170° C., for a time in the range of few minutes up to 72 hours. The reaction may be carried out under conventional heating (using an oil bath) or under microwave irradiation. The reaction may be conducted either in an open vessel or in a sealed tube.

Thus, any suitable moiety of $R_1$, $R_2$, $R_3$ and $R_6$ group in formula (I) could undergo a variety of reactions to afford other final compounds of formula (I).

Likewise, the optional salification of the compounds of formula (I) may be carried out by properly converting any of the free acidic groups (e.g. carboxylic) or free amino groups into the corresponding pharmaceutically acceptable salts.

In this case too, the operative conditions employed for the optional salification of the compounds of the invention are known.

As formerly reported, the compounds of formula (II) and (III) are known and, if not commercially available, may be readily prepared according to known methods.

In particular, compounds of formula (II) are commercially available or may be conveniently prepared according to standard procedures extensively reported in literature. For instance, compounds of general formula (II) in which LG is a halogen such as a bromine, may be prepared by halogenation of the suitably substituted phenyl acetic ester (for example following the procedure reported by Epstein, J. W. in *J. Med. Chem.*, 1981, 24/5, 481, which is incorporated herein by reference in its entirety). Alternatively, compounds of general formula (II) may be prepared starting from the appropriately substituted mandelic derivative, using known procedures (a survey of the suitable reactions is given by Larock, L. C., *Comprehensive Organic Transformation*, Second edition (1999), John Wiley & Son Inc, pg 689-700, which is incorporated herein by reference in its entirety).

From all of the above, it should be clear that the above process, comprehensive of any variant thereof for the preparation of suitable compounds of formula (I) of the invention, may be conveniently modified so as to adapt the reaction conditions to the specific needs, for instance by choosing appropriate condensing agents, solvents and protective groups.

More in particular, functional groups being present in any of the compounds of formula (II), (III), (IV), or (XIV) and which could give rise to unwanted side reactions and by-products, need to be properly protected before the condensation reaction takes place. Likewise, subsequent deprotection of those same protected groups may follow upon completion of the said reactions.

In the present invention, unless otherwise indicated, the term "protecting group", designates a protective group adapted to preserving the function of the group to which it is bound. Specifically, protective groups are used to preserve amino, hydroxyl or carboxyl functions. Appropriate protective groups may thus include, for example, benzyl, benzyloxycarbonyl, alkyl or benzyl esters, or other substituents commonly used for the protection of such functions, which are all well known [see, for a general reference, T. W. Green; *Protective Groups in Organic Synthesis* (Wiley, N.Y. 1981) which is incorporated herein by reference in its entirety].

The present invention also provides pharmaceutical compositions of compounds of general formula (I) in admixture with one or more pharmaceutically acceptable carriers, for example those described in *Remington's Pharmaceutical Sciences Handbook*, XVII Ed., Mack Pub., N.Y., U.S.A. which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various known pharmaceutically acceptable carriers, diluents (such as sucrose, mannitol, lactose, starches) and excipients, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering the compounds of the invention, including aqueous and non-aqueous solutions, emulsions, suspensions, syrups, and elixirs. Such dosage forms can also contain suitable known inert diluents such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable compositions include inhalable powders, propellant-containing metering aerosols or propellant-free inhalable formulations.

For administration as a dry powder, known single- or multi-dose inhalers may be utilized. In that case the powder may be filled in gelatin, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium, and they may be delivered by jet or ultrasonic nebulizers or by soft-mist nebulizers.

The compounds of the present invention may be administered as the sole active agent or in combination with other pharmaceutical active ingredients including those currently used in the treatment of respiratory disorders, e.g. beta2-agonists, corticosteroids, P38 MAP kinase inhibitors, IKK2, HNE inhibitors, PDE4 inhibitor, leukotriene modulators, NSAIDs, and mucus regulators.

The present invention also provides combinations of a compound of formula (I) with a β2-agonist selected from the group consisting of GSK-642444, indacaterol, milveterol, arformoterol, salbutamol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of formula (I) with a corticosteroid selected from the group consisting of propionate, ciclesonide, mometasone furoate, and budesonide.

The present invention also provides combinations of a compound of formula (I) with a P38 inhibitor selected from the group consisting of semapimod, talmapimod, pirfenidone, PH-797804, GSK-725, minokine, and losmapimod.

The present invention also provides combinations of a compound of formula (I) with a IKK2 inhibitor.

The present invention also provides combinations of a compound of formula (I) with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound of formula (I) with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TP1-PD3, ELB-353, CC-11050, GSK-256066, oglemilast, OX-914, tetomilast, MEM-1414, and RPL-554.

The present invention also provides combinations of a compound of consisting of montelukast, zafirlukast, and pranlukast.

The present invention also provides combinations of a compound of formula (I) with a NSAID selected from the group consisting of ibuprofen and ketoprofen.

The present invention also provides combinations of a compound of formula (I) with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage of 0.001 to 1000 mg/day, preferably 0.1 to 500 mg/day.

When the compounds of formula (I) are administered by inhalation route, they are preferably given at a dosage of 0.001 to 500 mg/day, preferably 0.1 to 200 mg/day.

The compounds of formula (I) may be administered for the prevention and/or treatment of any disease wherein M3 antagonists are active. Said disease include: diseases involving inflammation such as asthma and COPD, acute rhinitis; diseases involving the gastrointestinal tract such as peptic ulcer; diseases involving the cardiovascular system such as acute myocardial infarction; diseases involving the genitourinary tract such as renal colic; anticholinesterase and mushroom poisoning; uses in anesthesia; uses in ophthalmology. They also include neurological and psychiatric disorders such as Parkinsonism (Parkinson's disease) and motion sickness.

Preferably the compounds of formula (I) may be administered for the prevention and/or treatment of respiratory diseases such as from mild to acute severe conditions of asthma and COPD.

Other respiratory diseases include bronchitis, bronchiolitis, bronchiectasis, acute nasopharyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

Other features of the invention will become apparent in the course of the following descriptions of exemplary embodiments which are given for illustration of the invention and are not intended to be limiting thereof.

EXAMPLES

In the following examples:
I=intermediates
C=compounds.

Example 1

Preparation of (R)-quinuclidin-3-yl 2-phenyl-2-(phenylamino)-acetate (Diastereomers 1 and 2 of I2)

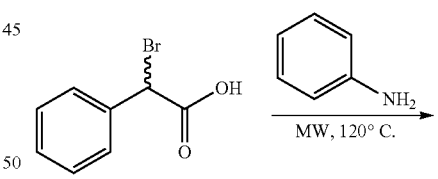

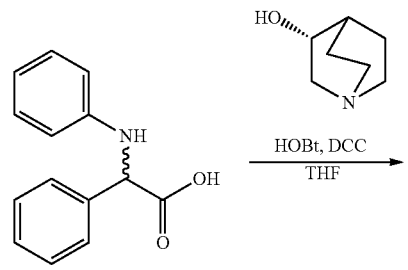

I1

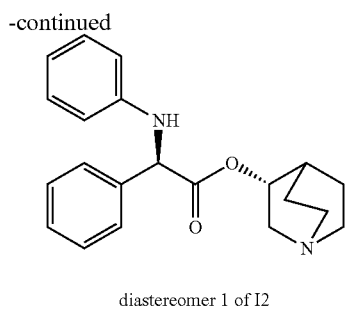

diastereomer 1 of I2

+

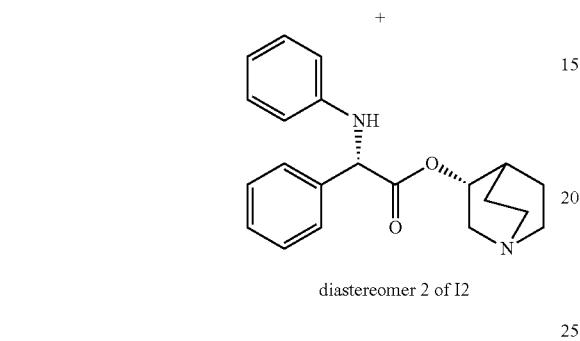

diastereomer 2 of I2

Preparation of 2-phenyl-2-(phenylamino)acetic acid (I1)

α-Bromophenylacetic acid (5.01 g, 23.2 mmol) was dissolved in aniline (25 ml, 274 mmol), and the mixture was reacted in a closed vessel under microwave irradiation at 120° C. for 5 minutes (UPLC-MS monitoring: complete conversion). Dichloromethane (DCM) (100 ml) was added to the reaction mixture, and the resulting solid was filtered; 2M $Na_2CO_3$ (50 ml) was added to the solution, and the aqueous layer was washed with DCM (3×100 ml). The aqueous layer was acidified with 12N HCl (36 ml) and the title compound was recovered as racemic mixture by filtration (5.1 g, 97% yield).

Preparation of (R)-quinuclidin-3-yl 2-phenyl-2-(phenylamino)-acetate (Diastereomers 1 and 2 of I2)

To a solution of 2-phenyl-2-(phenylamino)acetic acid (I1) (3.40 g, 14.9 mmol) in THF (600 ml), was added DCC (4.02 g, 19.4 mmol), HOBt (3.06 g, 19.4 mmol), and 3(R)-quinuclidinol (3.80 g, 29.9 mmol). The resulting mixture was stirred for 16 hours at room temperature (UPLC-MS monitoring: complete conversion). The solvent was evaporated, the residue was taken up with EtOAc, and the insoluble was eliminated by filtration. The clear solution was washed with 1M $K_2CO_3$ and then with brine, was dried over $Na_2SO_4$, filtered and evaporated to dryness. The resulting crude was purified by flash chromatography (DCM/MeOH=95/5, 0.1% $NH_3$ (aq.)) recovering first diastereomer 1 of I2 as a white solid (1.13 g, 22.5% yield, single diastereomer), and subsequently diastereomer 2 of I2 (0.69 g, 13.7% yield, single diastereomer).

Diastereomer 1 of I2:
$^1$H NMR (300 MHz, DMSO-$d_6$) ppm: 7.48-7.59 (m, 2H), 7.26-7.46 (m, 3H), 7.02-7.14 (m, 2H), 6.67-6.79 (m, 2H), 6.51-6.64 (m, 1H), 6.27 (d, 1H), 5.26 (d, 1H), 4.61-4.78 (m, 1H), 2.96 (ddd, 1H), 2.55-2.67 (m, 3H), 2.16-2.37 (m, 1H), 2.06 (d, 1H), 1.79-1.94 (m, 1H), 1.59-1.76 (m, 1H), 1.35-1.59 (m, 2H), 1.20-1.34 (m, 1H);
LC-MS (ESI POS): 337.04 (MH+).

Diastereomer 2 of I2:
$^1$H NMR (300 MHz, DMSO-$d_6$) ppm: 7.48-7.60 (m, 2H), 7.24-7.43 (m, 3H), 6.97-7.14 (m, 2H), 6.66-6.78 (m, 2H), 6.51-6.66 (m, 1H), 6.26 (d, 1H), 5.24 (d, 1H), 4.62-4.81 (m, 1H), 3.08 (ddd, 1H), 2.54-2.70 (m, 5H), 1.64-1.79 (m, 1H), 1.32-1.64 (m, 2H), 1.16-1.32 (m, 1H), 0.93-1.16 (m, 1H);
LC-MS (ESI POS): 337.04 (MH+).

Example 2

Preparation of (R)-quinuclidin-3-yl 2-(4-fluorophenyl)-2-(3-fluorophenylamino)acetate (I4)

Scheme 3

Preparation of 2-(4-fluorophenyl)-2-(3-fluorophenylamino)acetic acid (I3)

A mixture of 2-bromo-2-(4-fluorophenyl)acetic acid (500 mg, 2.15 mmol) and 3-fluoroaniline (477 mg, 4.29 mmol) in acetonitrile (8 ml) was heated under microwave irradiation at 100° C. for 50 minutes. Then 3-fluoroaniline (238 mg, 2.15 mmol) was added again, and the reaction mixture was heated at 120° C. for 45 minutes in a microwave oven (UPLC-MS monitoring: complete conversion). The organic solution was diluted with EtOAc and was washed with 2N HCl and then with brine. The organic phase was dried over $Na_2SO_4$, filtered and the solvent was evaporated to give 2-(4-fluorophenyl)-2-(3-fluorophenylamino)acetic acid (510 mg, 90% yield).

Preparation of (R)-quinuclidin-3-yl 2-(4-fluorophenyl)-2-(3-fluorophenylamino)acetate (I4)

A mixture of 2-(4-fluorophenyl)-2-(3-fluorophenylamino)acetic acid (I3) (510 mg, 1.94 mmol), (R)-quinuclidin-3-ol (246 mg, 1.94 mmol), HOBT (356 mg, 2.32 mmol), and DCC (480 mg, 2.32 mmol) in THF (10 ml) was stirred at room temperature overnight (UPLC-MS monitoring: complete conversion). The solvent was evaporated, the crude was dissolved in EtOAc, and the insoluble was removed by filtration. The clear solution was washed with 1N $K_2CO_3$ and then with brine. The organic layer was dried over $Na_2SO_4$, filtered and evaporated. The crude product was purified by silica gel chromatography (EtOAc/MeOH=8/2) to give (R)-quinuclidin-3-yl 2-(4-fluorophenyl)-2-(3-fluorophenylamino)acetate (360 mg, 50% yield, mixture of diastereomers).

$^1$H NMR (300 MHz, DMSO-$d_6$):
Diastereomer 1 of I4: 7.41-7.65 (m, 2H), 7.15-7.33 (m, 2H), 6.96-7.14 (m, 1H), 6.67 (d, 1H), 6.43-6.59 (m, 2H), 6.20-6.42 (m, 1H), 5.36 (d, 1H), 4.46-4.88 (m, 1H), 2.97 (ddd, 1H), 2.53-2.72 (m, 3H), 2.18-2.39 (m, 1H), 2.01-2.16 (m, 1H), 1.80-1.96 (m, 1H), 1.21-1.66 (m, 4H).
Diastereomer 2 of I4: 7.41-7.65 (m, 2H), 7.15-7.33 (m, 2H), 6.96-7.14 (m, 1H), 6.67 (d, 1H), 6.43-6.59 (m, 2H), 6.20-6.42 (m, 1H), 5.35 (d, 1H), 4.46-4.88 (m, 1H), 3.08 (ddd, 1H), 2.53-2.72 (m, 5H), 1.66-1.76 (m, 1H), 1.21-1.66 (m, 4H);
LC-MS (ESI POS): 373 (MH+).

Example 3

Preparation of (R)-quinuclidin-3-yl 2-((4-fluorophenyl)(methyl)amino)-2-phenylacetate (I7)

Preparation of ethyl 2-((4-fluorophenyl)(methyl)amino)-2-phenylacetate (I5)

4-Fluoro-N-methylaniline (0.33 g, 2.67 mmol) was added to a solution of ethyl 2-bromo-2-phenylacetate (0.36 ml, 2.06 mmol) in acetonitrile (6.86 ml) and DIPEA (0.47 ml, 2.67 mmol). The dark solution was stirred at 100° C. under microwave irradiation for 1 hour. Then solvent was evaporated and the crude was purified by flash chromatography (Petroleum ether/EtOAc=97/3) to obtain intermediate I5 (0.59 g, 100% yield).

Preparation of 2-((4-fluorophenyl)(methyl)amino)-2-phenylacetic acid hydrochloride (I6)

Ethyl 2-((4-fluorophenyl)(methyl)amino)-2-phenylacetate (I5) (0.59 g, 2.05 mmol) was dissolved in a mixture THF (10 ml) and water (10 ml), and lithium hydroxide hydrate (0.26 g, 6.14 mmol) was added. The reaction was stirred at room temperature for 3.5 hours and then at 70° C. for 24 hours. 3N HCl was added till pH was about 1, and the mixture was evaporated. Water (15 ml) was added, and the residue was triturated obtaining a pale brown suspension that was filtered on a buckner funnel washing with water and then with acetonitrile. The solid was dried under vacuum at 40° C. overnight to obtain intermediate I6 (0.44 g, 72% yield).

Preparation of (R)-quinuclidin-3-yl 2-((4-fluorophenyl)(methyl)-amino)-2-phenylacetate (I7)

PS-DCC (1.02 g, 1.35 mmol, loading: 1.33 mmol/g) was suspended in dry THF (13.5 ml). HOBT (0.21 g, 1.35 mmol), 2-((4-fluorophenyl)(methyl)amino)-2-phenylacetic acid hydrochloride (I6) (0.20 g, 0.68 mmol), and (R)-quinuclidin- Scheme 4

3-ol (0.26 g, 2.03 mmol) were added. The mixture was shaken at RT overnight. PS-DCC was removed by filtration, washed with EtOAc and THF. The solution was evaporated, and the residue was partitioned between EtOAc and water. The organic phase was washed with saturated $NaHCO_3$, dried with $Na_2SO_4$, and evaporated. The crude was purified by flash chromatography (DCM/MeOH=95/5) to afford the title compound (209 mg, 84% yield, mixture of diastereomers).

$^1$H NMR (300 MHz, DMSO-$d_6$) ppm: 7.26-7.49 (m, 5H) 6.99-7.13 (m, 2H) 6.83-6.99 (m, 2H) 5.78 (d, 1H) 4.74-4.88 (m, 1H) 3.02-3.18 (m, 2H) 2.56-2.79 (m, 5H) 2.29-2.46 (m, 2H) 1.76-1.93 (m, 1H) 1.41-1.63 (m, 3H) 1.19-1.39 (m, 1H);

LC-MS (ESI POS): 369.2 (MH+).

Example 4

Preparation of (R)-quinuclidin-3-yl 2-(3-(methylcarbamoyl)-phenylamino)-2-phenylacetate (I10)

C. for 60 minutes (UPLC-MS: complete conversion). Acetonitrile was evaporated, and the crude residue was purified by flash chromatography (DCM/EtOAc=8/2) to obtain ethyl 2-(3-(methylcarbamoyl)phenylamino)-2-phenylacetate (475 mg, 92% yield).

Preparation of 2-(3-(methylcarbamoyl)phenylamino)-2-phenylacetic acid hydrochloride (I9)

Ethyl 2-(3-(methylcarbamoyl)phenylamino)-2-phenylacetate (I8) (475 mg, 1.52 mmol) and lithium hydroxide hydrate (128 mg, 3.04 mmol) were dissolved in THF (7 ml) and water (3 ml), and the resulting homogeneous yellow solution was stirred at room temperature for 2 hours (UPLC-MS: complete conversion). THF was evaporated, and the resulting colorless clear solution was cooled at 0° C. and treated with 1N HCl until pH about 1. The solid was recovered by filtration under suction, washed with cooled water and dried under vacuum

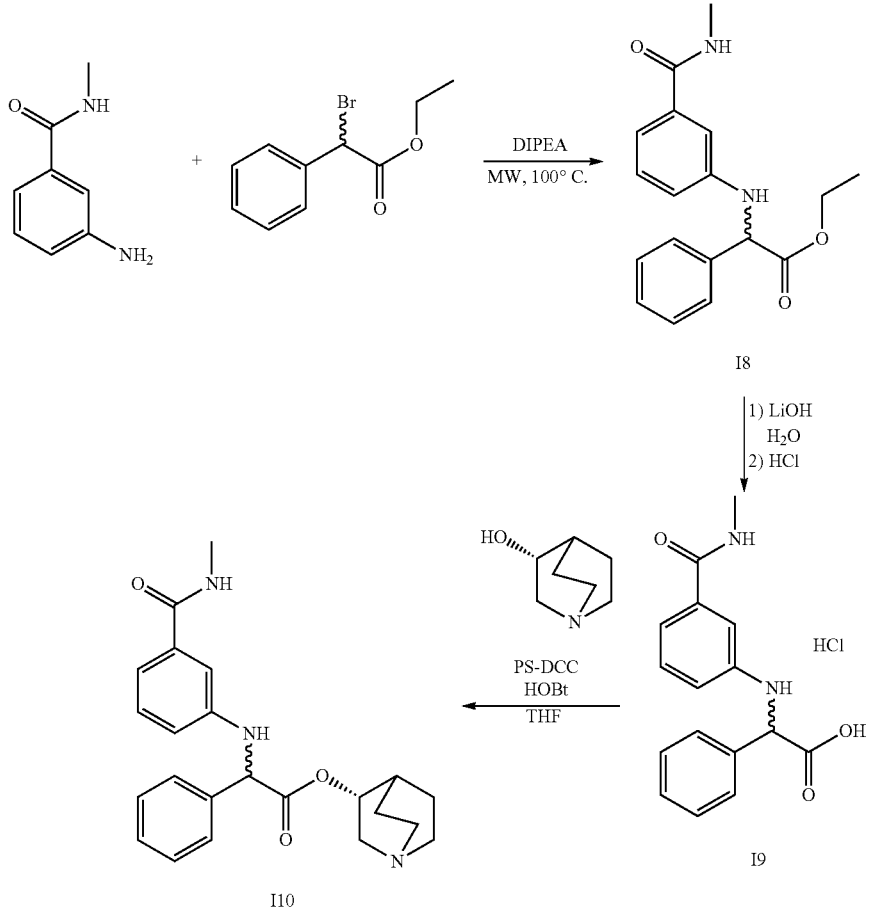

Scheme 5

Preparation of ethyl 2-(3-(methylcarbamoyl)phenylamino)-2-phenylacetate (I8)

3-Amino-N-methylbenzamide (371 mg, 2.47 mmol), ethyl 2-bromo-2-phenylacetate (0.29 ml, 1.64 mmol), and DIPEA (0.43 ml, 2.47 mmol) were dissolved in acetonitrile (5 ml) and stirred under microwave irradiation into a sealed vial at 100° overnight to obtain 2-(3-(methylcarbamoyl)phenylamino)-2-phenylacetic acid hydrochloride (418 mg, 86% yield).

Preparation of (R)-quinuclidin-3-yl 2-(3-(methylcarbamoyl)-phenylamino)-2-phenylacetate (I10)

PS-DCC (798 mg, 0.998 mmol, loading: 1.25 mmol/g) was suspended in dry THF (10 ml). 2-(3-(Methylcarbamoyl)phenylamino)-2-phenylacetic acid hydrochloride (I9) (160 mg, 0.50 mmol), HOBT (153 mg, 0.10 mmol), and (R)-quinuclidin-3-ol (190 mg, 1.50 mmol) were added, and the mixture was shaken at room temperature for 16 hours (UPLC-MS: complete conversion). PS-DCC was removed by filtration and washed with THF and EtOAc. The filtrate was evaporated and the resulting residue was dissolved in EtOAc and washed with NaHCO$_3$, water and brine. The organic layer was separated, dried over Na$_2$SO$_4$, filtered and evaporated. The resulting oil (196 mg, quantitative yield, mixture of diastereomers) was used for the next step without any further purification.

$^1$H NMR (300 MHz, DMSO-d$_6$) ppm: 8.17 (q, 1H), 7.48-7.59 (m, 2H), 7.25-7.48 (m, 3H), 7.17-7.23 (m, 1H), 7.13 (t, 1H), 6.99-7.08 (m, 1H), 6.80-6.94 (m, 1H), 6.49 (d, 1H), 5.32 (d, 1H), 4.59-4.79 (m, 1H), 2.89-3.15 (m, 1H), 2.74 (d, 3H), 2.54-2.68 (m, 5H), 1.07-1.96 (m, 5H);

LC-MS (ESI POS): 394.2 (MH+).

Example 5

Preparation of (R)-quinuclidin-3-yl 2-(4-chlorophenylamino)-2-phenylacetate (I12)

Scheme 6

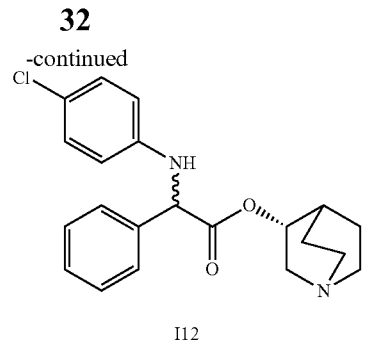

Preparation of 2-(4-chlorophenylamino)-2-phenylacetic acid (I11)

To a solution of α-bromophenylacetic acid (1.00 g, 4.65 mmol) in acetonitrile (20 ml), was added 4-chloro-phenylamine (1.18 g, 9.30 mmol), and the mixture was heated under microwave irradiation at 100° C. for 1 hour (UPLC-MS monitoring: complete conversion). The solvent was evaporated, and the residue was positioned between EtOAc and 1N HCl. The organic phase was dried over Na$_2$SO$_4$, filtered and evaporated to dryness to obtain intermediate I11 (0.57 g; 47% yield).

Preparation of (R)-quinuclidin-3-yl 2-(4-chlorophenylamino)-2-phenylacetate (I12)

To a solution of 2-(4-chlorophenylamino)-2-phenylacetic acid (I11) (574 mg, 2.20 mmol) in dry THF (20 ml), were added DCC (543 mg, 2.64 mmol), HOBt (359 mg, 2.64 mmol), and 3(R)-quinuclidinol (558 mg, 4.40 mmol). The resulting mixture was stirred at RT overnight (UPLC-MS monitoring: complete conversion). The solvent was evaporated, and the residue was partitioned between EtOAc and 2M K$_2$CO$_3$. The organic phase was dried over Na$_2$SO$_4$, filtered and evaporated to dryness. The resulting crude was purified by flash chromatography (DCM/MeOH=99/1 to 85/15) to obtain the title compound (306 mg, 37% yield, mixture of diastereomers).

$^1$H NMR (300 MHz, DMSO-d$_6$) ppm: 7.46-7.59 (m, 2H), 7.22-7.45 (m, 3H), 6.99-7.18 (m, 2H), 6.65-6.80 (m, 2H), 6.52 (d, 1H), 5.28 (d, 1H), 4.60-4.82 (m, 1H), 3.04 (ddd, 1H), 2.54-2.70 (m, 4H), 2.03-2.36 (m, 1H), 1.67-1.97 (m, 1H), 1.36-1.68 (m, 2H), 1.05-1.35 (m, 2H);

LC-MS (ESI POS): 371.1 (MH+).

The compounds listed in Table 1 were obtained as previously described for I12, starting from the suitable commercially available 2-bromo-phenylacetic acid derivatives and anilines.

TABLE 1

| Compound | Structure | Yield | Analytical |
|---|---|---|---|
| I13 | (structure: phenyl-NH-CH(4-F-phenyl)-C(=O)-O-quinuclidine, Mixture of diastereomer) | 11% | LC-MS (ESI POS): 355.2 (MH+)<br>$^1$H NMR (300 MHz, DMSO-d$_6$) ppm: 7.36-7.66 (m, 2 H), 7.15-7.28 (m, 2 H), 7.00-7.12 (m, 2 H), 6.64-6.81 (m, 2 H), 6.50-6.64 (m, 1 H), 6.29 (d, 1 H), 5.29 (d, 1 H), 4.39-4.82 (m, 1 H), 3.01-3.12 (m, 1 H), 2.53-2.69 (m, 5 H), 1.67-1.80 (m, 1 H), 0.97-1.58 (m, 4 H) |

TABLE 1-continued

| Compound | Structure | Yield | Analytical |
|---|---|---|---|
| 114 | Mixture of diastereomer | 9% | LC-MS (ESI POS): 395.1 (MH+)<br>$^1$H NMR (300 MHz, DMSO-d6) ppm: 7.68 (m, 2 H), 7.47-7.58 (m, 2 H), 7.23-7.47 (m, 3 H), 7.15 (d, 1 H), 6.62-6.80 (m, 2 H), 5.39 (d, 1 H), 4.75 (ddd, 1 H), 3.74 (s, 3 H), 2.86-3.19 (m, 1 H), 2.54-2.69 (m, 4 H), 1.84-2.26 (m, 1 H), 1.35-1.80 (m, 3 H), 0.99-1.34 (m, 2 H) |

Example 6

Preparation of (R)-quinuclidin-3-yl 2-(3-fluorophenyl)-2-(phenylamino)acetate (I18)

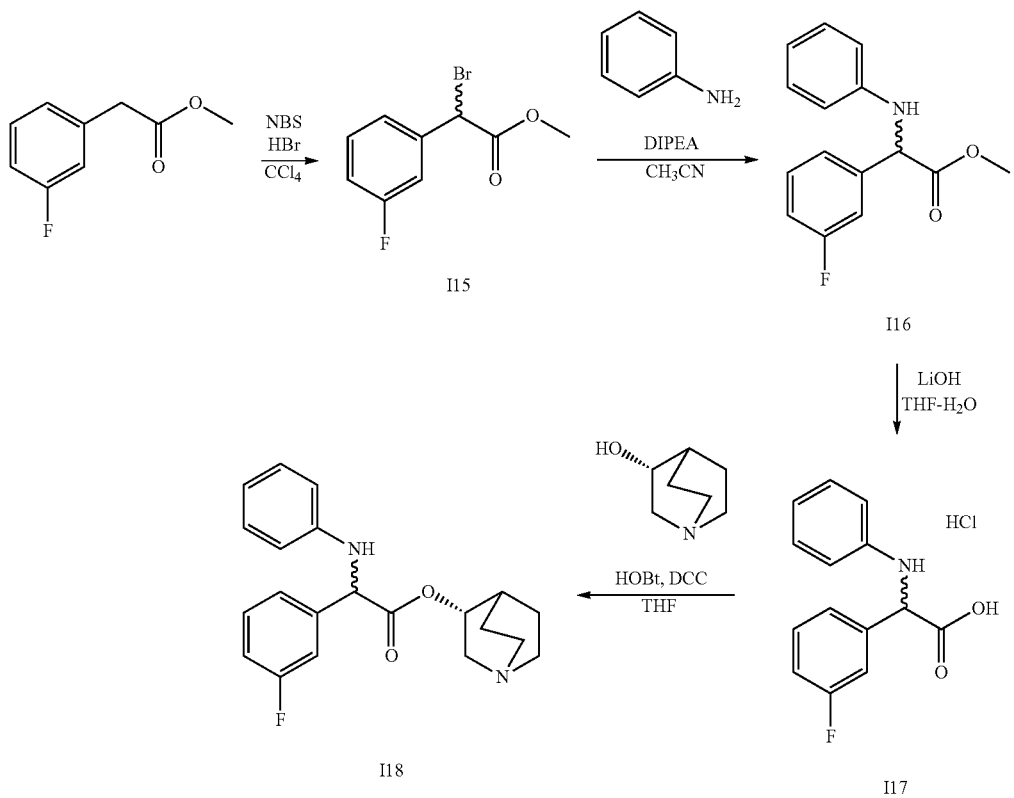

Scheme 7

Preparation of methyl 2-bromo-2-(3-fluorophenyl)acetate (I15)

Methyl 2-(3-fluorophenyl)acetate (1.90 g, 11.3 mmol) and N-bromo succinimide (2.01 g, 11.3 mmol) were dissolved in CCl$_4$ (80 ml). HBr (64 ul, 0.56 mmol) was added, and the mixture was stirred under reflux overnight. The mixture was cooled at room temperature, diluted with DCM, and washed with sat. NaHCO$_3$, water and brine. The organic layer was dried (Na2SO4), filtered, and evaporated obtaining intermediate I15 (2.68 g, 96% yield).

Preparation of methyl 2-(3-fluorophenyl)-2-(phenylamino)acetate (I16)

Methyl 2-bromo-2-(3-fluorophenyl)acetate (I15) (300 mg, 1.21 mmol), DIPEA (0.32 ml, 1.82 mmol), and aniline (0.17 ml, 1.82 mmol) were dissolved in acetonitrile (4 ml) and heated under microwave irradiation at 100° C. for 1 hour. Acetonitrile was evaporated, and the residue was purified by flash chromatography (Petroleum ether/EtOAc=95/5) to obtain intermediate I16 (229 mg, 73% yield).

Preparation of 2-(3-fluorophenyl)-2-(phenylamino)acetic acid hydrochloride (I17)

Methyl 2-(3-fluorophenyl)-2-(phenylamino)acetate (I16) (229 mg, 0.88 mmol) and lithium hydroxide hydrate (74.1 mg, 1.77 mmol) were dissolved in THF/water (6 ml/2 ml) and stirred at room temperature for 2 hour. THF was evaporated, the resulting basic aqueous solution was acidified at pH 1 with 1N HCl, and the precipitate was recovered by suction filtration and washed with 1N HCl. The compound was dried at 40° C. under vacuum overnight to obtain intermediate I17 (186 mg, 75% yield).

Preparation of (R)-quinuclidin-3-yl 2-(3-fluorophenyl)-2-(phenylamino)acetate (I18)

PS-DCC (982 mg, 1.31 mmol, loading: 1.33 mmol/g) was suspended in dry THF (15 ml). 2-(3-Fluorophenyl)-2-(phenylamino)acetic acid hydrochloride (I17) (184 mg, 0.65 mmol), HOBT (200 mg, 1.31 mmol), and (R)-quinuclidin-3-ol (249 mg, 1.96 mmol) were added, and the mixture was shaken at room temperature overnight. PS-DCC was removed by filtration, and the filtrate is evaporated. The residue was dissolved in EtOAc and washed with NaHCO$_3$, water and brine. The organic layer was dried over Na$_2$SO$_4$, filtered, and evaporated to dryness. The crude compound was purified by filtration through a pad of silica-gel using DCM/MeOH=9/1 as the eluent. The title compound was obtained (129 mg, 56% yield, mixture of diastereomers).

$^1$H NMR (300 MHz, DMSO-d$_6$) ppm: 7.31-7.52 (m, 3H), 7.11-7.23 (m, 1H), 6.98-7.11 (m, 2H), 6.67-6.76 (m, 2H), 6.51-6.63 (m, 1H), 6.35 (d, 1H), 5.35 and 5.36 (d, 1H), 4.59-4.80 (m, 1H), 2.97 and 3.07 (ddd, 1H), 2.55-2.67 (m, 5H), 1.67-1.74 and 1.81-1.95 (m, 1H), 1.10-1.66 (m, 4H);

LC-MS (ESI POS): 355.2 (MH+).

Example 7

Preparation of (R)-quinuclidin-3-yl 2-(2,5-difluorophenylamino)-2-phenylacetate (I21)

Scheme 8

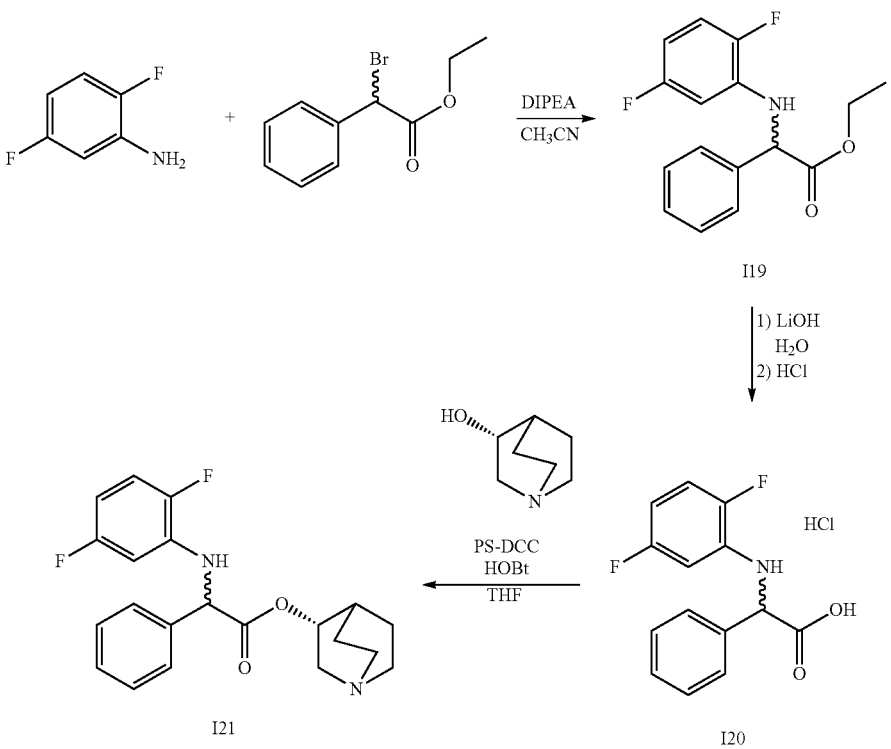

Preparation of ethyl 2-(2,5-difluorophenylamino)-2-phenylacetate (I19)

2,5-Difluoroaniline (0.19 ml, 1.85 mmol), ethyl 2-bromo-2-phenylacetate (0.22 ml, 1.23 mmol), and DIPEA (0.32 ml, 1.85 mmol) were dissolved in acetonitrile (3 ml) and heated under MW irradiation at 100° C. for 6 hours and then at 110° C. for 4 hours. Acetonitrile was evaporated, and the crude product was purified by flash chromatography (Petroleum ether/EtOAc=97/3) to obtain intermediate I19 (240 mg, 67% yield).

Preparation of 2-(2,5-difluorophenylamino)-2-phenylacetic acid hydrochloride (I20)

Ethyl 2-(2,5-difluorophenylamino)-2-phenylacetate (I19) (240 mg, 0.82 mmol) was dissolved in THF/water (7/3 ml). Lithium hydroxide hydrate (69.1 mg, 1.65 mmol) was added, and the resulting mixture was stirred at room temperature for 16 hours. THF was evaporated under reduced pressure, the solution was cooled at 0° C., and 1N HCl was added dropwise until pH 1. The white solid was recovered by filtration, washed with cold water and dried under vacuum at 40° C. overnight to obtain intermediate I20 (198 mg, 80% yield).

Preparation of (R)-quinuclidin-3-yl 2-(2,5-difluorophenylamino)-2-phenylacetate (I21)

PS-DCC (914 mg, 1.301 mmol, loading: 1.33 mmol/g) was suspended in dry THF (15 ml). 2-(2,5-Difluorophenylamino)-2-phenylacetic acid hydrochloride (I20) (195 mg, 0.65 mmol), HOBT (199 mg, 1.30 mmol), and (R)-quinuclidin-3-ol (248 mg, 1.95 mmol) were added, and the suspension was shaken at RT for 16 hours (Conversion complete by UPLC-MS). PS-DCC was removed by filtration under suction, and the filtrate was evaporated. The resulting residue was dissolved in EtOAc and washed with sat. NaHCO₃, water and brine. The organic layer was separated, dried over Na₂SO₄, filtered and evaporated. The crude was purified by filtration through a silica-pad using DCM/MeOH=95/5 as the eluent. The title compound is collected (195 mg, 80% yield, mixture of diastereomers).

$^1$H NMR (300 MHz, DMSO-d$_6$) ppm: 7.49-7.62 (m, 2H) 7.28-7.47 (m, 3H) 7.02-7.15 (m, 1H) 6.46-6.60 (m, 1H) 6.32-6.46 (m, 1H) 5.85-6.00 (m, 1H) 5.43 and 5.45 (d, 1H) 4.66-4.82 (m, 1H) 2.99 and 3.09 (ddd, 1H) 2.54-2.69 (m, 4H) 2.01-2.31 (m, 1H) 1.85-1.96 and 1.65-1.75 (m, 1H) 0.92-1.66 (m, 4H);

LC-MS (ESI POS): 373.2 (MH+).

Example 8

Preparation of (R)-quinuclidin-3-yl 2-phenyl-2-(o-tolylamino)acetate (I23)

Scheme 9

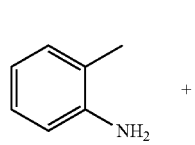
+
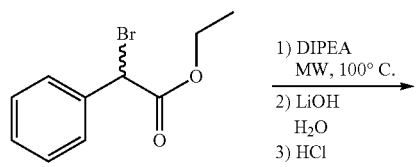
1) DIPEA MW, 100° C.
2) LiOH H₂O
3) HCl

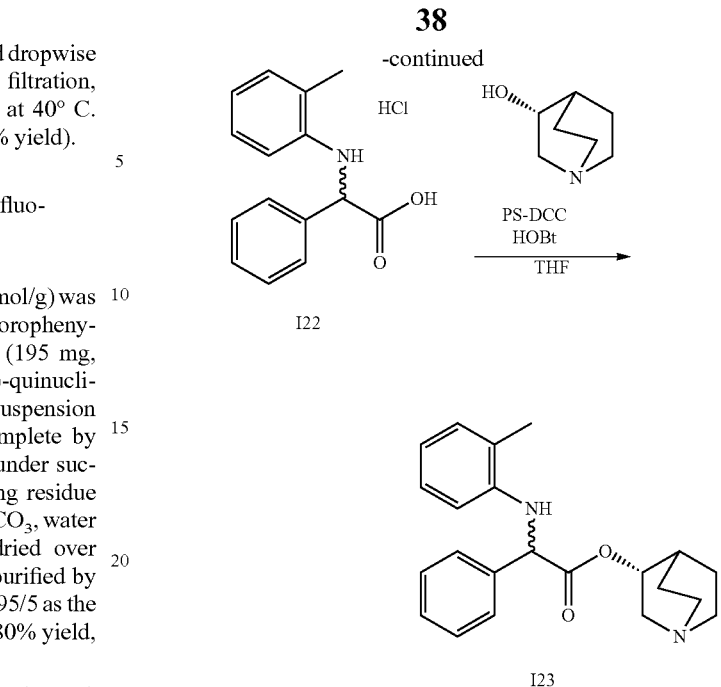

Preparation of 2-phenyl-2-(o-tolylamino)acetic acid hydrochloride (I22)

Ethyl 2-bromo-2-phenylacetate (0.28 ml, 1.64 mmol), ortho-toluidine (0.26 ml, 2.47 mmol), and DIPEA (0.43 ml, 2.47 mmol) were dissolved in acetonitrile (5 ml) and stirred under microwave irradiation at 100° C. for 1 hours (Conversion complete by UPLC/MS-UV). Lithium hydroxide hydrate (207 mg, 4.94 mmol) and water (3 ml) were added, and the mixture was stirred at room temperature for 16 hours. 4M HCl in dioxane was added until pH was about 1, then the solvents were evaporated, the residue was suspended in water, sonicated, and cooled at 0° C., and the resulting solid was recovered by filtration and dried under vacuum to get intermediate I22 (290 mg, 63% yield).

Preparation of (R)-quinuclidin-3-yl 2-phenyl-2-(o-tolylamino)-acetate (I23)

PS-DCC (1.15 g, 1.44 mmol, loading: 1.25 mmol/g) was suspended in THF (15 ml). 2-Phenyl-2-(o-tolylamino)acetic acid hydrochloride (I22) (200 mg, 0.72 mmol) and HOBT (221 mg, 1.44 mmol) were added, followed by (R)-quinuclidin-3-ol (275 mg, 2.16 mmol), and the mixture was stirred for 16 hours at room temperature. PS-DCC was removed by filtration, and the filtrate was evaporated. The resulting residue was dissolved in EtOAc and washed sequentially with water, sat. NaHCO₃, water and brine. The organic layer was dried over Na₂SO₄, filtered and evaporated to give the title compound (260 mg, quantitative yield, mixture of diastereomers).

$^1$H NMR (300 MHz, DMSO-d$_6$) ppm: 7.50-7.62 (m, 2H), 7.25-7.46 (m, 3H), 7.00-7.07 (m, 1H), 6.82-6.98 (m, 1H), 6.51-6.66 (m, 1H), 6.30-6.49 (m, 1H), 5.32 (d, 1H), 5.10 (d, 1H), 4.65-4.85 (m, 1H), 2.85-3.16 (m, 1H), 2.56-2.69 (m, 3H), 2.23 (s, 3H), 2.13-2.46 (m, 2H), 0.95-1.97 (m, 5H);

LC-MS (ESI POS): 351.2 (MH+).

Example 9

Preparation of (R)-quinuclidin-3-yl 2-(benzylamino)-2-phenylacetate (I25)

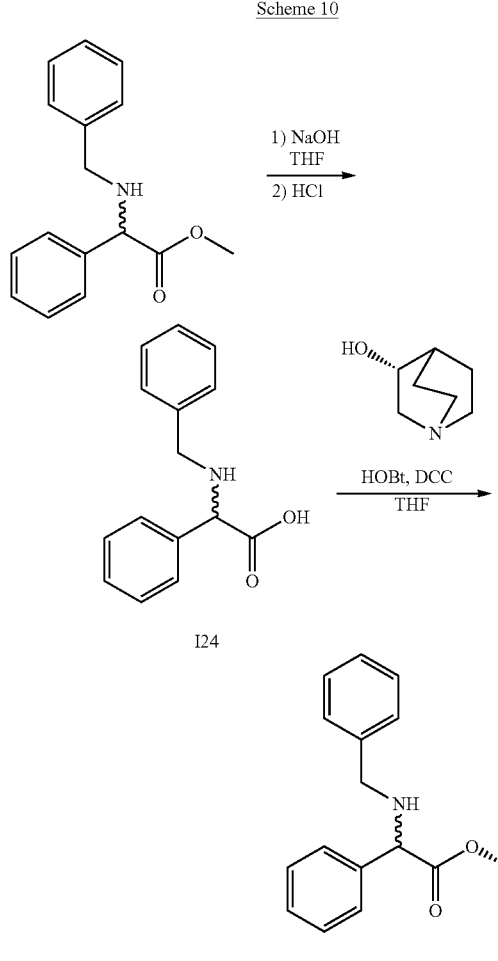

Scheme 10

Preparation of 2-(benzylamino)-2-phenylacetic acid (I24)

A solution of methyl 2-(benzylamino)-2-phenylacetate (1.00 g, 3.90 mmol) in THF (90 ml) and 1N NaOH (10 ml) was stirred at room temperature overnight (LC-MS monitoring: complete conversion). The solvent was removed under reduced pressure, and the crude product was partitioned between EtOAc and water. The aqueous phase was acidified with conc. HCl (pH about 3) and then extracted with EtOAc (three times). The organic phase was dried over $Na_2SO_4$, filtered and evaporated to dryness to give the title compound as a white solid (940 mg, quantitative yield), which is used in the next step without any further purification.

Preparation of (R)-quinuclidin-3-yl 2-(benzylamino)-2-phenylacetate (I25)

A mixture of 2-(benzylamino)-2-phenylacetic acid (I24) (0.94 g, 3.90 mmol), DCC (0.97 g, 4.70 mmol), HOBt (0.63 g, 4.07 mmol) and 3(R)-quinuclidinol (1.51 g, 11.7 mmol) in dry THF (30 ml) was stirred at room temperature overnight under nitrogen flowstream (LC-MS monitoring: complete conversion). The solvent was evaporated, and the residue was taken up with EtOAc and washed twice with water. The organic phase was dried over $Na_2SO_4$, filtered and evaporated to dryness. The resulting crude was purified by flash chromatography (DCM/MeOH-98/2, 0.2% $NH_{3(aq.)}$ to 95/5, 0.5% $NH_{3(aq.)}$) to give I25 (231 mg, 52% yield, mixture of diastereomers).

$^1$H NMR (300 MHz, DMSO-$d_6$+$Na_2CO_3$) ppm: 7.20-7.45 (m, 11H), 4.55-4.79 (m, 1H), 4.35 (s, 1H), 3.67 (d, 2H), 2.85-3.14 (m, 2H), 2.56-2.71 (m, 2H), 2.31-2.46 (m, 1H), 2.07-2.23 (m, 1H), 1.82-1.93 (m, 1H), 1.32-1.79 (m, 4H);

LC-MS (ESI POS): 351.2 (MH+).

Example 10

Preparation of (R)-quinuclidin-3-yl 2-(phenylamino)-2-(thiophen-2-yl)acetate (I30)

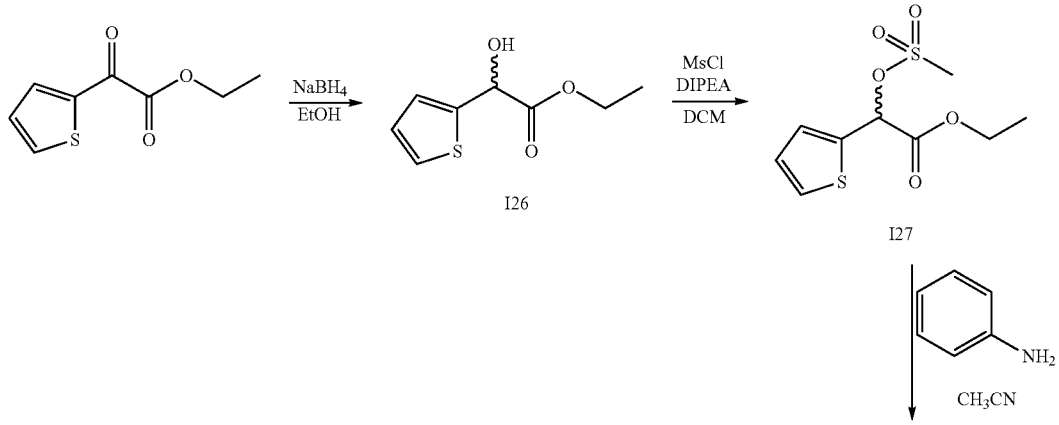

Scheme 11

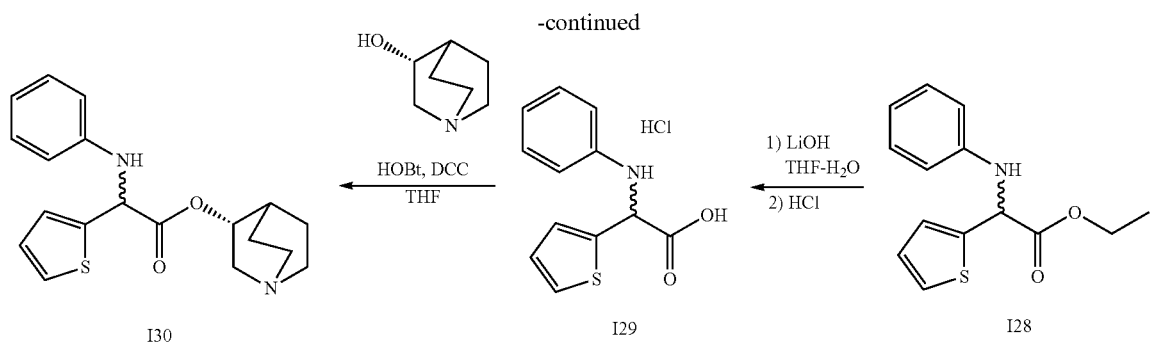

Preparation of ethyl 2-hydroxy-2-(thiophen-2-yl)acetate (I26)

A solution of ethyl 2-oxo-2-(thiophen-2-yl)acetate (5.00 g, 27.1 mmol) in ethanol (50 ml) was cooled at 0° C. with an ice bath. NaBH$_4$ (0.31 g, 8.14 mmol) was added in four portions under stirring. The mixture was stirred at 0° C. for 10 minutes, then allowed to warm at room temperature and stirred for additional 30 minutes. The reaction mixture was concentrated under vacuum and the residue was partitioned between Et$_2$O and ice-cooled water. The organic layer was separated, washed with water and brine, dried over Na$_2$SO$_4$, filtered and evaporated (5.05 g, 91% yield).

Preparation of ethyl 2-(methylsulfonyloxy)-2-(thiophen-2-yl)acetate (I27)

Ethyl 2-hydroxy-2-(thiophen-2-yl)acetate (I26) (4.58 g, 24.6 mmol) was dissolved in dry DCM (125 ml) and cooled at 0° C. DIPEA (5.15 ml, 29.5 mmol) and methanesulphonyl chloride (2.11 ml, 27.1 mmol) were added, and the resulting solution was stirred at room temperature for 1 hour. DIPEA (0.86 ml, 4.92 mmol) and methanesulphonyl chloride (0.19 ml, 2.46 mmol) were added again. After 1 additional hour, a third portion of DIPEA (0.43 ml, 2.46 mmol) and methanesulphonyl chloride (77 ul, 0.98 mmol) was added. After 1 hour, the reaction was completed. The mixture was diluted with DCM, washed with sat. NaHCO$_3$, water and brine, dried (Na$_2$SO$_4$), filtered, and evaporated. The resulting oil was used for the next step without any further purification.

Preparation of ethyl 2-(phenylamino)-2-(thiophen-2-yl)acetate (I28)

Ethyl 2-(methylsulfonyloxy)-2-(thiophen-2-yl)acetate (I27) (5.7 g, 21.6 mmol), aniline (2.16 ml, 23.7 mmol) and DIPEA (4.52 ml, 25.9 mmol) were dissolved in acetonitrile (20 ml) to give a yellow solution which was heated under microwave irradiation into a sealed vial at 100° C. for 15 minutes. Conversion complete by UPLC/MS-UV. The solvent was evaporated, and the residue was dissolved in DCM and washed with water and brine, dried (Na$_2$SO$_4$), filtered and evaporated to dryness. The resulting crude was purified by flash chromatography (Petroleum ether/EtOAc=85/15) to get desired compound as a solid (4.33 g, 77% yield).

Preparation of 2-(phenylamino)-2-(thiophen-2-yl) acetic acid hydrochloride (I29)

Ethyl 2-(phenylamino)-2-(thiophen-2-yl)acetate (I28) (3.86 g, 14.8 mmol) and lithium hydroxide hydrate (1.24 g, 29.5 mmol) were dissolved in THF/water (20 ml/20 ml) and stirred at room temperature for 4 hours. THF was evaporated, the mixture was cooled to 0° C., and 4M HCl in dioxane was added until pH is about 1. The resulting precipitate was collected by suction filtration and washed with water. The solid was dried under vacuum at 40° C. for 18 h (3.09 g, 78% yield).

Preparation of (R)-quinuclidin-3-yl 2-(phenylamino)-2-(thiophen-2-yl)acetate (I30)

2-(Phenylamino)-2-(thiophen-2-yl)acetic acid hydrochloride (I29) (359 mg, 1.33 mmol), DCC (330 mg, 1.60 mmol), and HOBT (245 mg, 1.60 mmol) were dissolved in THF (15 ml). (R)-quinuclidin-3-ol (339 mg, 2.66 mmol) was added, and the reaction mixture was stirred at room temperature for 16 hours. HOBT (20.4 mg, 0.13 mmol) and DCC (33.0 mg, 0.16 mmol) were added again and the mixture was stirred for additional 8 hours. HOBT (20.4 mg, 0.13 mmol), DCC (33.0 mg, 0.16 mmol), (R)-quinuclidin-3-ol (16.9 mg, 0.13 mmol) were added, and the mixture is stirred for additional 16 hours. THF is evaporated, and the resulting crude oil was dissolved in EtOAc and washed with water and brine. The organic phase was recovered, dried over Na$_2$SO$_4$, filtered and evaporated. The crude was first purified by flash chromatography (DCM/MeOH=9/1) and then by preparative HPLC. The pure fractions were collected and evaporated. The resulting TFA salt was dissolved in THF and passed through a PL-HCO3 cartridge (Varian, 200 mg, 1.8 mmol/g HCO3$^-$). THF was evaporated, and the product was dissolved in dioxane (2 ml) and 4M HCl in dioxane (2 ml) was added. The solvent was evaporated, and the residue was dried under vacuum for 24 hours to obtain the title compound (33 mg, 7% yield, mixture of diastereomers).

$^1$H NMR (300 MHz, DMSO-d$_6$) ppm: 10.01 (br. s., 1H) 7.47-7.56 (m, 1H) 7.21-7.29 (m, 1H) 6.99-7.16 (m, 3H) 6.71-6.82 (m, 2H) 6.53-6.70 (m, 1H) 5.64 and 5.61 (s, 1H) 4.99-5.13 (m, 1H) 3.03-3.28 (m, 4H) 2.71-2.92 (m, 2H) 1.42-2.28 (m, 5H);

LC-MS (ESI POS): 343.1 (MH+).

Example 11

Preparation of methyl 3-(1-(6-methoxypyridin-3-yl)-2-oxo-2-((R)-quinuclidin-3-yloxy)ethylamino)thiophene-2-carboxylate (I32)

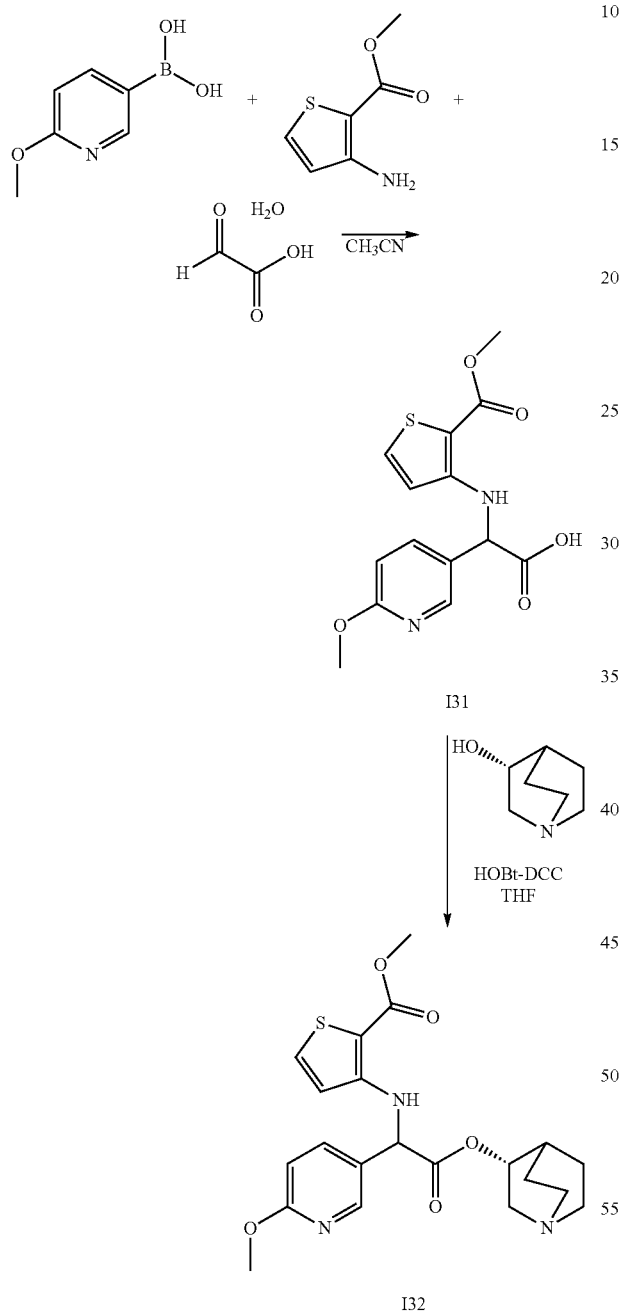

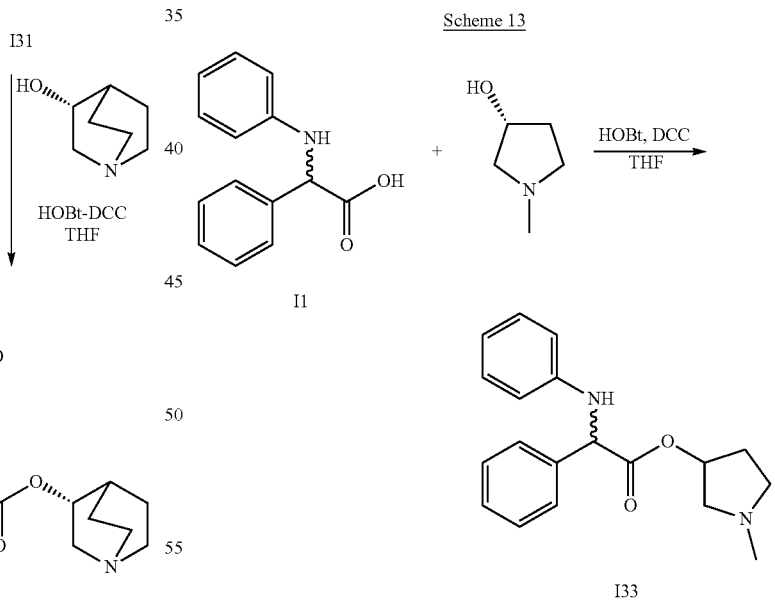

Preparation of 2-(2-(methoxycarbonyl)thiophen-3-ylamino)-2-(6-methoxypyridin-3-yl)acetic acid (I31)

To a suspension of 2-oxoacetic acid hydrate (156 mg, 1.70 mmol) and methyl 3-aminothiophene-2-carboxylate (267 mg, 1.70 mmol) in acetonitrile (15 ml), was added 6-methoxypyridin-3-ylboronic acid (260 mg, 1.70 mmol). The reaction was refluxed for 2 hours, and the solvent was evaporated to obtain 2-(2-(methoxycarbonyl)thiophen-3-ylamino)-2-(6-methoxypyridin-3-yl)acetic acid (548 mg, 100% yield). The product was used for the next step without any further purification.

Preparation of methyl 3-(1-(6-methoxypyridin-3-yl)-2-oxo-2-((R)-quinuclidin-3-yloxy)ethylamino)thiophene-2-carboxylate (I32)

To a solution of 2-(2-(methoxycarbonyl)thiophen-3-ylamino)-2-(6-methoxypyridin-3-yl)acetic acid (I31) (548 mg, 1.70 mmol) in THF (20 ml), were added N,N'-methanediylidenedicyclohexanamine (421 mg, 2.04 mmol), 1H-benzo[d][1,2,3]triazol-1-ol (276 mg, 2.04 mmol) and (R)-quinuclidin-3-ol (259 mg, 2.04 mmol). The reaction was stirred at room temperature for 15 hours, and then the solvent was evaporated. The residue was taken up with DCM, and the insoluble was removed by filtration. The organic phase was washed twice with $Na_2CO_3$ and then brine, dried over $Na_2SO_4$, filtered, and evaporated. The resulting yellow gummy crude was purified by flash chromatography (DCM/MeOH=95/5) collecting first diastereomer 1 of I32 (140 mg, 19% yield) and then a mixture of diastereomers 1 and 2 of I32 (100 mg, 14% yield).

Example 12

Preparation of (R)-1-methylpyrrolidin-4-yl-2-phenyl-2-(phenylamino)acetate (C14)

A mixture of 2-phenyl-2-(phenylamino)acetic acid (I1) (200 mg, 0.88 mmol), DCC (218 mg, 1.05 mmol), HOBt (142 mg, 1.05 mmol), and (R)-1-methylpyrrolidin-3-ol (289 uL, 2.64 mmol) in dry THF (10 mL) was stirred at room temperature overnight under nitrogen flowstream (LC-MS monitoring: complete conversion). The solvent was evaporated and the residue was taken up with aq. HCl (pH about 2) and washed with DCM. The aqueous phase was basified with $NaHCO_3$ and extracted with DCM (three times). The organic layers were combined, dried over Na$_2$SO$_4$, filtered, and evaporated to dryness. The resulting crude was first purified by flash chromatography (DCM to DCM/MeOH=95/5) and then by preparative LC-MS. The purified compound was partitioned between sat. NaHCO$_3$ and DCM, the organic phase was dried over Na$_2$SO$_4$, filtered and evaporated under vacuum to give 90.8 mg of the title compound (33% yield, mixture of diastereomers).

$^1$H NMR (300 MHz, CHLOROFORM-d) ppm

Diastereomer 1 of I33: 7.46-7.57 (m, 2H), 7.29-7.45 (m, 3H), 7.08-7.21 (m, 2H), 6.67-6.81 (m, 1H), 6.50-6.67 (m, 2H), 5.20-5.37 (m, 1H), 5.12 (d, 1H), 4.84-5.05 (m, 1H), 2.46-3.04 (m, 4H), 2.44 (s, 3H), 2.10-2.26 (m, 1H), 1.63-1.82 (m, 1H).

Diastereomer 2 of I33: 7.46-7.57 (m, 2H), 7.29-7.45 (m, 3H), 7.08-7.21 (m, 2H), 6.67-6.81 (m, 1H), 6.50-6.67 (m, 2H), 5.20-5.37 (m, 1H), 5.12 (d, 1H), 4.84-5.05 (m, 1H), 2.46-3.04 (m, 4H), 2.33 (s, 3H), 2.26-2.40 (m, 1H), 1.86-2.05 (m, 1H);

LC-MS (ESI POS): 311.3 (MH+).

Example 13

Preparation of (R)-quinuclidin-3-yl 2-(methyl(phenyl)amino)-2-phenylacetate (I36)

sealed tube under microwave irradiation at 100° C. for 30 minutes. Acetonitrile was evaporated, residue was taken up with EtOAc and washed sequentially with 1N NaHCO$_3$, 1N HCl and brine. The organic phase was dried over Na$_2$SO$_4$, filtered and evaporated to dryness. The residue was triturated with hexane and then purified by flash chromatography (Petroleum ether/EtOAc=97/3) to obtain ethyl 2-(methyl(phenyl)amino)-2-phenylacetate (4.6 g, 64.3% yield).

Preparation of 2-(methyl(phenyl)amino)-2-phenylacetic acid hydrochloride (I35)

Ethyl 2-(methyl(phenyl)amino)-2-phenylacetate (I34) (4.6 g, 17.1 mmol) and lithium hydroxide (1.43 g, 59.8 mmol) were dissolved in THF (110 ml) and water (55 ml) and stirred at room temperature. THF was removed in vacuo, and the aqueous phase was treated with 2N HCl. The precipitate was collected and purified by flash chromatography (DCM/MeOH=8/2) to afford 2-(methyl(phenyl)amino)-2-phenylacetic acid hydrochloride (3.2 g, 78% yield).

Preparation of (R)-quinuclidin-3-yl 2-(methyl(phenyl)amino)-2-phenylacetate (I36)

2-(Methyl(phenyl)amino)-2-phenylacetic acid (I35) (2.20 g, 9.12 mmol) was dissolved in THF (25 ml), and (R)-quinu-

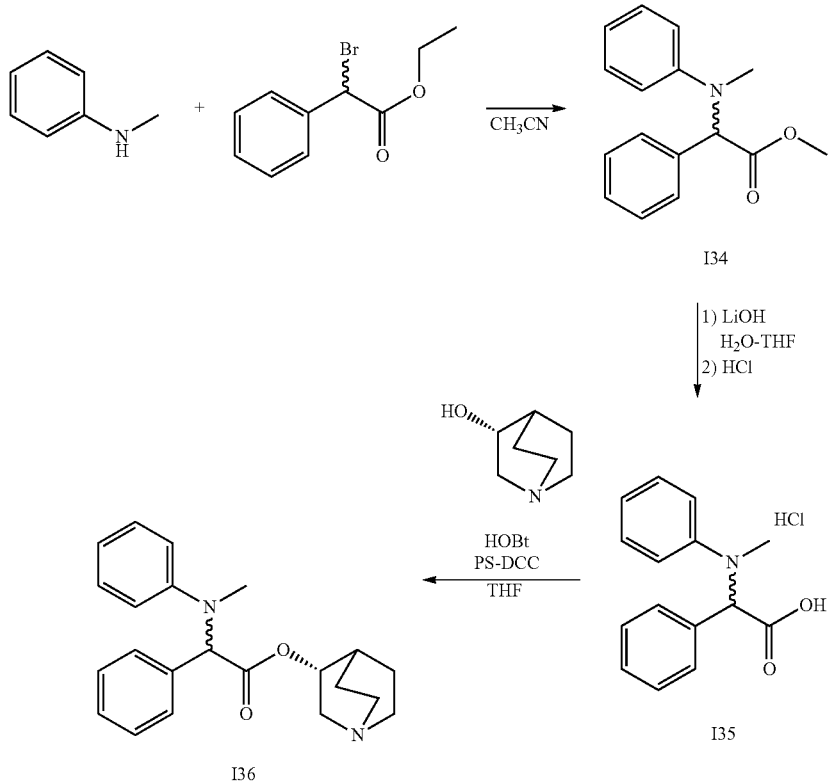

Scheme 14

Preparation of ethyl 2-(methyl(phenyl)amino)-2-phenylacetate (I34)

N-methylaniline (2.88 ml, 26.6 mmol) was added to a solution of ethyl 2-bromo-2-phenylacetate (4.65 ml, 26.6 mmol) in acetonitrile (55 ml). The reaction was heated in clidin-3-ol (1.28 g, 10.0 mmol) was added. To the resulting solution, HOBt (1.23 g, 9.12 mmol) and DCC (1.88 g, 9.12 mmol) were added, and the mixture was stirred at room temperature for three days. THF was removed under vacuum and the residue was portioned between H$_2$O and EtOAc. The organic phase was washed with a saturated aqueous Na$_2$CO$_3$ solution, dried over Na$_2$SO$_4$ and evaporated to dryness. The crude was purified by flash chromatography (EtOAc to EtOAc/MeOH=75/25) to afford (R)-quinuclidin-3-yl 2-(methyl(phenyl)amino)-2-phenylacetate (2.2 g, 68.8% yield, mixture of diastereomers).

$^1$H NMR (300 MHz, DMSO-d$_6$) ppm 7.29-7.53 (m, 5H) 7.14-7.29 (m, 2H) 6.86-6.99 (m, 2H) 6.67-6.80 (m, 1H) 5.84 and 5.83 (s, 1H) 4.73-4.88 (m, 1H) 2.99-3.16 (m, 1H) 2.75 and 2.71 (s, 3H) 2.53-2.69 (m, 3H) 2.29-2.47 (m, 2H) 1.74-1.95 (m, 1H) 1.32-1.63 (m, 3H) 1.12-1.30 (m, 1H);

LC-MS (ESI POS): 351.5 (MH+).

Example 14

Preparation of (R)—((R)-quinuclidin-3-yl) 2-(4-fluorophenylamino)-2-phenylacetate (Diastereoisomer 1 of I39)

Preparation of 2-(4-fluorophenylamino)-2-phenylacetic acid hydrochloride (I38)

Ethyl 2-(4-fluorophenylamino)-2-phenylacetate (I37) (4.10 g, 15.0 mmol) and lithium hydroxide (1.26 g, 52.5 mmol) were dissolved in THF (100 ml) and water (50 ml). The reaction mixture was stirred at room temperature for three days. THF was evaporated, and the resulting basic aqueous solution was acidified till pH 1 with 1N HCl. The solid that precipitated out was recovered by suction filtration and dried at 40° C. under vacuum overnight to obtain 2-(4-fluorophenylamino)-2-phenylacetic acid hydrochloride (4.06 g, 96% yield).

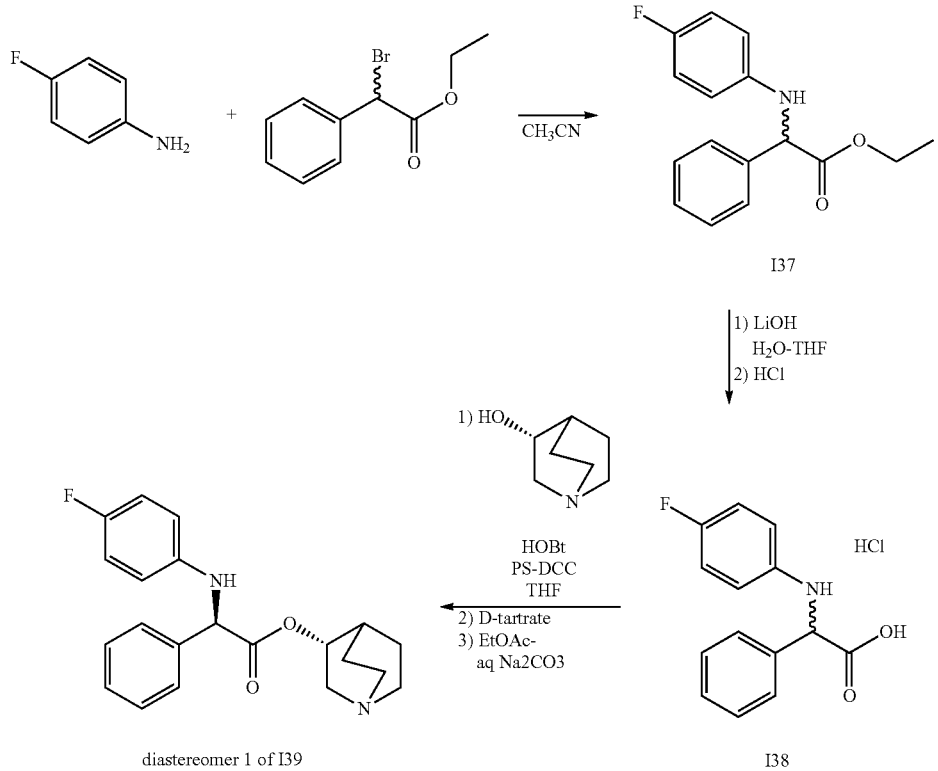

Scheme 15

Preparation of ethyl 2-(4-fluorophenylamino)-2-phenyl acetate (I37)

4-Fluoroaniline (2.38 ml, 24.8 mmol) was added to a solution of ethyl 2-bromo-2-phenylacetate (4.34 ml, 24.8 mmol) in acetonitrile (50 ml). The reaction was heated under microwave irradiation at 100° C. for 30 minutes. Acetonitrile was evaporated, the residue was taken up with EtOAc and washed with 1N NaHCO$_3$, 1N HCl and brine (100 ml). The organic phase was dried over Na$_2$SO$_4$, filtered and evaporated to dryness. The crude was purified by flash chromatography (Petroleum ether/EtOAc=99/1 to 8/2) to afford ethyl 2-(4-fluorophenylamino)-2-phenylacetate (4.90 g, 72.3% yield).

Preparation of (R)—((R)-quinuclidin-3-yl) 2-(4-fluorophenylamino)-2-phenylacetate (Diastereoisomer 1 of I39)

2-(4-Fluorophenylamino)-2-phenylacetic acid hydrochloride (I38) (2.00 g, 8.15 mmol) was dissolved in THF (25 ml), and (R)-quinuclidin-3-ol (1.14 g, 8.97 mmol) was added. To the resulting solution, HOBt (1.10 g, 8.15 mmol) and DCC (0.841 g, 4.08 mmol) were added, and the mixture was stirred at room temperature for three days. Then a second portion of HOBt (0.55 g, 4.08 mmol), DCC (0.84 g, 4.08 mmol) and (R)-quinuclidin-3-ol (0.52 g, 4.08 mmol) were added, and the mixture was stirred at room temperature overnight. THF was removed under vacuum, and the residue was treated with H$_2$O and extracted twice with EtOAc. The combined organic phases were washed with saturated Na$_2$CO$_3$ and dried over Na$_2$SO$_4$, filtered and the solvent was evaporated in vacuo. The crude was purified by flash chromatography (EtOAc/MeOH=9/1 to 75/25) to afford (R)-quinuclidin-3-yl 2-(4-fluorophenylamino)-2-phenylacetate (1.1 g, 3.10 mmol, 38.1% yield, mixture of diasteromers).

(2S,3S)-2,3-dihydroxysuccinic acid (0.23 g, 1.52 mmol) was added to a suspension of (R)-quinuclidin-3-yl 2-(4-fluorophenylamino)-2-phenylacetate (1.08 g, 3.05 mmol) in acetone (140 ml). The resulting mixture was heated at reflux and then allowed to cool at room temperature.

The precipitate was removed by filtration, and the mother solution was evaporated to dryness. The residue was dissolved in EtOAc (250 mL) and washed with saturated Na$_2$CO$_3$ solution (50 ml). The organic phase was dried over Na$_2$SO$_4$, filtered and evaporated to give (R)—((R)-quinuclidin-3-yl) 2-(4-fluorophenylamino)-2-phenyl acetate (490 mg; 45% yield, single diastereomer).

$^1$H NMR (300 MHz, DMSO-d$_6$) δ ppm 7.48-7.58 (m, 2H), 7.28-7.43 (m, 3H), 6.85-6.97 (m, 2H), 6.64-6.77 (m, 2H), 6.28 (d, 1H), 5.25 (d, 1H), 4.64-4.81 (m, 1H), 3.01 (ddd, 1H), 2.54-2.72 (m, 3H), 2.21-2.40 (m, 1H), 2.03-2.15 (m, 1H), 1.86-1.97 (m, 1H), 1.38-1.74 (m, 3H), 1.21-1.38 (m, 1H);

LC-MS (ESI POS): 355.2 (MH+).

Example 15

Preparation of (R)-quinuclidin-3-yl 2-(3-fluorophenylamino)-2-phenylacetate (I41)

Scheme 16

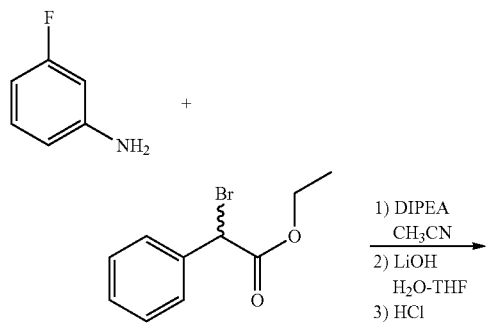

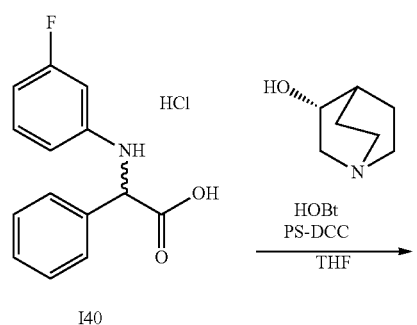

I40

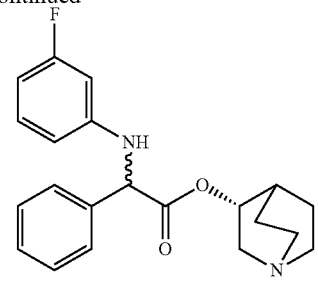

I41

Preparation of 2-(3-fluorophenylamino)-2-phenylacetic acid hydrochloride (I40)

Ethyl 2-bromo-2-phenylacetate (1.05 ml, 6.00 mmol), 3-fluoroaniline (1.00 g, 9.00 mmol), and N-ethyl-N-isopropylpropan-2-amine (1.57 ml, 9.00 mmol) were dissolved in acetonotrile (20 ml) and stirred under microwave irradiation at 100° C. for 2 hours. Water (21 ml) and lithium hydroxide (718 mg, 30.0 mmol) were added, and the resulting mixture was stirred at room temperature overnight. Acetonitrile was evaporated and 1N HCl was added until pH was about 1. The aqueous phase was extracted three times with EtOAc. The combined organic layers were washed with water and brine, dried (Na$_2$SO$_4$), filtered and evaporated to give 2-(3-fluorophenylamino)-2-phenylacetic acid hydrochloride (1.28 g, 76% yield).

Preparation of (R)-quinuclidin-3-yl 2-(3-fluorophenylamino)-2-phenylacetate (I41)

2-(3-Fluorophenylamino)-2-phenylacetic acid hydrochloride (I40) (1.34 g, 4.74 mmol), (R)-quinuclidin-3-ol (3.01 g, 23.7 mmol), DCC (1.95 g, 9.47 mmol), and HOBt (1.45 g, 9.47 mmol) were dissolved in THF (60 ml). The reaction was stirred at room temperature overnight. The solvent was evaporated, and the crude product was taken up with EtOAc and washed with NaHCO$_3$ and then with brine. The organic phase was dried over Na$_2$SO$_4$, filtered and evaporated to dryness. The crude was purified by flash chromatography (DCM/MeOH=9/1) to give (R)-quinuclidin-3-yl 2-(3-fluorophenylamino)-2-phenylacetate (1.17 g, 68.9% yield).

LC-MS (ESI POS): 354.2 (MH+).

Example 16

Preparation of (R)-quinuclidin-3-yl 2-(benzo[b]thiophen-3-yl)-2-(phenylamino)acetate (I43)

Scheme 17

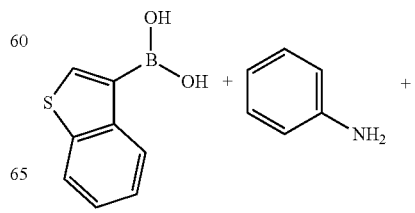

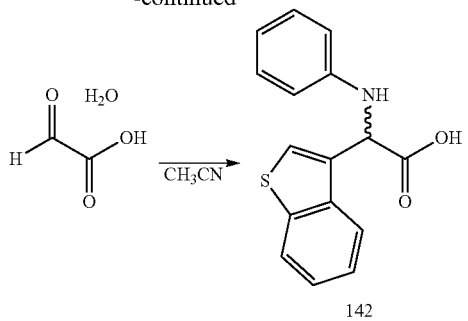

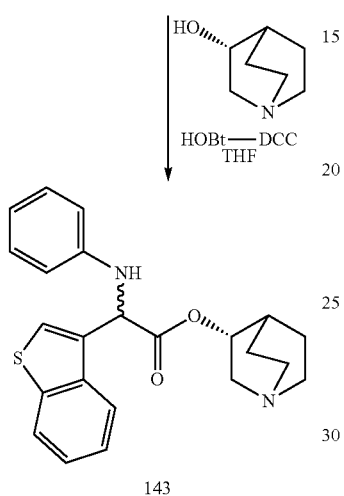

Preparation of 2-(benzo[b]thiophen-3-yl)-2-(phenylamino)acetic acid (I42)

Benzo[b]thiophen-3-ylboronic acid (387 mg, 2.17 mmol), aniline (202 mg, 2.17 mmol), and 2-oxoacetic acid hydrate (200 mg, 2.17 mmol) were dissolved in CH$_3$CN (12 ml) and stirred in a microwave reactor at 100° C. for 1 hour. The solvent was evaporated, and the residue was dissolved in EtOAc and washed with sat. NaHCO$_3$. The pH of aqueous phase was adjusted with 2N HCl to about 7, and the product was extracted with EtOAc. The organic phase was dried with Na$_2$SO$_4$, filtered and evaporated to obtain 2-(benzo[b]thiophen-3-yl)-2-(phenylamino)acetic acid (295 mg, 47.9% yield), which was used in the next step without any further purification.

Preparation of (R)-quinuclidin-3-yl 2-(benzo[b]thiophen-3-yl)-2-(phenylamino)acetate (I43)

2-(Benzo[b]thiophen-3-yl)-2-(phenylamino)acetic acid (I42) (295 mg, 1.04 mmol), (R)-quinuclidin-3-ol (159 mg, 1.25 mmol), HOBt (191 mg, 1.25 mmol), and DCC (258 mg, 1.25 mmol) were dissolved in dry THF and stirred at room temperature for 15 hours. THF was evaporated, and the crude product was dissolved in EtOAc and washed sequentially with NaHCO$_3$, water and brine. The organic phase was dried over Na$_2$SO$_4$, filtered and evaporated. The crude was purified by flash chromatography (DCM/MeOH=9/1) to obtain (R)-quinuclidin-3-yl 2-(benzo[b]thiophen-3-yl)-2-(phenylamino)acetate (180 mg, 44% yield, mixture of diastereomers).

$^1$H NMR (300 MHz, DMSO-d$_6$, diastereomer 1) δ ppm 8.13 (dd, 1H), 7.92-8.06 (m, 1H), 7.83 (s, 1H), 7.43 (m, 2H), 6.95-7.18 (m, 2H), 6.67-6.85 (m, 2H), 6.49-6.66 (m, 1H), 6.37 (d, 1H), 5.71 (d, 1H), 4.55-4.93 (m, 1H), 2.98-3.16 (m, 1H), 2.53-2.61 (m, 4H), 2.32-2.48 (m, 1H), 1.59-1.71 (m, 1H), 1.28-1.58 (m, 3H), 0.89-1.15 (m, 1H);

$^1$H NMR (300 MHz, DMSO-d$_6$, diastereomer 2) 8.06-8.20 (m, 1H), 7.95-8.06 (m, 1H), 7.86 (s, 1H), 7.33-7.50 (m, 2H), 7.01-7.16 (m, 2H), 6.73-6.85 (m, 2H), 6.55-6.67 (m, 1H), 6.38 (d, 1H), 5.72 (d, 1H), 4.61-4.76 (m, 1H), 2.92 (ddd, 1H), 2.55-2.70 (m, 3H), 1.94-2.18 (m, 2H), 1.80-1.94 (m, 1H), 1.31-1.62 (m, 3H), 1.03-1.31 (m, 1H);

LC-MS (ESI POS): 393.22 (MH+).

Example 17

Preparation of 3-(chloromethyl)-5-phenyl-1,2,4-oxadiazole (I45)

Scheme 18

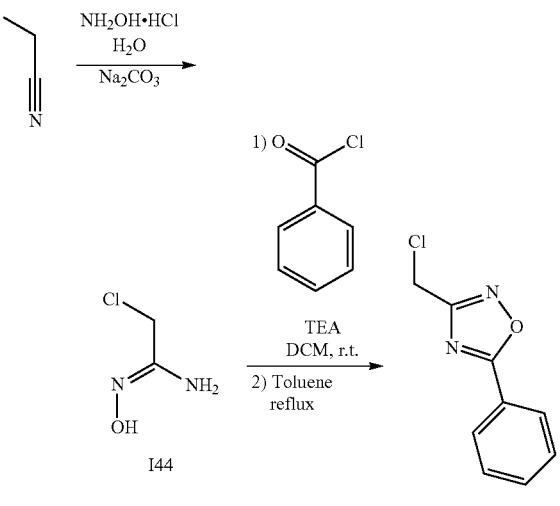

Preparation of 2-chloro-N'-hydroxyacetimidamide (I44)

2-Chloroacetonitrile (2.0 g, 26.5 mmol) and hydroxylamine hydrochloride (1.84 g, 26.5 mmol) were dissolved in water (6.6 ml), and the colorless solution was cooled to 10-15° C. with an ice-bath. Na$_2$CO$_3$ (1.40 g, 13.2 mmol) was added portion-wise to the mixture keeping the temperature below 30° C. The mixture was then stirred for 1 hour at 30° C. NaCl was added, and the mixture was extracted four times with Et$_2$O (30 ml×4). The combined organic phases were dried (Na$_2$SO$_4$), filtered and evaporated to obtain 2-chloro-N'-hydroxyacetimidamide (1.55 g, 53.8% yield). The compound was used in the next step without any further purification.

Preparation of 3-(chloromethyl)-5-phenyl-1,2,4-oxadiazole (I45)

Benzoyl chloride (1.60 ml, 13.8 mmol) was added to a suspension of 2-chloro-N'-hydroxyacetimidamide (I44) (1.0 g, 9.21 mmol) in DCM (25 ml), with stirring at room temperature. After 30 minutes, TEA (1.41 ml, 10.1 mmol) was added to the white suspension, and the mixture was stirred for additional 30 minutes. (UPLC-MS complete conversion). The solution was diluted with DCM (20 ml), and water (30 ml) was added. The aqueous phase was extracted three times with DCM (15 ml), and the combined organic phases were dried (Na$_2$SO$_4$), filtered and evaporated. The resulting residue is suspended in toluene (25 ml), and the mixture is heated to reflux for six hours and then at room temperature for two days. The dark solution was evaporated, and the crude product was purified by flash chromatography eluting with petroleum ether/EtOAc=95/5 to obtain 3-(chloromethyl)-5-phenyl-1,2,4-oxadiazole (803 mg, 44.8% yield) as a off-white solid.

$^1$H NMR (300 MHz, DMSO-d$_6$) δ ppm 8.06-8.20 (m, 2H), 7.69-7.79 (m, 1H), 7.57-7.69 (m, 2H), 4.96 (s, 2H);

LC-MS (ESI POS): 194.9 (MH+).

The intermediates listed in Table 2 were obtained as previously described for I45, starting from I44 and the suitable commercially available acyl chlorides.

TABLE 2

| Compound | Structure | Chromatography Eluent | Yield | Analytical |
|---|---|---|---|---|
| 146 | (3-chloromethyl-5-(4-methylphenyl)-1,2,4-oxadiazole) | Petr.ether/EtOAc = 95/5 to 9/1 | 22% | LC-MS (ESI POS): 209.2 (MH$^+$) |
| 147 | (3-chloromethyl-5-(4-fluorophenyl)-1,2,4-oxadiazole) | Petr.ether/EtOAc = 95/5 to 9/1 | 31% | LC-MS (ESI POS): 213.2 (MH$^+$) |
| 148 | (3-chloromethyl-5-(4-chlorophenyl)-1,2,4-oxadiazole) | Petr.ether/EtOAc = 95/5 to 9/1 | 32% | LC-MS (ESI POS): 229.2 (MH$^+$) |
| 149 | (3-chloromethyl-5-(3-fluorophenyl)-1,2,4-oxadiazole) | Petr.ether/EtOAc = 95/5 to 9/1 | 45% | LC-MS (ESI POS): 212.9 (MH$^+$) |

TABLE 2-continued

| Compound | Structure | Chromatography Eluent | Yield | Analytical |
| --- | --- | --- | --- | --- |
| 150 | 3-(chloromethyl)-5-(2-fluorophenyl)-1,2,4-oxadiazole | Petr.ether/EtOAc = 95/5 to 9/1 | 7.4% | LC-MS (ESI POS): 212.9 (MH$^+$) |
| 151 | 3-(chloromethyl)-5-(pyridin-4-yl)-1,2,4-oxadiazole | Petr.ether/EtOAc = 9/1 to 7/3 | 13% | LC-MS (ESI POS): 195.9 (MH$^+$) |
| 152 | 5-benzyl-3-(chloromethyl)-1,2,4-oxadiazole | Petr.ether/EtOAc = 95/5 to 9/1 | 29% | LC-MS (ESI POS): 209.0 (MH$^+$) |
| 153 | 3-(chloromethyl)-5-(1,3-dimethyl-1H-pyrazol-5-yl)-1,2,4-oxadiazole | DCM | 32% | LC-MS (ESI POS): 213.0 (MH$^+$) |
| 154 | 3-(chloromethyl)-5-cyclohexyl-1,2,4-oxadiazole | DCM | 32% yield | LC-MS (ESI POS): 201.1 (MH$^+$) |
| 155 | 3-(chloromethyl)-5-(thiazol-2-yl)-1,2,4-oxadiazole | DCM | 23% | LC-MS (ESI POS): 202.0 (MH$^+$) |

TABLE 2-continued

| Compound | Structure | Chromatography Eluent | Yield | Analytical |
|---|---|---|---|---|
| 156 | 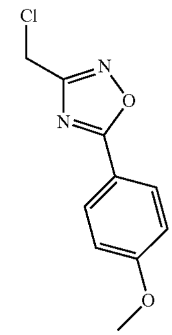 | n-Hexane/EtOAc = 9/1 to 8/2 | 35% | LC-MS (ESI POS): 225.1 (MH⁺) |
| 157 | 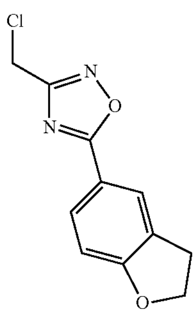 [SMILES: ClCc1noc(-c2ccc3c(c2)CCO3)n1] | n-Hexane/EtOAc = 9/1 | 32% | LC-MS (ESI POS): 237.0 (MH⁺) |
| 158 | 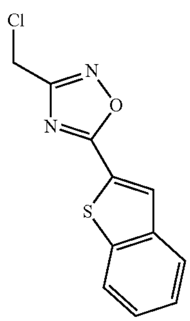 [SMILES: ClCc1noc(-c2cc3ccccc3s2)n1] | n-Hexane/EtOAc = 94/6 to 9/1 | 17% | LC-MS (ESI POS): 250.9 (MH⁺) |

Example 18

Preparation of 4-(chloromethyl)-2-phenyloxazole (I59)

Scheme 19

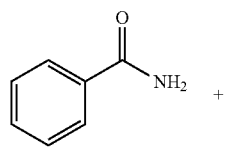

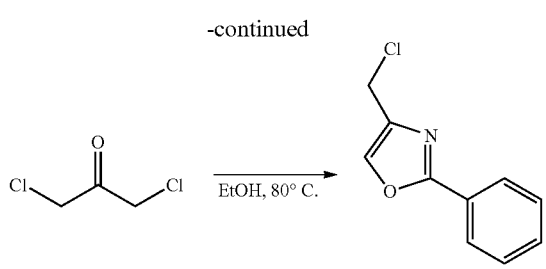

A mixture of benzamide (0.8 g, 6.60 mmol) and 1,3-dichloropropan-2-one (1.00 g, 7.92 mmol) was heated at 130° C. stirring under nitrogen atmosphere for 1 hour (UPLC/MS complete conversion). The obtained brown solution was cooled to room temperature, and the brown solid was suspended in acetonitrile (25 ml) and heated to reflux. The white insoluble solid was eliminated by filtration, and the solution was allowed to cool to room temperature. The formed precipitate was collected by filtration and washed with acetonitrile (8 ml), dissolved in EtOAc (20 ml) and washed with aq. NaHCO$_3$ (15 ml). The organic phase was dried (Na$_2$SO$_4$), filtered and evaporated to obtain 4-(chloromethyl)-2-phenyloxazole (315 mg, 24.7% yield).

$^1$H NMR (300 MHz, DMSO-d$_6$) δ ppm 8.27 (s, 1H), 7.89-8.09 (m, 2H), 7.39-7.68 (m, 3H), 4.74 (s, 2H);

LC-MS (ESI POS): 193.9 (MH+).

Example 19

Preparation of 4-chloromethyl-2-phenyl-thiazole (I60)

Scheme 20

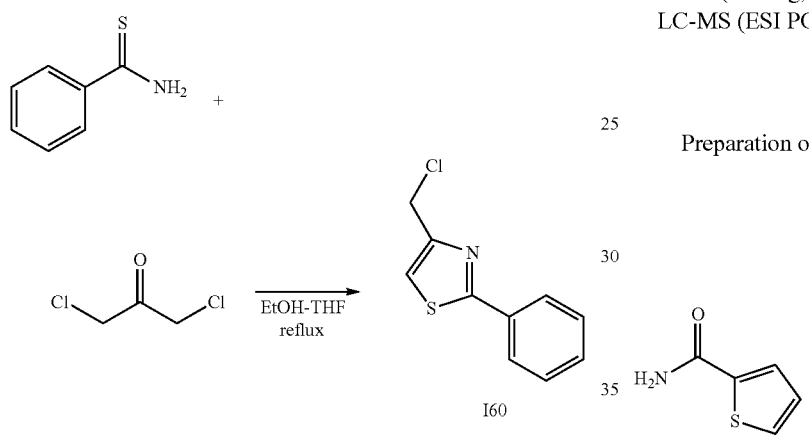

Benzothioamide (0.8 g, 5.83 mmol) was dissolved in a mixture EtOH (26.0 ml) and THF (10.4 ml), and the solution was heated to 65° C. 1,3-Dichloropropan-2-one (0.81 g, 6.41 mmol) was added, and the mixture was heated to reflux overnight (UPLC-MS: complete conversion). The solvents were evaporated, and the residue was taken up with EtOAc (100 ml) and washed with an aqueous solution of NaHCO$_3$. The organic phase was dried (Na$_2$SO$_4$), filtered and evaporated to dryness. The crude was purified by flash chromatography eluting with petroleum ether/EtOAc=97/3 to obtain 4-chloromethyl-2-phenyl-thiazole (891 mg, 72.9% yield).

$^1$H NMR (300 MHz, DMSO-d$_6$) δ ppm 7.89-8.10 (m, 2H), 7.81 (s, 1H), 7.38-7.64 (m, 3H), 4.88 (s, 2H);

LC-MS (ESI POS): 209.8 (MH+).

Example 20

Preparation of 2-(4-(chloromethyl)oxazol-2-yl)benzonitrile (I61)

Scheme 21

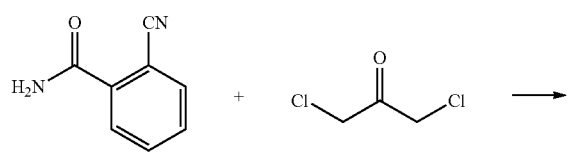

2-(4-(Chloromethyl)oxazol-2-yl)benzonitrile and 1,3-dichloropropan-2-one (0.83 g, 6.57 mmol) were heated to 150° C. for 2.5 hours. The dark solid was dissolved in EtOAc and washed with aqueous NaHCO$_3$. The organic phase was dried with Na$_2$SO$_4$, filtered and evaporated. The crude was purified by flash chromatography (Petroleum ether/EtOAc=9/1) to obtain 2-(4-(chloromethyl)oxazol-2-yl)benzonitrile (340 mg, 28% yield).

LC-MS (ESI POS): 219.1 (MH+).

Example 21

Preparation of 4-(chloromethyl)-2-(thiophen-2-yl)oxazole (I62)

Scheme 22

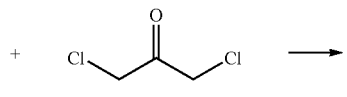

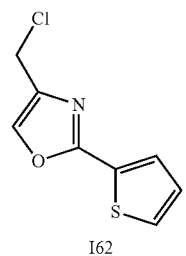

Thiophene-2-carboxamide (0.8 g, 6.29 mmol) and 1,3-dichloropropan-2-one (0.96 g, 7.55 mmol) were heated at 150° C. for 2.5 hours. The dark solid was dissolved in EtOAc and washed with aqueous NaHCO$_3$, then the organic phase was dried over Na$_2$SO$_4$, filtered and evaporated to dryness. The dark brown oil was purified by flash chromatography (Petroleum ether/EtOAc=9/1) to obtain 4-(chloromethyl)-2-(thiophen-2-yl)oxazole (790 mg, 63% yield).

LC-MS (ESI POS): 200.1 (MH+).

Example 22

Preparation of (R)-1-((5-phenyl-1,2,4-oxadiazol-3-yl)methyl)-3-((R)-2-phenyl-2-(phenylamino)acetoxy)-1-azoniabicyclo[2.2.2]octane chloride (Diastereomer 1 of C63)

Scheme 23

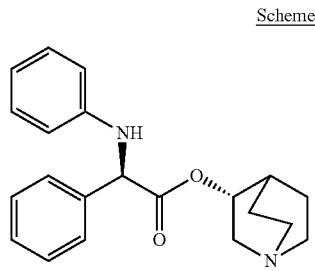

Diastereomer 1 of I2

+

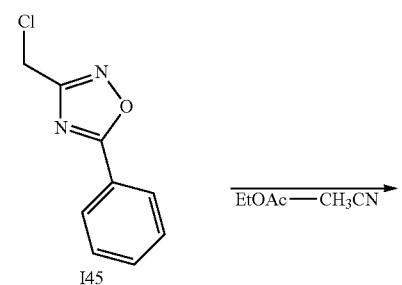

I45

$\xrightarrow{\text{EtOAc—CH}_3\text{CN}}$

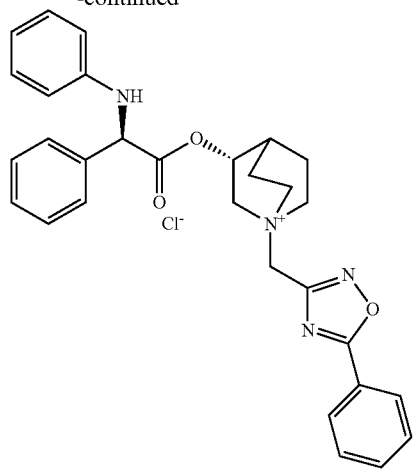

Diastereomer 1 of C63

To a solution of (R)—((R)-quinuclidin-3-yl) 2-phenyl-2-(phenylamino)acetate (diastereomer 1 of I2) (100 mg, 0.30 mmol) in EtOAc (2 ml) and acetonitrile (0.99 ml) was added 3-(chloromethyl)-5-phenyl-1,2,4-oxadiazole (I45) (69.4 mg, 0.36 mmol). The pale yellow solution was stirred at room temperature for 24 hours. The suspension was filtered on a buckner funnel washing with EtOAc (5 ml). The white solid was recovered from the filter to obtain the title compound (98 mg, 62.1% yield).

$^1$H NMR (300 MHz, DMSO-$d_6$) δ ppm 8.10-8.26 (m, 2H) 7.76-7.88 (m, 1H) 7.64-7.76 (m, 2H) 7.49-7.59 (m, 2H) 7.18-7.42 (m, 3H) 6.98-7.16 (m, 2H) 6.67-6.78 (m, 2H) 6.53-6.64 (m, 1H) 6.41 (d, 1H) 5.31-5.39 (m, 1H) 5.07-5.22 (m, 1H) 4.82 (s, 2H) 3.95-4.27 (m, 1H) 3.48-3.79 (m, 3H) 3.36 (d, 1H) 3.01-3.24 (m, 1H) 2.26-2.40 (m, 1H) 1.67-2.13 (m, 4H);

LC-MS (ESI POS): 495.16 (M+).

Final compounds listed in Table 3 were prepared as previously described for C63, by alkylation of intermediate I2, I4, I7, I12, I13, I14, I17, I18 and I21 with I45, I59, I60, I61, I62 and other commercially available alkylating agents.

TABLE 3

| Compound | Structure | Yield | Analytical |
|---|---|---|---|
| Diastereomer 1 of C64 | Single diastereomer | 74.3% | LC-MS (ESI POS): 494.22 (M$^+$)<br>$^1$H NMR (300 MHz, DMSO-$d_6$) δ ppm 8.44 (s, 1 H), 7.95-8.09 (m, 2 H), 7.55-7.69 (m, 3 H), 7.44-7.54 (m, 2 H), 7.15-7.36 (m, 3 H), 6.93-7.10 (m, 2 H), 6.70 (d, 2 H), 6.50-6.63 (m, 1 H), 6.37 (d, 1 H), 5.27-5.37 (m, 1 H), 5.04-5.19 (m, 1 H), 4.48 (d, 1 H), 4.42 (d, 1 H), 3.93 (ddd, 1 H), 3.38-3.64 (m, 3 H), 3.13 (d, 1 H), 2.81-2.99 (m, 1 H), 2.23-2.37 (m, 1 H), 1.66-2.13 (m, 4 H) |

TABLE 3-continued

| Compound | Structure | Yield | Analytical |
|---|---|---|---|
| Diastereomer 1 of C65 | 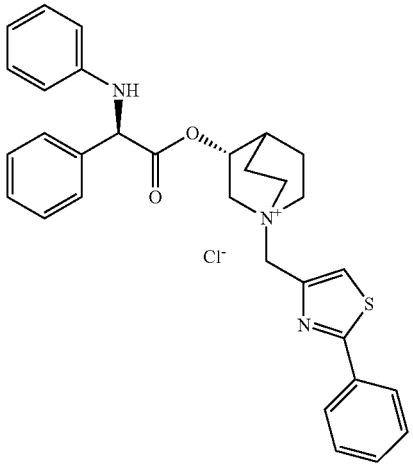 Single diastereomer | 83% | LC-MS (ESI POS): 510.21 (M$^+$) $^1$H NMR (300 MHz, DMSO-d$_6$) δ ppm 8.04 (s, 1 H) 7.94-8.02 (m, 2 H) 7.55-7.61 (m, 3 H) 7.44-7.51 (m, 2 H) 7.17-7.31 (m, 1 H) 6.99-7.09 (m, 2 H) 6.69 (d, 2 H) 6.56 (t, 1 H) 6.35 (d, 1 H) 5.31 (d, 1 H) 5.08-5.18 (m, 1 H) 4.50-4.65 (m, 2 H) 3.87-4.01 (m, 1 H) 3.39-3.69 (m, 3 H) 3.20 (d, 1 H) 2.82-3.02 (m, 1 H) 2.23-2.38 (m, 1 H) 1.72-2.11 (m, 4 H) |
| Diastereomer 1 of C66 | 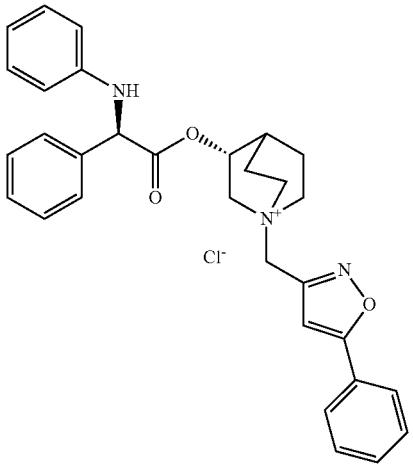 Single diastereomer | 65.1% | LC-MS (ESI POS): 494.24 (M$^+$) $^1$H NMR (300 MHz, DMSO-d$_6$) δ ppm 7.86-8.07 (m, 2 H) 7.48-7.68 (m, 5 H) 7.27-7.38 (m, 2 H) 7.25 (s, 1 H) 7.18-7.27 (m, 1 H) 6.99-7.11 (m, 2 H) 6.68-6.77 (m, 2 H) 6.56 (t, 1 H) 6.39 (d, 1 H) 5.34 (d, 1 H) 5.07-5.21 (m, 1 H) 4.67 (dd, 2 H) 3.90-4.08 (m, 1 H) 3.40-3.68 (m, 3 H) 3.18 (d, 1 H) 3.01 (s, 1 H) 2.25-2.38 (m, 1 H) 1.75-2.09 (m, 4 H) |
| Diastereomer 1 of C67 | 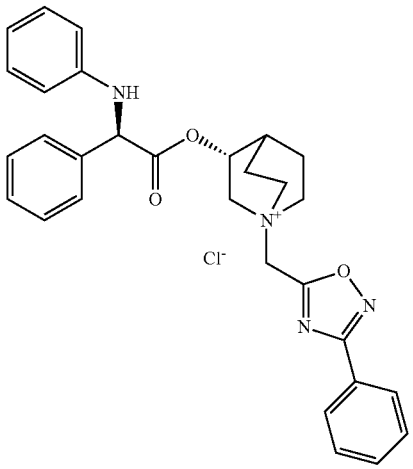 Single diastereomer | 83% | LC-MS (ESI POS): 495.24 (M$^+$) $^1$H NMR (300 MHz, DMSO-d$_6$) δ ppm 7.98-8.19 (m, 2 H) 7.49-7.76 (m, 5 H) 7.20-7.41 (m, 3 H) 6.98-7.13 (m, 2 H) 6.67-6.79 (m, 2 H) 6.58 (t, 1 H) 6.43 (d, 1 H) 5.30-5.43 (m, 1 H) 4.98-5.21 (m, 1 H) 5.08 (s, 2 H) 4.02-4.26 (m, 1 H) 3.31-3.83 (m, 4 H) 2.27-2.40 (m, 1 H) 1.73-2.10 (m, 4 H) |

TABLE 3-continued

| Compound | Structure | Yield | Analytical |
|---|---|---|---|
| Diastereomer 1 of C68 | Single diastereomer | 62.6% | LC-MS (ESI POS): 495.25 (M+)<br>$^1$H NMR (300 MHz, DMSO-$d_6$) δ ppm 7.98-8.12 (m, 2 H) 7.61-7.81 (m, 3 H) 7.49-7.61 (m, 2 H) 7.22-7.45 (m, 3 H) 7.01-7.14 (m, 2 H) 6.66-6.83 (m, 2 H) 6.59 (t, 1 H) 6.42 (d, 1 H) 5.30-5.41 (m, 1 H) 5.07-5.20 (m, 1 H) 5.00 (s, 2 H) 4.01-4.16 (m, 1 H) 3.47-3.80 (m, 4 H) 3.41 (d, 1 H) 2.25-2.39 (m, 1 H) 1.73-2.11 (m, 4 H) |
| Diastereomer 1 of C69 | Single diastereomer | 85% | LC-MS (ESI POS): 519.18 (M+)<br>$^1$H NMR (300 MHz, DMSO-$d_6$) δ ppm 8.59 (s, 1 H) 8.20 (dd, 1 H) 8.10 (dd, 1 H) 7.95 (td, 1 H) 7.73-7.88 (m, 1 H) 7.47-7.59 (m, 2 H) 7.15-7.39 (m, 3 H) 7.05 (dd, 2 H) 6.65-6.80 (m, 2 H) 6.57 (t, 1 H) 6.35 (d, 1 H) 5.33 (d, 1 H) 5.04-5.23 (m, 1 H) 4.33-4.60 (m, 2 H) 3.81-4.01 (m, 1 H) 3.38-3.69 (m, 3 H) 3.09 (d, 1 H) 2.85-3.03 (m, 1 H) 2.24-2.38 (m, 1 H) 1.75-2.09 (m, 4 H) |
| Diastereomer 1 of C70 | Single diastereomer | 28% | LC-MS (ESI POS): 500.11 (M+)<br>$^1$H NMR (300 MHz, DMSO-$d_6$) δ ppm 8.37 (s, 1 H) 7.90 (dd, 1 H) 7.80 (dd, 1 H) 7.41-7.58 (m, 2 H) 7.14-7.36 (m, 4 H) 7.04 (dd, 2 H) 6.63-6.77 (m, 2 H) 6.57 (t, 1 H) 6.34 (d, 1 H) 5.26-5.40 (m, 1 H) 5.02-5.22 (m, 1 H) 4.25-4.54 (m, 2 H) 3.89 (m, 1 H) 3.34-3.59 (m, 3 H) 3.05 (d, 1 H) 2.85 (m, 1 H) 2.30 (s, 1 H) 1.71-2.08 (m, 4 H) |

TABLE 3-continued

| Compound | Structure | Yield | Analytical |
|---|---|---|---|
| C71 | 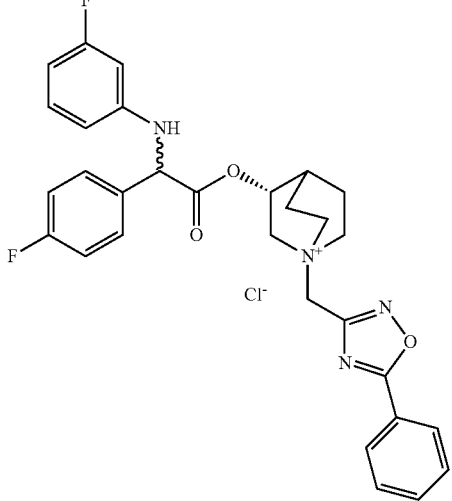<br>Mixture of diastereomer | 35% | LC-MS (ESI POS): 531.18 (M+)<br>$^1$H NMR (300 MHz, DMSO-d$_6$) δ ppm 8.09-8.24 (m, 2 H) 7.65-7.90 (m, 3 H) 7.49-7.65 (m, 2 H) 6.97-7.24 (m, 3 H) 6.79 (d, 1 H) 6.45-6.60 (m, 2 H) 6.27 - 6.41 (m, 1 H) 5.44 (t, 1 H) 5.14 (s, 1 H) 4.84 (s, 2 H) 4.07 (m, 1 H) 3.33-3.78 (m, 5 H) 2.29-2.40 (m, 1 H) 1.73-2.09 (m, 4 H) |
| C72 | 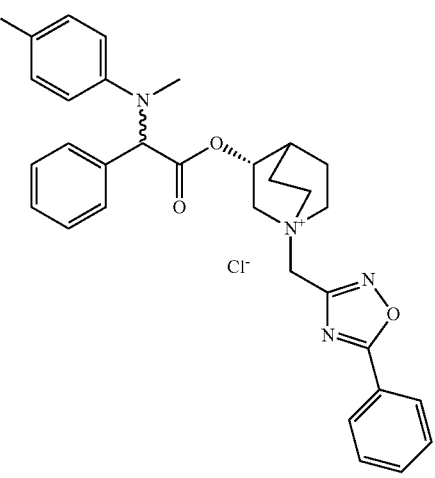<br>Mixture of diastereomer | 38.5% | LC-MS (ESI POS): 527.23 (M+)<br>$^1$H NMR (300 MHz, DMSO-d$_6$) δ ppm 8.16 (d, 2 H) 7.59-7.87 (m, 3 H) 7.28-7.52 (m, 5 H) 6.80-7.18 (m, 4 H) 5.87 (s, 1 H) 5.10-5.31 (m, 1 H) 4.87 (s, 2 H) 4.03-4.24 (m, 1 H) 3.47-3.81 (m, 4 H) 3.33-3.45 (m, 1 H) 2.72 (s, 3 H) 2.19-2.32 (m, 1 H) 1.59-2.03 (m, 4 H) |
| C73 | 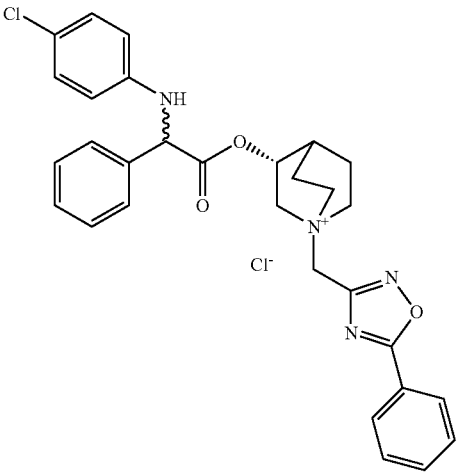<br>Mixture of diastereomer | 50% | LC-MS (ESI POS): 529.14 (M+)<br>$^1$H NMR (300 MHz, DMSO-d$_6$) δ ppm 8.06-8.27 (m, 2 H) 7.61-7.90 (m, 3 H) 7.53 (t, 2 H) 7.18-7.44 (m, 3 H) 7.08 (m, 2 H) 6.73 (m, 2 H) 6.60-6.83 (m, 1 H) 5.33 (s, 1 H) 5.04-5.19 (m, 1 H) 4.79-4.97 (m, 2 H) 3.99-4.19 (m, 1 H) 3.46-3.83 (m, 5 H) 2.06-2.18 (m, 1 H) 1.76-2.01 (m, 3 H) 1.59-1.74 (m, 1 H) |

TABLE 3-continued

| Compound | Structure | Yield | Analytical |
|---|---|---|---|
| C74 | 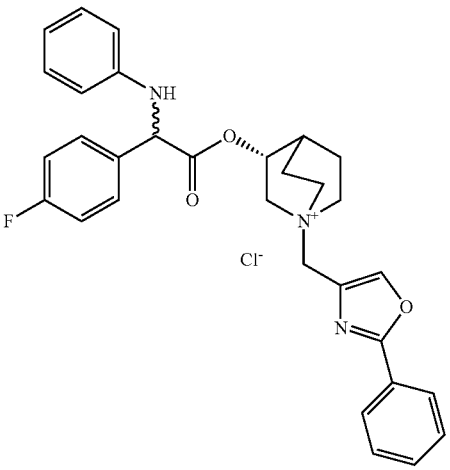<br>Mixture of diastereomer | 33% | LC-MS (ESI POS): 512.96 (M⁺)<br>¹H NMR (300 MHz, DMSO-d₆) δ ppm<br>8.44 (s, 1 H), 7.92-8.11 (m, 2 H), 7.44-7.70 (m, 5 H), 6.96-7.19 (m, 4 H), 6.63-6.80 (m, 2 H), 6.49-6.61 (m, 1 H), 6.39 (d, 1 H), 5.37 (d, 1 H), 5.05-5.18 (m, 1 H), 4.48 (d, 1 H), 4.42 (d, 1 H), 3.93 (ddd, 1 H), 3.38-3.63 (m, 3 H), 3.16 (d, 1 H), 2.83-3.07 (m, 1 H), 2.18-2.35 (m, 1 H), 1.61-2.11 (m, 4H) |
| C75 | 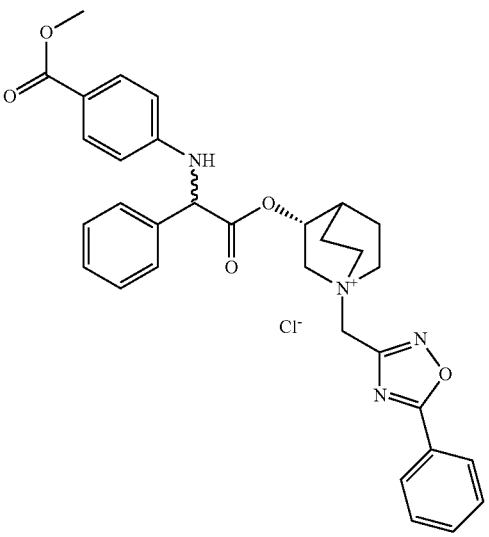<br>Mixture of diastereomer | 43% | LC-MS (ESI POS): 553.14 (M⁺)<br>¹H NMR (300 MHz, Acetone) δ ppm<br>8.29 (d, 1 H) 8.12-8.23 (m, 2 H) 7.59-7.86 (m, 7 H) 7.20-7.47 (m, 3 H) 7.03 (d, 2 H) 5.54 (d, 1 H) 5.47 (d, 1 H) 5.35 (d, 1 H) 5.19-5.29 (m, 1 H) 5.12 (d, 1 H) 4.70-4.89 (m, 1 H) 4.38 (ddd, 1 H) 3.78-4.06 (m, 3 H) 3.76 (s, 3 H) 2.69-3.09 (m, 2 H) 2.30-2.44 (m, 1 H) 2.10-2.20 (m, 1 H) 1.75-1.97 (m, 1 H) |
| C76 | 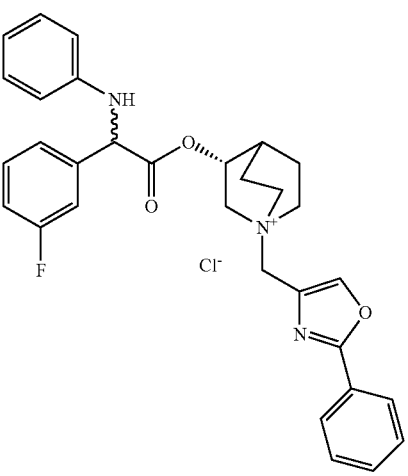<br>Mixture of diastereomer | 22% | LC-MS (ESI POS): 512.18 (M⁺)<br>¹H NMR (300 MHz, DMSO-d₆) δ ppm<br>8.44 (s, 1 H), 7.94-8.14 (m, 2 H), 7.55-7.68 (m, 3 H), 7.25-7.46 (m, 3 H), 6.98-7.17 (m, 3 H), 6.65-6.80 (m, 2 H), 6.53-6.64 (m, 1 H), 6.43 (d, 1 H), 5.42 (d, 1 H), 4.98-5.25 (m, 1 H), 4.48 (d, 1 H), 4.42 (d, 1 H), 3.92 (ddd, 1 H), 3.35-3.64 (m, 3 H), 3.11-3.23 (m, 1 H), 2.90-3.09 (m, 1 H), 2.17-2.40 (m, 1 H), 1.66-2.14 (m, 4 H) |

| Compound | Structure | Yield | Analytical |
|---|---|---|---|
| C77 | 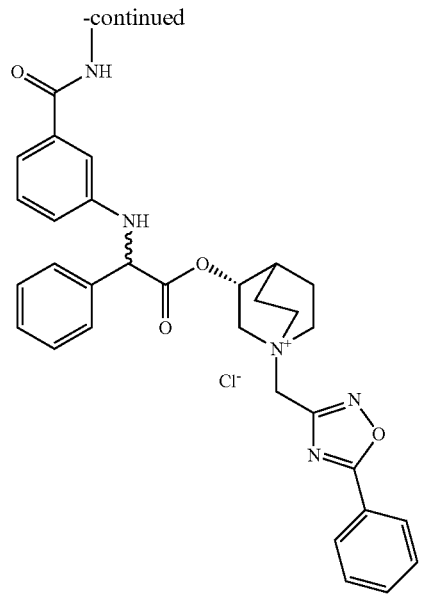<br>Mixture of diastereomer | 30% | LC-MS (ESI POS): 531.18 (M+)<br><sup>1</sup>H NMR (300 MHz, DMSO-d$_6$) δ ppm 8.08-8.31 (m, 2 H) 7.62-7.88 (m, 3 H) 7.47-7.62 (m, 2 H) 7.21-7.47 (m, 3 H) 6.97-7.16 (m, 1 H) 6.47-6.64 (m, 1 H) 6.31-6.47 (m, 1 H) 6.13 (t, 1 H) 5.50 and 5.48(d, 1 H) 5.06-5.23 (m, 1 H) 4.85 (d, 2 H) 4.00-4.19 (m, 1 H) 3.60-3.89 (m, 2 H) 3.49-3.60 (m, 2 H) 3.42 (d, 1 H) 2.09-2.20 (m, 1 H) 1.65-2.04 (m, 4 H) |

Example 23

Preparation of (R)-3-(2-(3-(methylcarbamoyl)phenylamino)-2-phenylacetoxy)-1-((5-phenyl-1,2,4-oxadiazol-3-yl)methyl)-1-azoniabicyclo-[2.2.2]octane chloride (C78)

Scheme 24

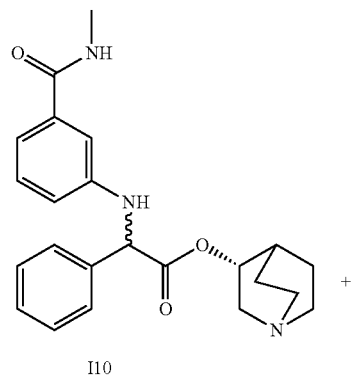

I10

+

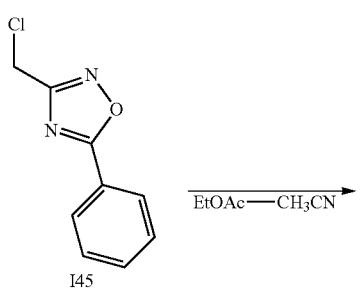

I45

$\xrightarrow{\text{EtOAc} - \text{CH}_3\text{CN}}$

-continued

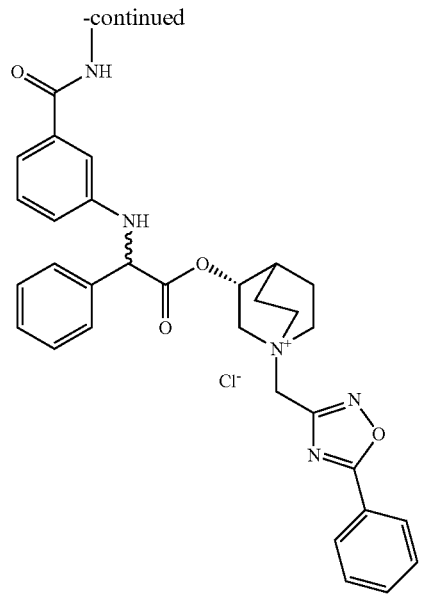

C78

3-(Chloromethyl)-5-phenyl-1,2,4-oxadiazole (I45) (53.9 mg, 0.28 mmol) was added to a solution of (R)-quinuclidin-3-yl 2-(3-(methylcarbamoyl)-phenylamino)-2-phenylacetate (I10) (99 mg, 0.252 mmol) in a mixture of ethyl acetate (3.3 ml) and acetonitrile (1.7 ml). The reaction was stirred at room temperature for 2 days. Then the solution was evaporated and the residue was triturated with EtOAc (10 ml). The suspension was filtered on a buckner funnel, and the solid was recovered and further purified by flash chromatography (DCM/MeOH=85/15) to obtain (R)-3-(2-(3-(methylcarbamoyl)phenylamino)-2-phenylacetoxy)-1-((5-phenyl-1,2,4-oxadiazol-3-yl)methyl)-1-azoniabicyclo[2.2.2]octane chloride (23 mg, 15% yield, mixture of diastereomers).

<sup>1</sup>H NMR (300 MHz, DMSO-d$_6$) δ ppm 8.28 (q, 1H), 8.09-8.21 (m, 2H), 7.74-7.83 (m, 1H), 7.63-7.74 (m, 2H), 7.51-7.62 (m, 2H), 7.28-7.46 (m, 3H), 7.17 (s, 1H), 7.13 (t, 1H), 7.02-7.09 (m, 1H), 6.90 (dd, 1H), 6.63 (d, 1H), 5.37 (d, 1H), 5.03-5.18 (m, 1H), 4.89 (s, 2H), 4.02-4.23 (m, 1H), 3.62-3.79 (m, 3H), 3.48-3.62 (m, 2H), 2.76 (d, 3H), 2.10-2.20 (m, 1H), 1.56-2.07 (m, 4H);

LC-MS (ESI POS): 552.15 (M+).

Example 24

Preparation of (3R)-1-((5-phenyl-1,2,4-oxadiazol-3-yl)methyl)-3-(2-phenyl-2-(o-tolylamino)acetoxy)-1-azoniabicyclo[2.2.2]octane chloride (C79)

Scheme 25

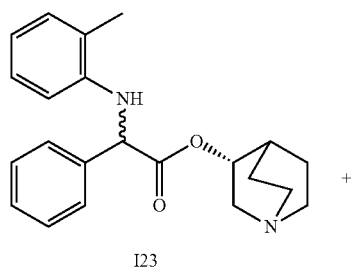

I23

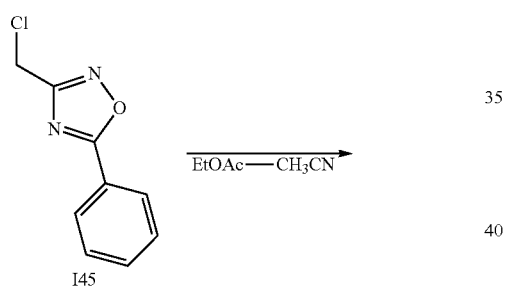

I45

3-(Chloromethyl)-5-phenyl-1,2,4-oxadiazole (I45) (79 mg, 0.40 mmol) was added to a solution of (R)-quinuclidin-3-yl 2-phenyl-2-(o-tolylamino)acetate (I23) (129 mg, 0.37 mmol) in acetonitrile (1.2 ml) and ethyl acetate (2.4 ml). The yellow solution was stirred at room temperature for 48 hours. The solution was evaporated, and the residue was purified by flash chromatography (DCM/MeOH=9/1) to obtain (3R)-1-((5-phenyl-1,2,4-oxadiazol-3-yl)methyl)-3-(2-phenyl-2-(o-tolylamino)acetoxy)-1-azoniabicyclo[2.2.2]octane chloride (39 mg, 19% yield, mixture of diastereomers).

$^1$H NMR (300 MHz, DMSO-d$_6$, diastereomer 1) δ ppm 8.11-8.26 (m, 2H) 7.64-7.88 (m, 3H) 7.50-7.64 (m, 2H) 7.18-7.43 (m, 3H) 7.02 (d, 1H) 6.91 (t, 1H) 6.52-6.63 (m, 1H) 6.42 (d, 1H) 5.38 (d, 1H) 5.20 (d, 1H) 5.09-5.17 (m, 1H) 4.83 (s, 2H) 4.01-4.19 (m, 1H) 3.48-3.87 (m, 3H) 3.34-3.47 (m, 1H) 3.06-3.22 (m, 1H) 2.31-2.40 (m, 1H) 2.22 (s, 3H) 1.77-2.09 (m, 4H)

$^1$H NMR (300 MHz, DMSO-d$_6$, diastereomer 2) □ ppm 8.11-8.26 (m, 2H) 7.64-7.88 (m, 3H) 7.50-7.64 (m, 2H) 7.18-7.43 (m, 3H) 7.02 (d, 1H) 6.91 (t, 1H) 6.52-6.63 (m, 1H) 6.42 (d, 1H) 5.38 (d, 1H) 5.20 (d, 1H) 5.09-5.17 (m, 1H) 4.87 (s, 2H) 4.01-4.19 (m, 1H) 3.48-3.87 (m, 3H) 3.34-3.47 (m, 1H) 3.06-3.22 (m, 1H) 2.31-2.40 (m, 1H) 2.24 (s, 3H) 1.77-2.09 (m, 4H);

LC-MS (ESI POS): 509.15 (M+).

Example 25

Preparation of (3R)-1-((5-phenyl-1,2,4-oxadiazol-3-yl)methyl)-3-(2-(phenylamino)-2-(thiophen-2-yl)acetoxy)-1-azoniabicyclo[2.2.2]octane 2,2,2-trifluoroacetate (C80)

Scheme 26

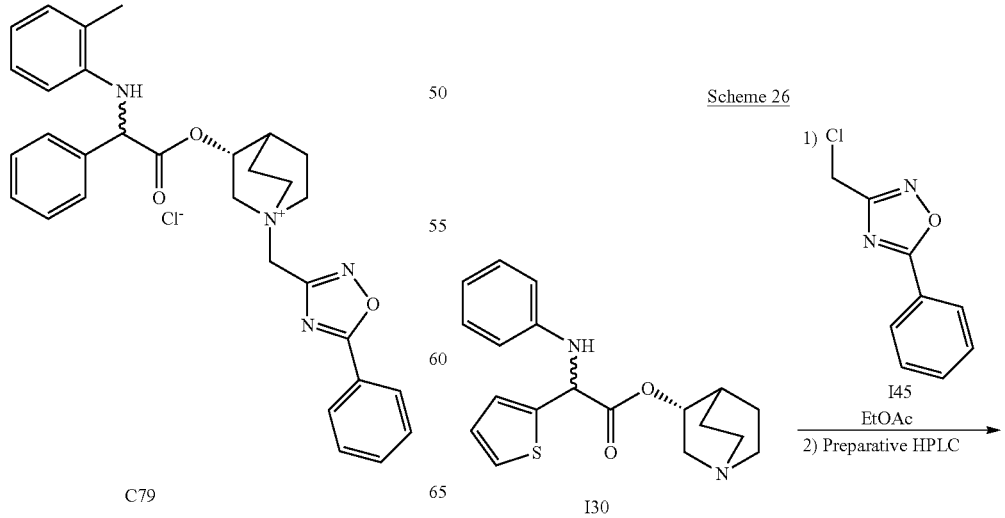

C79

I30

-continued

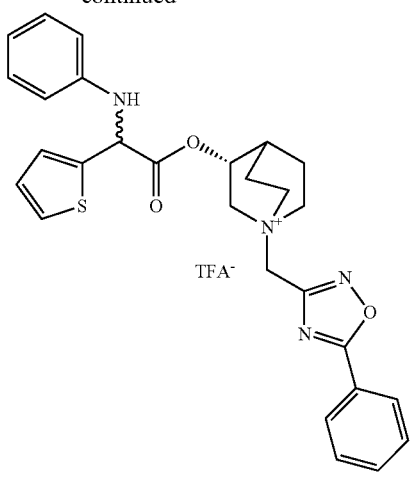

C80

3-(Chloromethyl)-5-phenyl-1,2,4-oxadiazole (I45) (7.39 mg, 0.04 mmol) was added to a solution of (R)-quinuclidin-3-yl 2-(phenylamino)-2-(thiophen-2-yl)acetate (I30) (13 mg, 0.04 mmol) in EtOAc (2 ml). The reaction mixture was stirred at room temperature overnight. Then solvent was removed under reduced pressure, and the crude product was purified by preparative HPLC to obtain (3R)-1-((5-phenyl-1,2,4-oxadiazol-3-yl)methyl)-3-(2-(phenylamino)-2-(thiophen-2-yl)acetoxy)-1-azoniabicyclo[2.2.2]octane 2,2,2-trifluoroacetate (12.3 mg, 52.7% yield, mixture of diastereomers).

$^1$H NMR (300 MHz, CHLOROFORM-d, diastereomer 1) δ ppm 8.08-8.23 (m, 2H) 7.48-7.75 (m, 3H) 7.06-7.26 (m, 4H) 6.84-7.01 (m, 1H) 6.72-6.83 (m, 1H) 6.60-6.72 (m, 2H) 5.43 (s, 1H) 5.29-5.40 (m, 1H) 4.91 (d, 1H) 4.79 (d, 1H) 4.09-4.24 (m, 1H) 3.89 (d, 1H) 3.69-3.84 (m, 1H) 3.40 (d, 1H) 3.02-3.23 (m, 1H) 2.35-2.58 (m, 1H) 1.98-2.35 (m, 4H) 1.59-1.93 (m, 1H)

$^1$H NMR (300 MHz, CHLOROFORM-d, diastereomer 1) δ ppm 8.08-8.23 (m, 2H) 7.53-7.75 (m, 3H) 7.06-7.26 (m, 4H) 6.92-7.01 (m, 1H) 6.72-6.81 (m, 1H) 6.60-6.72 (m, 2H) 5.45 (s, 1H) 5.29-5.40 (m, 1H) 4.94-5.10 (m, 2H) 4.26-4.40 (m, 1H) 3.89 (d, 1H) 3.49-3.67 (m, 1H) 3.40 (d, 1H) 3.02-3.23 (m, 1H) 2.35-2.58 (m, 1H) 1.98-2.35 (m, 4H) 1.59-1.93 (m, 1H)

LC-MS (ESI POS): 501.17 (M$^+$).

Final compound listed in Table 4 was prepared as previously described for C80, by alkylation of intermediate I25 with I45.

TABLE 4

| Compound | Structure | Yield | Analytical |
|---|---|---|---|
| C81 | Mixture of diastereomer | 22% | LC-MS (ESI POS): 509.22 (M+) $^1$H NMR (300 MHz, CHLOROFORM-d) δ ppm 8.06-8.25 (m, 2 H) 7.52-7.75 (m, 5 H) 7.43-7.52 (m, 3 H) 7.31-7.40 (m, 5 H) 5.21-5.39 (m, 1 H) 4.75-4.94 (m, 3 H) 4.39 (d, 1 H) 4.26 (d, 1 H) 4.08-4.23 (m, 2 H) 3.90 (d, 1 H) 3.60-3.84 (m, 2 H) 3.37-3.59 (m, 1 H) 2.23-2.62 (m, 2 H) 1.97-2.15 (m, 2 H) 1.75-1.97 (m, 1 H) |

Example 26

Preparation of (3R)-3-(2-(2-(methoxycarbonyl)thiophen-3-ylamino)-2-(6-methoxypyridin-3-yl)acetoxy)-1-((5-phenyl-1,2,4-oxadiazol-3-yl)methyl)-1-azoniabicyclo[2.2.2]octane 2,2,2-trifluoroacetate (C82)

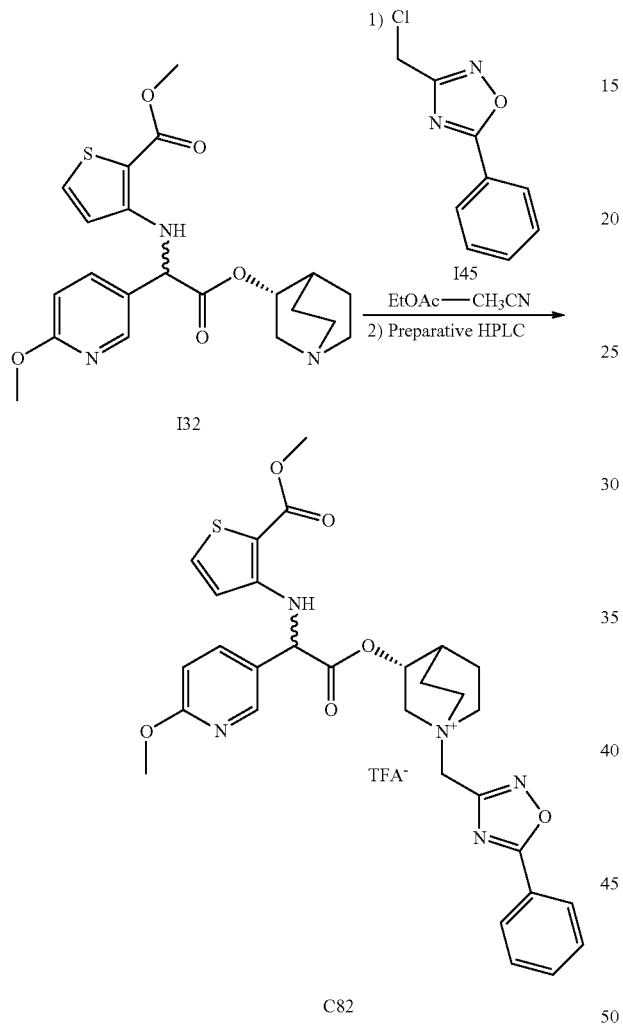

To a solution of methyl 3-(1-(6-methoxypyridin-3-yl)-2-oxo-2-((R)-quinuclidin-3-yloxy)ethylamino)thiophene-2-carboxylate (I32) (60 mg, 0.14 mmol, mixture of diastereomers) in EtOAc (3 ml) and acetonitrile (3 ml), was added 5-(chloromethyl)-3-phenyl-1,2,4-oxadiazole (I45) (29.8 mg, 0.15 mmol), and the reaction mixture was stirred at room temperature for 15 hours. Then the solvent was evaporated, and the crude product was purified by preparative HPLC to obtain (3R)-3-(2-(2-(methoxycarbonyl)thiophen-3-ylamino)-2-(6-methoxypyridin-3-yl)acetoxy)-1-((5-phenyl-1,2,4-oxadiazol-3-yl)methyl)-1-azoniabicyclo[2.2.2]octane 2,2,2-trifluoroacetate (60 mg, 61.3% yield, mixture of diastereomers).

$^1$H NMR (300 MHz, DMSO-$d_6$) δ ppm 8.25-8.40 (m, 1H) 7.99-8.13 (m, 2H) 7.52-7.84 (m, 6H) 6.78-6.92 (m, 1H) 6.69-6.78 (m, 1H) 5.57-5.77 (m, 1H) 5.13-5.23 (m, 1H) 5.06 (br. s., 2H) 4.05-4.20 (m, 1H) 3.84 (s, 3H) 3.76-3.81 (m, 3H) 3.38-3.76 (m, 5H) 2.33-2.45 (m, 1H) 1.99-2.15 (m, 1H) 1.74-1.99 (m, 3H);

LC-MS (ESI POS): 590.2 (M$^+$).

Example 27

Preparation of (3R)-1-methyl-1-((5-phenyl-1,2,4-oxadiazol-3-yl)methyl)-3-(2-phenyl-2-(phenylamino)acetoxy)pyrrolidinium 2,2,2-trifluoroacetate (C83)

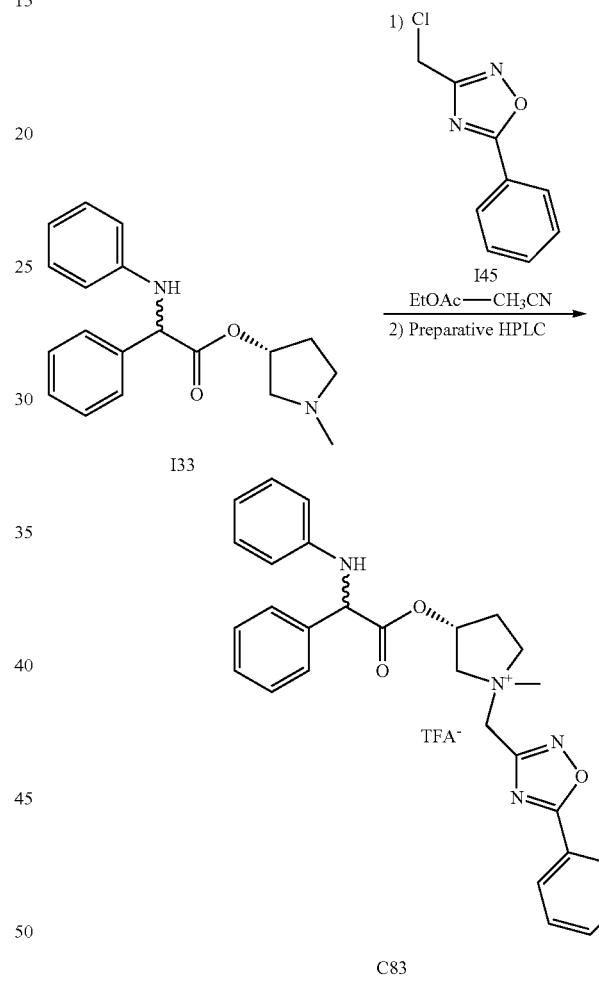

3-(Chloromethyl)-5-phenyl-1,2,4-oxadiazole (I45) (34.3 mg, 0.18 mmol) was added to a solution of (R)-1-methylpyrrolidin-3-yl 2-phenyl-2-(phenylamino)acetate (I33) (54.7 mg, 0.18 mmol) in EtOAc (2 ml). The reaction was stirred at room temperature overnight, then the solvent was removed under reduced pressure. The crude was purified by preparative HPLC to obtain (3R)-1-methyl-1-((5-phenyl-1,2,4-oxadiazol-3-yl)methyl)-3-(2-phenyl-2-(phenylamino)acetoxy)pyrrolidinium 2,2,2-trifluoroacetate (12 mg, 12% yield, mixture of diastereomers).

$^1$H NMR (300 MHz, Chloroform-d) δ ppm 8.08-8.25 (m, 2H) 7.43-7.81 (m, 5H) 7.29-7.43 (m, 3H) 7.02-7.17 (m, 2H) 6.65-6.79 (m, 1H) 6.61 (d, 2H) 5.55-5.77 (m, 1H) 5.08-5.30 (m, 2H) 4.53-4.81 (m, 2H) 4.18-4.43 (m, 2H) 3.94-4.09 (m, 2H) 3.78-3.94 (m, 1H) 3.34-3.55 (m, 3H) 2.76-3.04 (m, 1H);

LC-MS (ESI POS): 469.19 (M$^+$).

Example 28

Preparation of (R)-1-((5-(4-fluorophenyl)-1,2,4-oxadiazol-3-yl)methyl)-3-((R)-2-phenyl-2-(phenylamino)acetoxy)-1-azoniabicyclo[2.2.2]octane 2,2,2-trifluoroacetate (Diastereomer 1 of C84)

Scheme 29

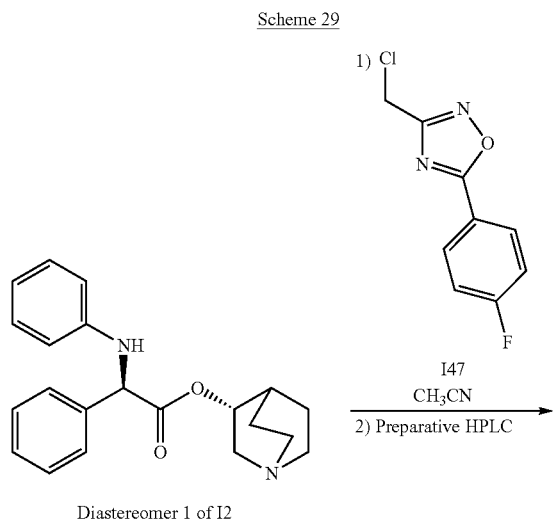

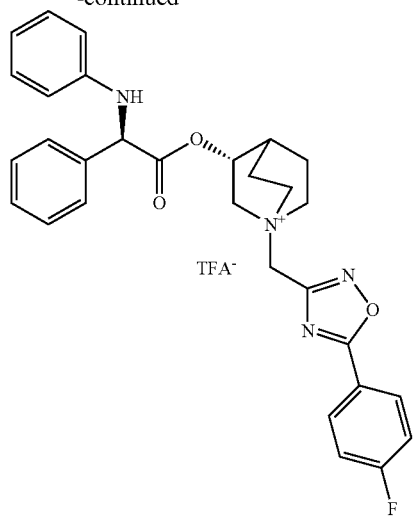

Diastereomer 1 of C84

3-(Chloromethyl)-5-(4-fluorophenyl)-1,2,4-oxadiazole (I47) (37.9 mg, 0.18 mmol) was added to a solution of (R)—((R)-quinuclidin-3-yl) 2-phenyl-2-(phenylamino)acetate (diastereomer 1 of I2) (60 mg, 0.18 mmol) in acetonitrile (2 ml). The reaction mixture was stirred at room temperature overnight. The solvent was evaporated, and the crude product was purified by preparative HPLC to get (R)-1-((5-(4-fluorophenyl)-1,2,4-oxadiazol-3-yl)methyl)-3-((R)-2-phenyl-2-(phenylamino)acetoxy)-1-azoniabicyclo[2.2.2]octane 2,2,2-trifluoroacetate (72.1 mg, 64.5% yield).

$^1$H NMR (300 MHz, DMSO-$d_6$) δ ppm 8.15-8.34 (m, 2H), 7.47-7.64 (m, 4H), 7.16-7.44 (m, 3H), 7.01-7.13 (m, 2H), 6.66-6.77 (m, 2H), 6.52-6.63 (m, 1H), 6.34 (br. s., 1H), 5.34 (s, 1H), 5.07-5.22 (m, 1H), 4.76 (s, 2H), 3.99-4.12 (m, 1H), 3.45-3.67 (m, 3H), 3.21-3.32 (m, 1H), 2.99-3.21 (m, 1H), 2.30-2.41 (m, 1H), 1.67-2.04 (m, 4H);

LC-MS (ESI POS): 513.32 (MH+).

Final compounds listed in Table 5 were prepared as previously described for C84, by alkylation of diastereomer 1 of I2 with I46 and I48.

TABLE 5

| Compound | Structure | Yield | Analytical |
|---|---|---|---|
| Diastereomer 1 of C85 | Single diastereomer | 22% | LC-MS (ESI POS): 509.3 (M+) <br> 1H NMR (300 MHz, DMSO-d6) δ ppm 7.87-8.18 (m, 2 H), 7.47-7.63 (m, 4 H), 7.20-7.41 (m, 3 H), 6.92-7.13 (m, 2 H), 6.65-6.80 (m, 2 H), 6.47-6.63 (m, 1 H), 6.34 (d, 1 H), 5.35 (s, 1 H), 5.13 (s, 1 H), 4.74 (s, 2 H), 3.84-4.13 (m, 1 H), 3.46-3.84 (m, 5 H), 2.46 (br. s., 3 H), 2.30-2.37 (m, 1 H), 1.59-2.10 (m, 4 H) |

TABLE 5-continued

| Compound | Structure | Yield | Analytical |
|---|---|---|---|
| Diastereomer 1 of C86 | Single diastereomer | 30% | LC-MS (ESI POS): 529.28 (M+)<br>$^1$H NMR (300 MHz, DMSO-$d_6$) δ ppm 8.18 (m, 2 H), 7.79 (m, 2 H), 7.46-7.67 (m, 2 H), 7.18-7.46 (m, 3 H), 6.90-7.18 (m, 2 H), 6.65-6.80 (m, 2 H), 6.51-6.65 (m, 1 H), 6.14-6.49 (m, 1 H), 5.34 (br. s., 1 H), 5.00-5.26 (m, 1 H), 4.77 (s, 2 H), 3.91-4.20 (m, 1 H), 3.57-3.72 (m, 2 H), 3.20-3.31 (m, 2 H), 2.95-3.20 (m, 1 H), 2.29-2.40 (m, 1 H), 1.92-2.12 (m, 1 H), 1.60-1.92 (m, 3 H) |

Example 29

Preparation of (R)-1-((5-(3-methoxyphenyl)-1,2,4-oxadiazol-3-yl)methyl)-3-((R)-2-phenyl-2-(phenylamino)acetoxy)-1-azoniabicyclo[2.2.2]octane chloride (Diastereomer 1 of C87)

Scheme 30

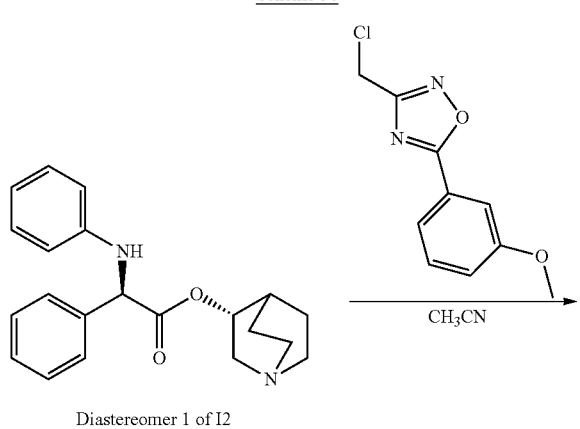

Diastereomer 1 of I2

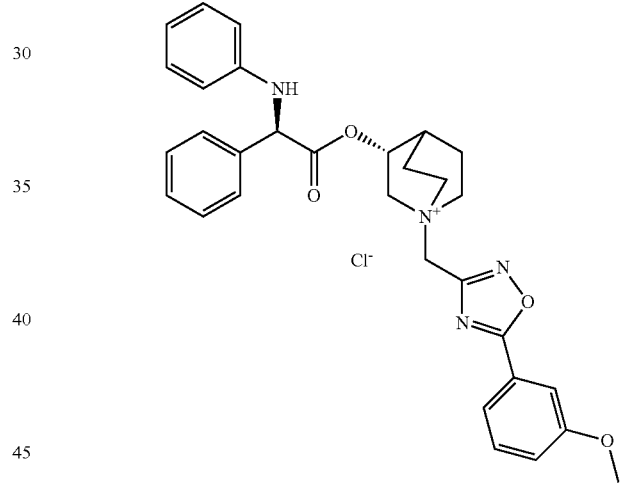

Diastereomer 1 of C87

3-(Chloromethyl)-5-(3-methoxyphenyl)-1,2,4-oxadiazole (33.4 mg, 0.15 mmol) was added to a solution of (R)—((R)-quinuclidin-3-yl) 2-phenyl-2-(phenylamino)acetate (50.0 mg, 0.15 mmol) in acetonitrile (2 ml). The reaction was stirred at room temperature overnight. The solvent was evaporated, and the resulting solid was triturated with Et$_2$O (2 ml) to obtain (R)-1-((5-(3-methoxyphenyl)-1,2,4-oxadiazol-3-yl)methyl)-3-((R)-2-phenyl-2-(phenylamino)acetoxy)-1-azoniabicyclo[2.2.2]octane chloride (82.3 mg, 99% yield).

$^1$H NMR (300 MHz, DMSO-$d_6$) δ ppm 7.73-7.81 (m, 1H), 7.59-7.69 (m, 2H), 7.48-7.57 (m, 2H), 7.21-7.45 (m, 4H), 7.00-7.12 (m, 2H), 6.67-6.77 (m, 2H), 6.52-6.64 (m, 1H), 6.39 (d, 1H), 5.34 (d, 1H), 5.05-5.20 (m, 1H), 4.80 (s, 2H), 3.97-4.19 (m, 1H), 3.89 (s, 3H), 3.47-3.81 (m, 3H), 3.33-3.40 (m, 1H), 2.98-3.22 (m, 1H), 2.29-2.38 (m, 1H), 1.69-2.04 (m, 4H);

LC-MS (ESI POS): 525.46 (M+).

Final compounds C88 and C89 in Table 6 were prepared as previously described for C87, by alkylation of diastereomer 1 of I2 with the suitable commercially available alkylating agents. All the other compounds listed in Table 6 were prepared by alkylation of diastereomer 1 of I2, I36 and diastereomer 1 of I39 with I49, I50, I53, I54, I55, I56, I57 and I58, but using ethyl acetate as the solvent instead of acetonitrile.

TABLE 6

| Compound | Structure | Yield | Analytical |
|---|---|---|---|
| Diastereomer 1 of C88 | Single diastereomer | 94% | LC-MS (ESI POS): 525.45 (M+)<br>$^1$H NMR (300 MHz, DMSO-$d_6$) δ ppm 8.05 (dd, 1 H), 7.67-7.83 (m, 1 H), 7.47-7.59 (m, 2 H), 7.15-7.44 (m, 5 H), 6.98-7.12 (m, 2 H), 6.66-6.77 (m, 2 H), 6.51-6.63 (m, 1 H), 6.37 (d, 1 H), 5.34 (d, 1 H), 5.08-5.17 (m, 1 H), 4.78 (s, 2 H), 4.00-4.14 (m, 1 H), 3.99 (s, 3 H), 3.43-3.75 (m, 3 H), 3.31-3.37 (m, 1 H), 2.95-3.18 (m, 1 H), 2.29-2.39 (m, 1 H), 1.53-2.15 (m, 4 H) |
| Diastereomer 1 of C89 | Single diastereomer | 82% | LC-MS (ESI POS): 508.46 (M+)<br>$^1$H NMR (300 MHz, DMSO-$d_6$) δ ppm 7.96-8.07 (m, 2 H), 7.58-7.71 (m, 2 H), 7.42-7.54 (m, 3 H), 7.19-7.36 (m, 3 H), 6.95-7.09 (m, 2 H), 6.65-6.80 (m, 2 H), 6.52-6.61 (m, 1 H), 6.34 (d, 1 H), 5.33 (d, 1 H), 5.05-5.22 (m, 1 H), 4.58 (s, 2 H), 3.85-4.10 (m, 1 H), 3.34-3.65 (m, 3 H), 2.97-3.13 (m, 1 H), 2.79-2.97 (m, 1 H), 2.40 (s, 3 H), 2.29-2.35 (m, 1 H), 1.64-2.10 (m, 4 H) |

TABLE 6-continued

| Compound | Structure | Yield | Analytical |
|---|---|---|---|
| Diastereomer 1 of C90 | 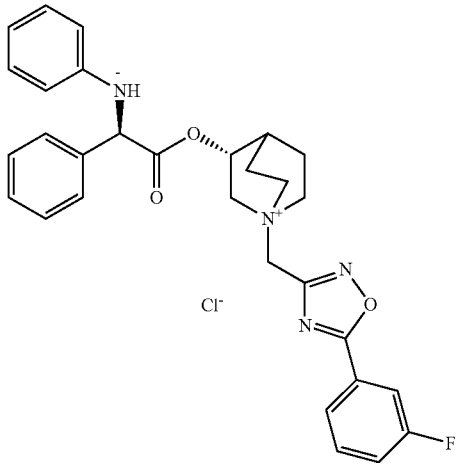 Single diastereomer | 92% | LC-MS (ESI POS): 513.39 (M+)<br>$^1$H NMR (300 MHz, DMSO-$d_6$) δ ppm 8.03 (dt, 1 H), 7.92-8.00 (m, 1 H), 7.78 (td, 1 H), 7.61-7.73 (m, 1 H), 7.48-7.58 (m, 2 H), 7.22-7.42 (m, 3 H), 7.00-7.13 (m, 2 H), 6.65-6.79 (m, 2 H), 6.52-6.63 (m, 1 H), 6.38 (d, 1 H), 5.34 (d, 1 H), 5.06-5.18 (m, 1 H), 4.81 (s, 2 H), 3.98-4.15 (m, 1 H), 3.45-3.76 (m, 3 H), 3.31-3.41 (m, 1 H), 3.02-3.23 (m, 1 H), 2.29-2.37 (m, 1 H), 1.69-2.10 (m, 4 H) |
| Diastereomer 1 of C91 | 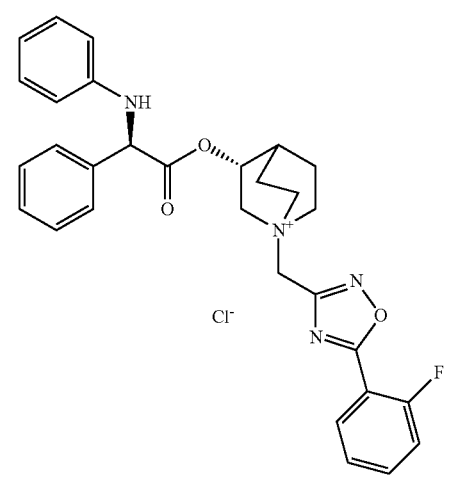 Single diastereomer | 66.5% | LC-MS (ESI POS): 513.39 (M+)<br>$^1$H NMR (300 MHz, DMSO-$d_6$) δ ppm 8.19 (td, 1 H), 7.79-7.93 (m, 1 H), 7.47-7.67 (m, 4 H), 7.21-7.41 (m, 3 H), 6.99-7.13 (m, 2 H), 6.65-6.77 (m, 2 H), 6.52-6.65 (m, 1 H), 6.36 (d, 1 H), 5.34 (d, 1 H), 5.03-5.18 (m, 1 H), 4.82 (s, 2 H), 3.91-4.19 (m, 1 H), 3.44-3.80 (m, 4 H), 3.02-3.21 (m, 1 H), 2.28-2.39 (m, 1 H), 1.64-2.13 (m, 4 H) |
| Diastereomer 1 of C92 | 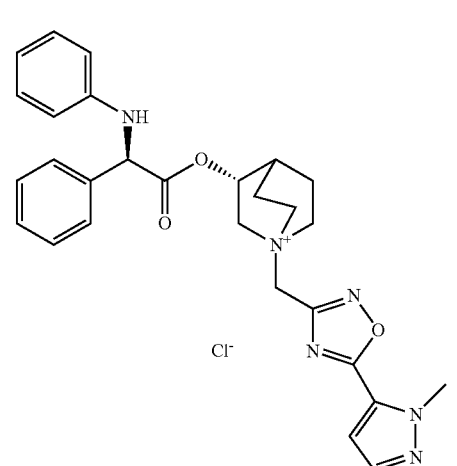 Single diastereomer | 90% | LC-MS (ESI POS): 513.28 (M+)<br>$^1$H NMR (300 MHz, DMSO-$d_6$) δ ppm 7.46-7.63 (m, 2 H), 7.19-7.43 (m, 3 H), 6.94-7.17 (m, 3 H), 6.72 (d, 2 H), 6.58 (t, 1 H), 6.38 (d, 1 H), 5.34 (d, 1 H), 4.98-5.23 (m, 1 H), 4.80 (dd, 2 H), 4.14 (s, 3 H), 3.97-4.12 (m, 1 H), 3.44-3.73 (m, 3 H), 3.33 (br. s., 1 H), 2.98-3.22 (m, 1 H), 2.30-2.39 (m, 1 H), 2.28 (s, 3 H), 1.75-2.07 (m, 4 H) |

TABLE 6-continued

| Compound | Structure | Yield | Analytical |
|---|---|---|---|
| Diastereomer 1 of C93 | Single diastereomer | 69.2% | LC-MS (ESI POS): 501.35 (M+)<br>$^1$H NMR (300 MHz, DMSO-d$_6$) δ ppm 7.49-7.65 (m, 2 H), 7.24-7.48 (m, 3 H), 7.00-7.16 (m, 2 H), 6.67-6.80 (m, 2 H), 6.52-6.67 (m, 1 H), 6.38 (d, 1 H), 5.34 (d, 1 H), 4.99-5.21 (m, 1 H), 4.69 (s, 2 H), 3.97 (dd, 1 H), 3.34-3.73 (m, 4 H), 3.05-3.20 (m, 2 H), 2.31 (br. s., 1 H), 1.82-2.18 (m, 5 H), 1.70-1.82 (m, 3 H), 1.25-1.70 (m, 6 H) |
| Diastereomer 1 of C94 | Single diastereomer | 87% | LC-MS (ESI POS): 502.23 (M+)<br>$^1$H NMR (300 MHz, DMSO-d$_6$) δ ppm 8.40 (d, 1 H), 8.31-8.36 (m, 1 H), 7.49-7.61 (m, 2 H), 7.23-7.42 (m, 3 H), 7.06 (dd, 2 H), 6.66-6.78 (m, 2 H), 6.58 (t, 1 H), 6.37 (d, 1 H), 5.34 (d, 1 H), 5.02-5.21 (m, 1 H), 4.83 (s, 2 H), 3.95-4.15 (m, 1 H), 3.44-3.78 (m, 3 H), 3.33 (br. s., 1 H), 3.03-3.23 (m, 1 H), 2.33 (br. s., 1 H), 1.74-2.06 (m, 4 H) |
| Diastereomer 1 of C95 | Single diastereomer | 99% | LC-MS (ESI POS): 525.35 (M+)<br>$^1$H NMR (300 MHz, DMSO-d$_6$) δ ppm 7.88-8.26 (m, 2 H), 7.44-7.65 (m, 2 H), 7.14-7.44 (m, 5 H), 6.93-7.14 (m, 2 H), 6.64-6.81 (m, 2 H), 6.49-6.64 (m, 1 H), 6.40 (d, 1 H), 5.34 (d, 1 H), 5.01-5.23 (m, 1 H), 4.77 (s, 2 H), 4.07 (dd, 1 H), 3.91 (s, 3 H), 3.44-3.76 (m, 3 H), 3.33-3.38 (m, 1 H), 2.95-3.19 (m, 1 H), 2.32 (br. s., 1 H), 1.72-2.12 (m, 4 H) |

TABLE 6-continued

| Compound | Structure | Yield | Analytical |
|---|---|---|---|
| Diastereomer 1 of C96<br><br>Single diastereomer | | 99% | LC-MS (ESI POS): 537.32 (M+)<br>$^1$H NMR (300 MHz, DMSO-d$_6$) δ ppm 8.02 (d, 1 H), 7.96 (dd, 1 H), 7.46-7.58 (m, 2 H), 7.20-7.43 (m, 3 H), 6.94-7.13 (m, 3 H), 6.65-6.79 (m, 2 H), 6.50-6.64 (m, 1 H), 6.39 (d, 1 H), 5.34 (d, 1 H), 5.06-5.20 (m, 1 H), 4.74 (s, 2 H), 4.71 (t, 2 H), 3.93-4.15 (m, 1 H), 3.44-3.74 (m, 3 H), 3.31-3.39 (m, 3 H), 2.95-3.19 (m, 1 H), 2.27-2.40 (m, 1 H), 1.68-2.10 (m, 4 H) |
| Diastereomer 1 of C97<br><br>Single diastereomer | | 67% | LC-MS (ESI POS): 551.30 (M+)<br>$^1$H NMR (300 MHz, DMSO-d$_6$) δ ppm 8.58 (s, 1 H), 8.18-8.27 (m, 1 H), 8.09-8.18 (m, 1 H), 7.47-7.73 (m, 4 H), 7.22-7.42 (m, 3 H), 7.00-7.11 (m, 2 H), 6.67-6.79 (m, 2 H), 6.53-6.63 (m, 1 H), 6.36 (d, 1 H), 5.35 (d, 1 H), 5.05-5.21 (m, 1 H), 4.79 (s, 2 H), 3.94-4.20 (m, 1 H), 3.44-3.77 (m, 3 H), 3.31-3.38 (m, 1 H), 2.97-3.19 (m, 1 H), 2.30-2.38 (m, 1 H), 1.68-2.14 (m, 4 H) |
| C98<br><br>Mixture of diastereomer | | 81% | LC-MS (ESI POS): 509.23 (M+)<br>$^1$H NMR (300 MHz, DMSO-d$_6$) δ ppm 8.10-8.28 (m, 2 H), 7.74-7.84 (m, 1 H), 7.63-7.74 (m, 2 H), 7.30-7.47 (m, 5 H), 7.16-7.26 (m, 2 H), 6.84-7.03 (m, 2 H), 6.67-6.79 (m, 1 H), 5.93 and 5.94 (s, 1 H), 5.13-5.31 (m, 1 H), 4.84 (s, 2 H), 3.97-4.24 (m, 1 H), 3.46-3.78 (m, 5 H), 2.74 and 2.75 (s, 3 H), 2.19-2.32 (m, 1 H), 1.54-2.05 (m, 4 H) |

TABLE 6-continued
| Compound | Structure | Yield | Analytical |
|---|---|---|---|
| Diastereomer 1 of C99 | 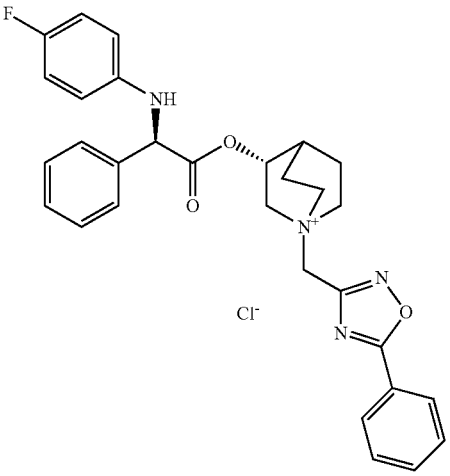<br>Single diastereomer | 58% | LC-MS (ESI POS): 513.22 (M+)<br>$^1$H NMR (300 MHz, DMSO-d$_6$) δ ppm 8.04-8.26 (m, 2 H), 7.76-7.84 (m, 1 H), 7.64-7.76 (m, 2 H), 7.46-7.59 (m, 2 H), 7.18-7.44 (m, 3 H), 6.81-6.97 (m, 2 H), 6.60-6.77 (m, 2 H), 6.35 (d, 1 H), 5.32 (d, 1 H), 5.04-5.17 (m, 1 H), 4.81 (s, 2 H), 3.94-4.15 (m, 1 H), 3.48-3.77 (m, 3 H), 3.05-3.23 (m, 2 H), 2.30-2.38 (m, 1 H), 1.75-2.15 (m, 4 H) |
| C100 | 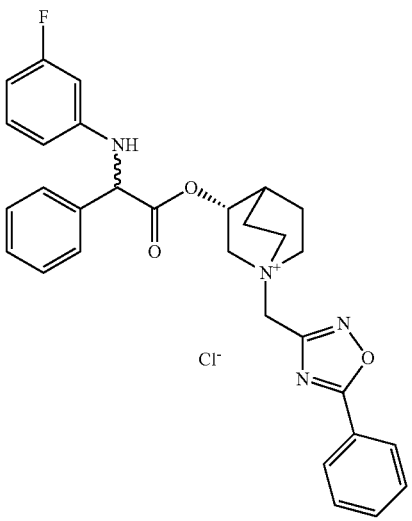<br>Mixture of diastereomer | 83% | LC-MS (ESI POS): 513.33 (M+)<br>$^1$H NMR (300 MHz, DMSO-d$_6$) δ ppm 8.08-8.22 (m, 2 H), 7.64-7.90 (m, 3 H), 7.46-7.60 (m, 2 H), 7.20-7.45 (m, 3 H), 6.99-7.12 (m, 1 H), 6.77 and 6.81 (d, 1 H), 6.46-6.60 (m, 2 H), 6.28-6.44 (m, 1 H), 5.36 and 5.40 (d, 1 H), 5.04-5.19 (m, 1 H), 4.83 and 4.87 (s, 2 H), 3.95-4.21 (m, 1 H), 3.47-3.83 (m, 4 H), 3.10-3.26 (m, 1 H), 2.08-2.17 and 2.29-2.38 (m, 1 H), 1.39-2.07 (m, 4 H) |

TABLE 6-continued

| Compound | Structure | Yield | Analytical |
|---|---|---|---|
| C101 | 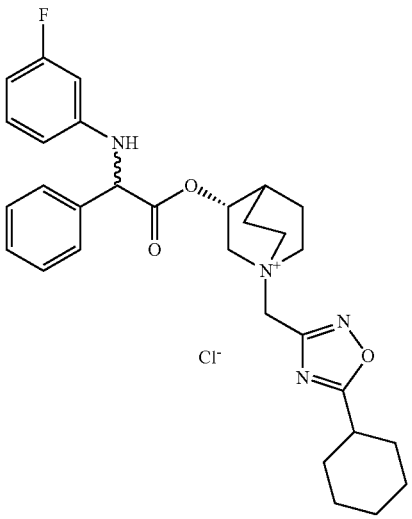<br>Mixture of diastereomer | 23% | LC-MS (ESI POS): 519.32 (M+)<br>$^1$H NMR (300 MHz, DMSO-$d_6$) δ ppm 7.48-7.60 (m, 2 H), 7.26-7.48 (m, 3 H), 6.97-7.16 (m, 1 H), 6.76 (d, 1 H), 6.45-6.62 (m, 2 H), 6.28-6.44 (m, 1 H), 5.35 and 5.39 (d, 1 H), 5.01-5.22 (m, 1 H), 4.72 and 4.76 (s, 2 H), 3.85-4.09 (m, 1 H), 3.32-3.75 (m, 5 H), 3.11 (tt, 1 H), 2.07-2.16 and 2.22-2.40 (m, 1 H), 1.00-2.16 (m, 14 H) |

Example 30

Preparation of (R)-3-((R)-2-phenyl-2-(phenylamino)acetoxy)-1-((5-(pyridin-4-yl)-1,2,4-oxadiazol-3-yl)methyl)-1-azoniabicyclo[2.2.2]octane chloride (Diastereomer 1 of C102)

Scheme 31

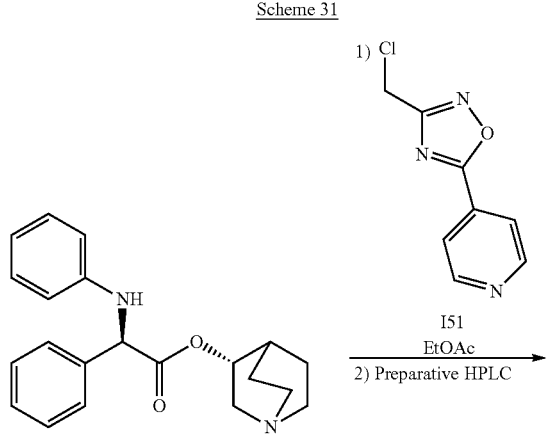

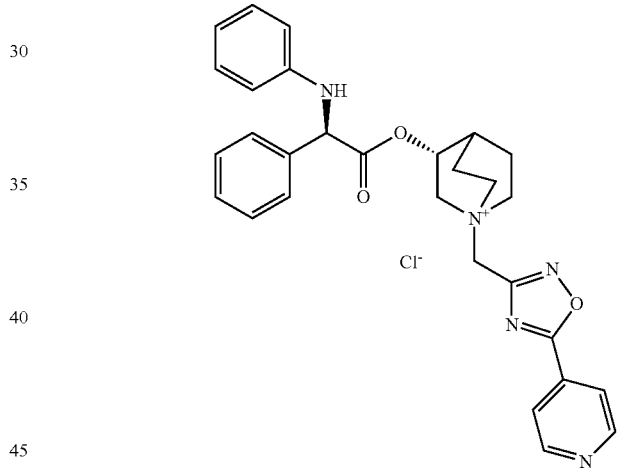

Diastereomer 1 of C102

3-(Chloromethyl)-5-(pyridin-4-yl)-1,2,4-oxadiazole (I51) (45.0 mg, 0.23 mmol) was added to a solution of (R)—((R)-quinuclidin-3-yl) 2-phenyl-2-(phenylamino)acetate (diastereomer 1 of I2) (50 mg, 0.15 mmol) in EtOAc (2 ml). The reaction mixture was heated under microwave irradiation at 80° C. for 3 hours. The solvent was evaporated, and the residue was triturated with Et$_2$O, filtered and dried. The product was purified by flash-chromatography (DCM/MeOH=97/3 to 9/1) and then by preparative HPLC (eluents: CH$_3$CN/H$_2$O) to obtain (R)-3-((R)-2-phenyl-2-(phenylamino)acetoxy)-1-((5-(pyridin-4-yl)-1,2,4-oxadiazol-3-yl)methyl)-1-azoniabicyclo[2.2.2]octane chloride (32.3 mg, 29.0% yield).

$^1$H NMR (300 MHz, DMSO-$d_6$) δ ppm 8.88-9.02 (m, 2H), 8.02-8.14 (m, 2H), 7.49-7.61 (m, 2H), 7.25-7.45 (m, 3H), 7.01-7.11 (m, 2H), 6.66-6.80 (m, 2H), 6.52-6.64 (m, 1H), 6.38 and 6.39 (d, 1H), 5.30 and 5.34 (d, 1H), 5.04-5.18 (m, 1H), 4.85 and 4.91 (s, 2H), 3.97-4.18 (m, 1H), 3.35-3.80 (m, 5H), 2.02-2.18 and 2.30-2.38 (m, 1H), 1.32-2.04 (m, 4H); LC-MS (ESI POS): 496.38 (M+).

Example 31

Preparation of (R)-1-((5-benzyl-1,2,4-oxadiazol-3-yl)methyl)-3-((R)-2-phenyl-2-(phenylamino)acetoxy)-1-azoniabicyclo[2.2.2]octane chloride (Diastereomer 1 of C103)

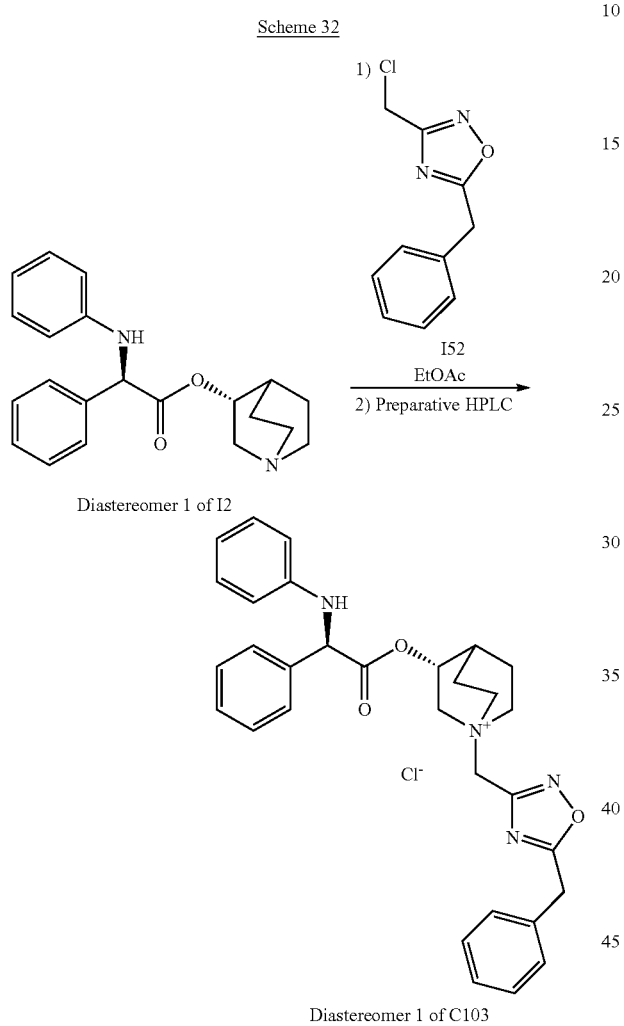

5-Benzyl-3-(chloromethyl)-1,2,4-oxadiazole (I52) (34.1 mg, 0.16 mmol) was added to a solution of (R)—((R)-quinuclidin-3-yl) 2-phenyl-2-(phenylamino)acetate (diastereomer 1 of I2) (50 mg, 0.15 mmol) in EtOAc (2 ml). The reaction mixture was stirred at room temperature overnight. The solvent was evaporated and residue was triturated in Et$_2$O. The product was further purified by preparative HPLC(CH$_3$CN/H$_2$O) to obtain (R)-1-((5-benzyl-1,2,4-oxadiazol-3-yl)methyl)-3-((R)-2-phenyl-2-(phenylamino)acetoxy)-1-azoniabicyclo[2.2.2]octane chloride (35.3 mg, 43.6% yield).

$^1$H NMR (300 MHz, DMSO-d$_6$) δ ppm 7.48-7.65 (m, 2H), 7.22-7.47 (m, 8H), 7.01-7.13 (m, 2H), 6.68-6.77 (m, 2H), 6.52-6.66 (m, 1H), 6.38 (d, 1H), 5.34 (d, 1H), 5.02-5.17 (m, 1H), 4.69 (s, 2H), 4.46 (s, 2H), 3.89-4.08 (m, 1H), 3.37-3.64 (m, 4H), 2.92-3.17 (m, 1H), 2.22-2.38 (m, 1H), 1.64-2.05 (m, 4H);

LC-MS (ESI POS): 509.37 (M+).

Example 32

Preparation of (R)-1-((1H-benzo[d]imidazol-2-yl)methyl)-3-((R)-2-phenyl-2-(phenylamino)acetoxy)-1-azoniabicyclo[2.2.2]octane 2,2,2-trifluoroacetate (Diastereomer 1 of C104)

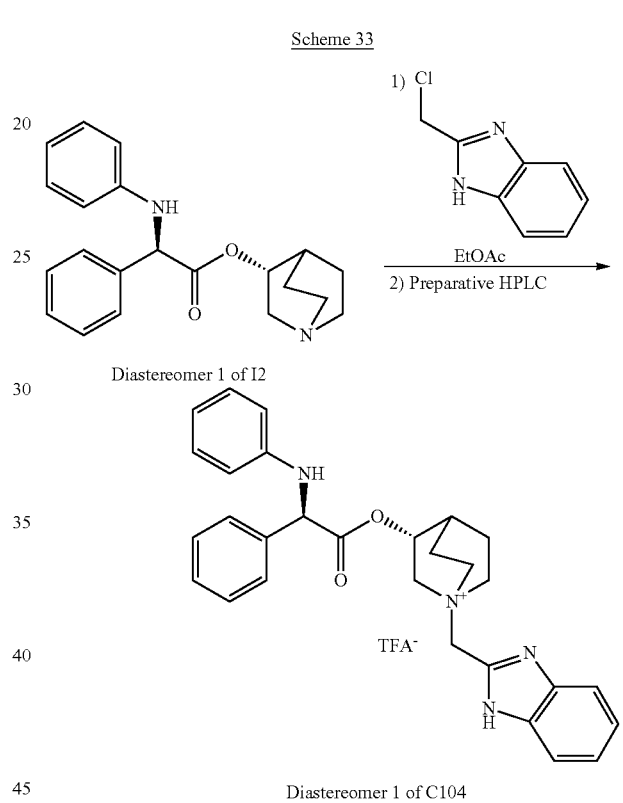

2-(Chloromethyl)-1H-benzo[d]imidazole (29.7 mg, 0.18 mmol) was added to a solution of (R)—((R)-quinuclidin-3-yl) 2-phenyl-2-(phenylamino)acetate (diastereomer 1 of I2) (60 mg, 0.18 mmol) in EtOAc (2 ml). The reaction mixture was stirred at room temperature overnight and then heated at 80° C. for 1 hour under microwave irradiation. The solvent was evaporated, and the crude product was first purified by flash-chromatography (DCM/MeOH=96/4 to 9/1) and then by preparative HPLC to obtain (R)-1-((1H-benzo[d]imidazol-2-yl)methyl)-3-((R)-2-phenyl-2-(phenylamino)acetoxy)-1-azoniabicyclo[2.2.2]octane 2,2,2-trifluoroacetate (46.3 mg, 44.7% yield).

$^1$H NMR (300 MHz, DMSO-d$_6$) δ ppm 7.61-7.77 (m, 2H), 7.41-7.54 (m, 2H), 7.27-7.39 (m, 2H), 7.14-7.27 (m, 3H), 6.87-7.10 (m, 2H), 6.61-6.80 (m, 2H), 6.47-6.60 (m, 1H), 6.30 (br. s., 1H), 5.32 (s, 1H), 4.98-5.19 (m, 1H), 4.47-4.71 (m, 2H), 3.91-4.07 (m, 1H), 3.42-3.68 (m, 4H), 3.26 (d, 1H), 2.79-3.03 (m, 1H), 2.19-2.37 (m, 1H), 1.74-2.10 (m, 4H);

LC-MS (ESI POS): 509.37 (M+).

Example 33

Preparation of (3R)-3-(2-(3-fluorophenylamino)-2-phenylacetoxy)-1-((5-(thiazol-2-yl)-1,2,4-oxadiazol-3-yl)methyl)-1-azoniabicyclo[2.2.2]octane chloride (C105)

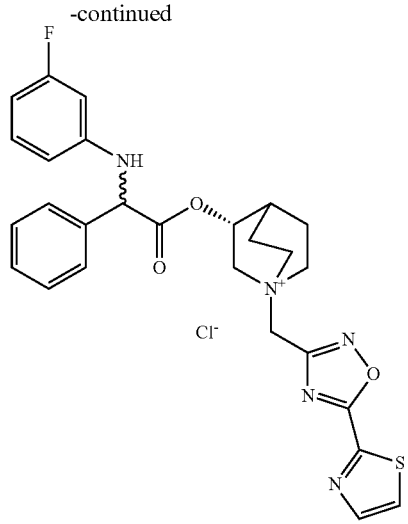

C105

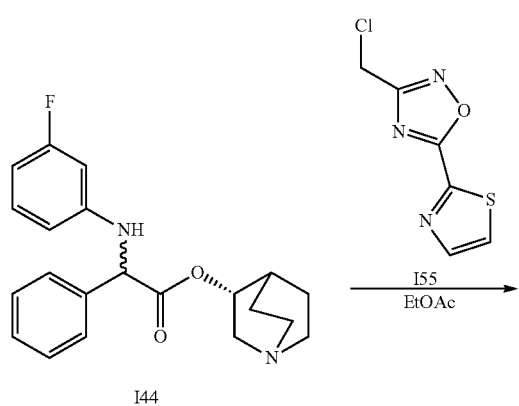

Scheme 34

To a solution of (R)-quinuclidin-3-yl 2-(3-fluorophenylamino)-2-phenylacetate (I41) (76 mg, 0.21 mmol) in EtOAc (5 mL), was added 3-(chloromethyl)-5-(thiazol-2-yl)-1,2,4-oxadiazole (I55) (43 mg, 0.21 mmol). The mixture was stirred at room temperature for 17 hours. Then the mixture was heated under microwave irradiation at 100° C. for 1 hour. The solvent was evaporated and the crude was triturated with $Et_2O$ and filtrated to collect (3R)-3-(2-(3-fluorophenylamino)-2-phenylacetoxy)-1-((5-(thiazol-2-yl)-1,2,4-oxadiazol-3-yl)methyl)-1-azoniabicyclo[2.2.2]octane chloride (36 mg, 30.4% yield, mixture of diastereomers).

$^1$H NMR (300 MHz, DMSO-$d_6$) δ ppm 8.39 (d, 1H), 8.32 (d, 1H), 7.48-7.62 (m, 2H), 7.25-7.44 (m, 3H), 6.94-7.15 (m, 1H), 6.74 and 6.78 (d, 1H), 6.43-6.59 (m, 2H), 6.24-6.43 (m, 1H), 5.34 and 5.39 (d, 1H), 5.06-5.20 (m, 1H), 4.86 and 4.89 (s, 2H), 3.94-4.19 (m, 1H), 3.31-3.81 (m, 5H), 2.07-2.16 and 2.28-2.39 (m, 1H), 1.43-2.06 (m, 4H);

LC-MS (ESI POS): 520.22 (M+).

Final compounds listed in Table 7 were prepared as previously described for C105, by alkylation of I41 and I43 with I53 and I45.

TABLE 7

| Compound | Structure | Yield | Analytical |
|---|---|---|---|
| C106 | (structure shown) Mixture of diastereomer | 23% | LC-MS (ESI POS): 531.29 (M+) <br> $^1$H NMR (300 MHz, DMSO-$d_6$) δ ppm 7.47-7.59 (m, 2 H), 7.18-7.46 (m, 3 H), 6.94-7.11 (m, 2 H), 6.74 and 6.79 (d, 1 H), 6.44-6.63 (m, 2 H), 6.22-6.43 (m, 1 H), 5.34 and 5.39 (d, 1 H), 5.03-5.21 (m, 1 H), 4.83 and 4.86 (s, 2 H), 4.13 and 4.14 (s, 3 H), 3.98-4.11 (m, 1 H), 3.31-3.78 (m, 5 H), 2.27 and 2.28 (s, 3 H), 2.09-2.16 and 2.31-2.38 (m, 1 H), 1.47-2.08 (m, 4 H) |

| Compound | Structure | Yield | Analytical |
|---|---|---|---|
| C107 | 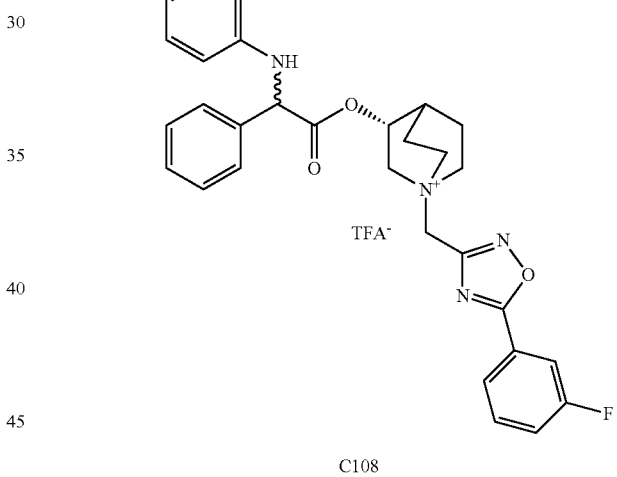  Mixture of diastereomer | 81% | LC-MS (ESI POS): 551.30 (M+)<br>$^1$H NMR (300 MHz, DMSO-$d_6$) δ ppm 8.13-8.25 (m, 2 H), 7.93-8.13 (m, 2 H), 7.87 and 7.89 (s, 1 H), 7.63-7.83 (m, 3 H), 7.32-7.50 (m, 2 H), 6.96-7.17 (m, 2 H), 6.69-6.86 (m, 2 H), 6.54-6.69 (m, 1 H), 6.46 and 6.48 (d, 1 H), 5.68-5.82 (m, 1 H), 5.06-5.23 (m, 1 H), 4.76 and 4.84 (s, 2 H), 3.95-4.19 (m, 1 H), 3.37-3.85 (m, 5 H), 2.01-2.13 and 2.30-2.38 (m, 1 H), 1.37-2.01 (m, 4 H) |

Example 34

Preparation of (3R)-1-((5-(3-fluorophenyl)-1,2,4-oxadiazol-3-yl)methyl)-3-(2-(3-fluorophenylamino)-2-phenylacetoxy)-1-azoniabicyclo[2.2.2]octane 2,2,2-trifluoroacetate (C108)

Scheme 35

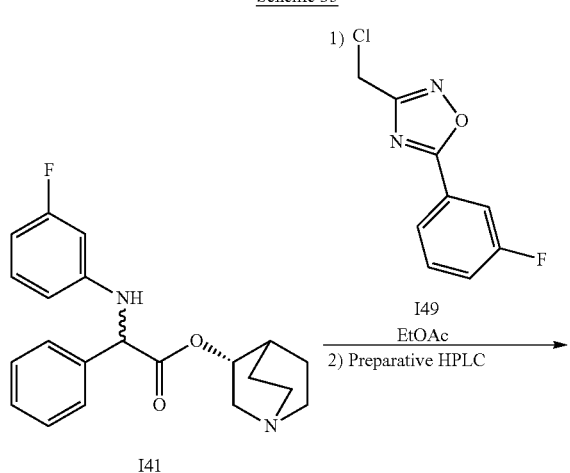

(R)-Quinuclidin-3-yl 2-(3-fluorophenylamino)-2-phenylacetate (I41) (89 mg, 0.25 mmol) and 3-(chloromethyl)-5-(3-fluorophenyl)-1,2,4-oxadiazole (I49) (53.5 mg, 0.25 mmol) were dissolved in EtOAc (3 ml). The mixture was stirred overnight, and then the solvent was evaporated. The crude product was purified by preparative HPLC to collect (3R)-1-((5-(3-fluorophenyl)-1,2,4-oxadiazol-3-yl)methyl)-3-(2-(3-fluorophenylamino)-2-phenylacetoxy)-1-azoniabicyclo[2.2.2]octane 2,2,2-trifluoroacetate (30.5 mg, 18.8% yield, mixture of diastereomers).

$^1$H NMR (300 MHz, DMSO-$d_6$) δ ppm 8.02 (dt, 1H), 7.96 (ddd, 1H), 7.72-7.84 (m, 1H), 7.60-7.72 (m, 1H), 7.48-7.59 (m, 2H), 7.21-7.48 (m, 3H), 6.99-7.14 (m, 1H), 6.65-6.82 (m, 1H), 6.45-6.59 (m, 2H), 6.25-6.41 (m, 1H), 5.27-5.45 (m, 0H), 5.01-5.21 (m, 1H), 4.82 and 4.85 (s, 2H), 3.94-4.18 (m, 1H), 3.46-3.78 (m, 3H), 2.97-3.24 (m, 2H), 2.09-2.19 and 2.31-2.40 (m, 1H), 1.40-2.07 (m, 4H);

LC-MS (ESI POS): 531.24 (M+).

Biological Characterization

Example 35

Examples of Radioligand Binding Assay for Cloned Human Muscarinic Receptors

CHO-K1 clone cells expressing the human M1-, M2-, M3-receptors (Euroscreen, Swissprot P 11229, P08172, P20309, Genbank: J02960 respectively) were harvested in $Ca^{++}/Mg^{++}$ free phosphate-buffered saline and collected by centrifugation at 1500 rpm for 10 minutes, at 4° C. The pellets were resuspended in ice cold buffer A (15 mM Tris-HCl pH 7.4, 2 mM $MgCl_2$, 0.3 mM EDTA, 1 mM EGTA). Cloned cells expressing M1-, M2-, and M3-receptors were homogenized by a PBI politron (setting 5 for 15 seconds). The crude membrane fraction was collected by two consecutive centrifugation steps at 40000 g for 20 minutes at 4° C., separated by a washing step in buffer A. The pellets obtained from the three cell lines were finally resuspended in buffer C (75 mM Tris HCl pH 7.4, 12.5 mM $MgCl_2$, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM $MgCl_2$, 1 mM EDTA). The non selective muscarinic radioligand [3H]-N-methyl scopolamine (*Mol. Pharmacol.*, 45:899-907, which is incorporated herein by reference in its entirety) was used to label the M1, M2, and M3 binding sites. Binding experiments were performed in duplicate (ten point concentrations curves) in 96 well plates at radioligand concentration of 0.1-0.3 nM. The non specific binding was determined in the presence of cold N-methyl scopolamine 10 µM. Samples (final volume 0.75 ml) were incubated at RT for 120 minutes for M1, 60 min for M2 and 90 min for M3 binding assay.

The reaction was terminated by rapid filtration through GF/B Unifilter plates and two washes (0.75 ml) with cold buffer using a Packard Filtermate Harvester. Radioactivity on the filters was measured by a microplate scintillation counter TopCount NXT (Can berra Packard).

In the present assays, Ki values for the tested compounds were determined from the observed IC50 values according to known methods. A lower Ki value indicates that the tested compound has a higher binding affinity for the receptor.

The Ki values of the tested compounds of the invention are comprised between 0.1 nM and 1 µM.

The interaction with M3 muscarinic receptors can be estimated by the results of in vitro studies which evaluated the potency of the test compounds and the offset of the inhibitory activity produced after washout of the antagonists in isolated guinea pig trachea.

Example 36

In Vitro Interaction with Guinea Pigs M3 Receptors

The potency of the antagonist activity in isolated guinea pig trachea was investigated following a method previously described by Haddad E B et al. in *Br. J. Pharmacol.*, 127, 413-420, 1999, which is incorporated herein by reference in this entirety, with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction ($IC_{50}$) was taken as a measure of its potency in this bioassay.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 minute interval between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%.

The $IC_{50}$ values for the tested compounds are comprised between 0.1 nM and 300 nM.

Example 37

Plasma Stability

In order to demonstrate that the compounds are degraded, stability in human plasma at 1 and 5 hours was tested for the compound of the invention. Briefly 10 µl of a stock solution 250 µM of the compound in acetonitrile were added to 1 ml of human plasma and samples were incubated at 37° C. Plasma (50 µL) was taken after 0, 1, and 5 hours of incubation and added to 140 µl of acetonitrile with addition of verapamil as internal standard (250 ng/ml). Samples were analysed by UPLC-MS/MS analysis. Plasma stability is calculated as percentage remaining after 1 and 5 hours by dividing the peak area at 1 or 5 hours by the area of the peak at time 0.

After 1 and 5 hours of incubation, plasma stability being tested for some representative compounds of the invention result to be comprised between 0 and 25%, indicating that the compounds of the invention are very unstable in human plasma.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

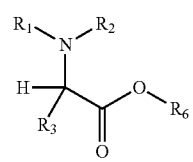

wherein:
R₁ is selected from the group consisting of $(C_1-C_6)$alkyl, aryl, $(C_3-C_8)$cycloalkyl, aryl$(C_1-C_6)$alkyl, and heteroaryl, optionally substituted by one or more substituents selected from the group consisting of halogen atoms, —OH, oxo, —SH, —NH$_2$, —NO$_2$, —CN, —CONHR$_5$, —CON(R$_5$)$_2$, —NHCOR$_5$, —COR$_5$, —CO$_2$R$_5$, (C$_1$-C$_6$)alkylsulfanyl, (C$_1$-C$_{10}$)alkylsulfinyl, (C$_1$-C$_6$)alkylsulfonyl, (C$_1$-C$_6$)alkyl, (C$_1$-C$_6$)haloalkyl, (C$_1$-C$_6$)alkoxy, and (C$_1$-C$_6$)haloalkoxy;

R$_2$ is be H or (C$_1$-C$_6$)alkyl optionally substituted by one or more substituents selected from the group consisting of halogen atoms, —OH, oxo, —SH, —NH$_2$, —NO$_2$, —CN, —ONHR$_5$, —CON(R$_5$)$_2$, —NHCOR$_5$, —COR$_5$, —CO$_2$R$_5$, (C$_1$-C$_6$)alkylsulfanyl, (C$_1$-C$_6$)alkylsulfinyl, (C$_1$-C$_6$)alkylsulfonyl, (C$_1$-C$_6$)alkyl, (C$_1$-C$_6$)haloalkyl, (C$_1$-C$_6$)alkoxy, and (C$_1$-C$_6$)haloalkoxy;

R$_3$ is H or is selected from the group consisting of (C$_1$-C$_6$) alkyl, aryl, (C$_3$-C$_8$)cycloalkyl, and heteroaryl, optionally substituted by one or more substituents selected from the group consisting of halogen atoms, —OH, oxo, —SH, —NH$_2$, —NO$_2$, —CN, —CONHR$_5$, —CON(R$_5$)$_2$, —CO$_2$R$_5$, (C$_1$-C$_6$)alkylsulfinyl, (C$_1$-C$_6$)alkylsulfonyl, (C$_1$-C$_6$)alkyl, (C$_1$-C$_6$)haloalkyl, (C$_1$-C$_6$)alkoxy, and (C$_1$-C$_6$)haloalkoxy;

R$_6$ represents a group of formula (i):

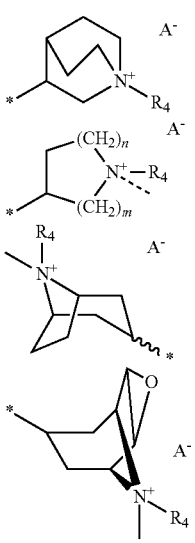

wherein
A$^-$ is a physiologically acceptable anion;
R$_4$ is a group of formula (Y):

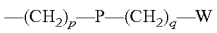 (Y)

wherein
p is 0 or an integer of 1 to 4;
q is 0 or an integer of 1 to 4;
P is a heteroaryl, optionally substituted by one or more substituents selected from the group consisting of halogen atoms, —OH, oxo, —SH, —NO$_2$, —CN, —CON(R$_5$)$_2$, —NH$_2$, —NHCOR$_5$, —CO$_2$R$_5$, (C$_1$-C$_6$)alkylsulfanyl, (C$_1$-C$_6$)alkylsulfinyl, (C$_1$-C$_6$)alkylsulfonyl, (C$_1$-C$_6$)alkyl, and (C$_1$-C$_6$)alkoxy;
W is selected from the group consisting of aryl, (C$_3$-C$_8$) cycloalkyl and heteroaryl, optionally substituted by one or more substituents selected from the group consisting of halogen atoms, —OH, oxo, —SH, —NH$_2$, —NO$_2$, —CN, —CONHR$_5$, —CON(R$_5$)$_2$, —NHCOR$_5$, —COR$_5$, —CO$_2$R$_5$, (C$_1$-C$_6$)alkylsulfanyl, (C$_1$-C$_6$) alkylsulfinyl, (C$_1$-C$_6$)alkylsulfonyl, (C$_1$-C$_6$)alkyl, (C$_1$-C$_6$)haloalkyl, (C$_1$-C$_6$)alkoxy, and (C$_1$-C$_6$)haloalkoxy;

R$_5$ is H or is selected from the group consisting of (C$_1$-C$_6$) alkyl, (C$_1$-C$_6$)haloalkyl, (C$_2$-C$_6$)alkenyl, (C$_3$-C$_8$)cycloalkyl, heteroaryl, and aryl optionally substituted by one or more substituents selected from the group consisting of halogen atoms, —OH, oxo, —SH, —NH$_2$, —NO$_2$, —CN, —CONH$_2$, —COOH, (C$_1$-C$_{10}$)alkoxycarbonyl, (C$_1$-C$_6$)alkylsulfanyl, (C$_1$-C$_6$)alkylsulfinyl, (C$_1$-C$_6$)alkylsulfonyl, (C$_1$-C$_6$)alkyl, (C$_1$-C$_6$)haloalkyl, (C$_1$-C$_6$)alkoxy, and (C$_1$-C$_6$)haloalkoxy;

or a pharmaceutically acceptable salt thereof.

2. A compound or salt thereof according to claim 1, wherein R$_1$ is aryl, aryl(C$_1$-C$_6$)alkyl, or heteroaryl, each of which may be optionally substituted by one or more substituents selected from the group consisting of halogen atoms, (C$_1$-C$_6$)alkyl, —CONHR$_5$ and —CO$_2$R$_5$; and R$_2$ is H or (C$_1$-C$_6$)alkyl.

3. A compound or salt thereof according to claim 1, wherein R$_1$ is phenyl, benzyl, or thiophenyl, each of which may be optionally substituted by one or more substituents; and R$_2$ is H or (C$_1$-C$_6$)alkyl.

4. A compound or salt thereof according to claim 2, wherein R$_1$ is phenyl, benzyl, or thiophenyl, each of which may be optionally substituted by one or more substituents; and R$_2$ is H or (C$_1$-C$_6$)alkyl.

5. A compound or salt thereof according to claim 1, wherein R$_3$ is selected from the group consisting of aryl and heteroaryl, each of which may be optionally substituted by one or more substituents selected from the group consisting of halogen atoms and (C$_1$-C$_6$)alkoxy.

6. A compound or salt thereof according to claim 1, wherein R$_3$ is selected from the group consisting of phenyl, thiophenyl, benzothiophenyl, and pyridyl, each of which may be optionally substituted.

7. A compound or salt thereof according to claim 1, wherein R$_4$ is a group of formula (Y) wherein p is 1 and q is 0, P is an heteroaryl group and W is selected from the group consisting of aryl, (C$_3$-C$_8$)cycloalkyl and heteroaryl, each of which may be optionally substituted by one or more groups selected from halogen atoms, CN, (C$_1$-C$_6$)alkyl, and (C$_1$-C$_6$) alkoxy.

8. A compound or salt thereof according to claim 1, wherein R$_4$ is a group of formula (Y) wherein p is 1 and q is 0, P is selected from oxadiazolyl, oxazolyl, triazolyl, benzoimidazolyl, thiazolyl, and isoxazolyl and W is selected from phenyl, pyrazolyl, cyclohexyl, dihydrobenzofuranyl, benzothiophenyl, piridinyl, thiazolyl, oxadiazolyl, and thiophenyl, each of which may be optionally substituted by one or more groups selected from halogen atoms, CN, methyl, and methoxy.

9. A pharmaceutical composition, comprising at least one compound or salt thereof as defined in claim 1.

10. A combination, comprising at least one compound of formula (I) or salt thereof as defined in claim 1 and one or more active ingredients selected from the group consisting of a beta2-agonist, a corticosteroid, a P38 MAP kinase inhibitor, an IKK2 inhibitor, an HNE inhibitor, a PDE4 inhibitor, a leukotriene modulator, a NSAID, and a mucus regulator.

11. A pharmaceutical composition, comprising a compound of formula (I) or salt thereof according to claim 1, which is in a form suitable for administration by inhalation, such as inhalable powders, propellant-containing metering aerosols or propellant-free inhalable formulations.

12. A pharmaceutical composition according to claim 11, which is an inhalable powder, a propellant-containing metering aerosol, or a propellant-free inhalable formulation.

* * * * *